United States Patent

Fujii et al.

[11] Patent Number: 4,824,834
[45] Date of Patent: Apr. 25, 1989

[54] PYRAZOLOTRIAZINE COMPOUNDS

[75] Inventors: Setsuro Fujii, Kyoto; Hiroyuki Kawamura, Otsu; Hiroshi Kiyokawa, Nara; Satoshi Yamada, Otsu, all of Japan

[73] Assignee: Otsuka Pharmaceutical Company, Limited, Tokyo, Japan

[21] Appl. No.: 105,581

[22] Filed: Oct. 8, 1987

[30] Foreign Application Priority Data

Oct. 31, 1986 [JP] Japan ................. 61-261008
Mar. 26, 1987 [JP] Japan ................. 62-073911
May 18, 1987 [JP] Japan ................. 62-120688
Jun. 25, 1987 [JP] Japan ................. 62-159437

[51] Int. Cl.⁴ .................... C07D 487/04; A61K 31/53
[52] U.S. Cl. ..................... 514/246; 544/219; 544/113; 514/233.2
[58] Field of Search ............ 544/212, 219; 514/246, 514/233.2

[56] References Cited

U.S. PATENT DOCUMENTS 3,865,824  2/1975  Kobe et al. ............... 544/212
3,910,907  10/1975  O'Brien et al. ........... 544/212
3,995,039  11/1976  Rooney et al. ............ 544/212
4,183,930  1/1980  Cohen .................... 544/207
4,565,815  1/1986  Kim et al. ............... 544/212

Primary Examiner—John M. Ford
Attorney, Agent, or Firm—Wegner & Bretschneider

[57] ABSTRACT

Pyrazolotriazine compounds of the formula:

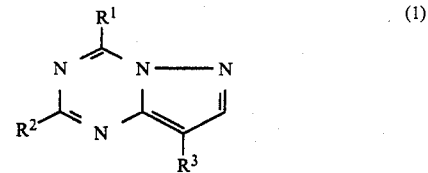

wherein $R^1$ is OH or alkanoyloxy; $R^2$ is H, OH, or SH; $R^3$ is (1) unsaturated N- or S-containing heterocyclic group optionally having 1-2 substituents of halogen, nitro or phenylthio, (2) naphthyl, (3) phenyl optionally having 1-3 substituents of (i) alkyl, (ii) phenyl, (iii) alkoxycarbonyl, (iv) cyano, (v) nitro, (vi) alkoxy, (vii) phenylalkoxy (viii) phenylthio-alkyl, (ix) phenoxy, (x)

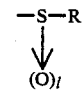

R is alkyl, halo-substituted alkyl, phenyl optionally having 1-3 substituents, or pyridyl, and l is 0, 1 or 2, (xi) halogen, (xii) phenylalkyl, (xiii) carboxy, (xiv) alkanoyl, (xv) benzoyl optionally having 1-3 substituents, (xvi) amino, (xvii) OH, (xviii) alkanoyloxy, (xix)

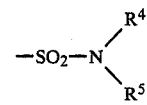

or (xx)

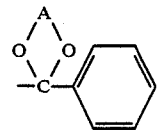

(A is alkylene), said compounds having a xanthine oxidase inhibitory activity and are useful for the prophylaxis and treatment of gout.

24 Claims, No Drawings

PYRAZOLOTRIAZINE COMPOUNDS

This invention relates to novel pyrazolotriazine compounds, more particularly, to pyrazolotriazine compounds of the formula:

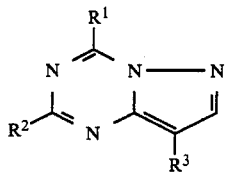

(1)

wherein
$R^1$ is hydroxy or a lower alkanoyloxy,
$R^2$ is hydrogen atom, hydroxy, or mercapto,
$R^3$ is (1) an unsaturated heterocyclic group containing nitrogen or sulfur atom as the hetero atom, which may optionally have one or two substituents selected from a halogen atom, nitro, and phenylthio, (2) naphthyl, (3) a phenyl which may optionally have one to three substituents selected from the group consisting of (i) a lower alkyl, (ii) phenyl, (iii) a lower alkoxycarbonyl, (iv) cyano, (v) nitro, (vi) a lower alkoxy, (vii) a phenyl-lower alkyl, (viii) a phenylthio-lower alkyl, (ix) phenoxy, (x) a group of the formula:

wherein R is a lower alkyl, a halogen-substituted lower alkyl, aphenyl which may optionally have one to three substituents selected from a halogen atom, a lower alkyl and a lower alkoxy, or pyridyl, and l is an integer of 0, 1 or 2, (xi) a halogen atom, (xii) a phenyl-lower alkyl, (xiii) carboxy, (xiv) a lower alkanoyl, (xv) a benzoyl which may optionally have one to three substituents selected from a halogen atom, a phenyl-lower alkoxy and hydroxy on the phenyl ring, (xvi) amino, (xvii) hydroxy, (xviii) a lower alkanoyloxy, (xix) a group of the formula:

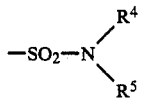

wherein $R^4$ and $R^5$ are the same or different and are each hydrogen atom, a cycloalkyl, a lower alkyl which may optionally have a substituent selected from hydroxy, furyl, thienyl, tetrahydrofuranyl and phenyl, a phenyl which may optionally have one to three substituents selected from a lower alkyl, a hydroxy-substituted lower alkyl, a lower alkanoyl, cyano, carboxy, a lower alkoxycarbonyl, hydroxy, a lower alkoxy, and a halogen atom, or a heterocyclic group selected from pyridyl, pyrimidinyl, thiazolyl, isoxazolyl, and pyrazolyl, said heterocyclic group being optionally substituted by a lower alkyl, amino, or a lower alkanoylamino, or $R^4$ and $R^5$ may join together with the adjacent nitrogen atom to form a saturated 5- or 6-membered heterocyclic group which may optionally be intervened with oxygen atom, or (xx) a group of the formula:

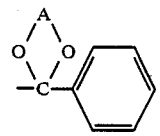

wherein A is a lower alkylene.

The pyrazolotriazine compounds of the formula (1) have a xanthine oxidase inhibitory activity and are useful as a medicine for the prophylaxis and treatment of gout.

In the above formula (1), the groups include specifically the following groups.

The "lower alkyl" includes alkyl groups having 1 to 6 carbon atoms, for example, methyl, ethyl, propyl, isopropyl, butyl, t-butyl, pentyl, hexyl, etc.

The "halogen atom" includes, for example, fluorine, chlorine, bromine, and iodine.

The "lower alkoxy" includes alkoxy groups having 1 to 6 carbon atoms, for example, methoxy, ethoxy, propoxy, isopropoxy, butoxy, t-butoxy, pentyloxy, hexyloxy, etc.

The "lower alkanoyl", "lower alkanoyloxy" and "lower alkanoylamino" include as the lower alkanoyl moiety alkanoyl groups having 1 to 6 carbon atoms, for example, formyl, acetyl, propionyl, butyryl, isobutyryl, valeryl, isovaleryl, pivaloyl, hexanoyl, etc.

The "unsaturated heterocyclic group containing nitrogen or sulfur atom as the hetero atom" includes monocyclic or condensed heterocyclic groups containing nitrogen or sulfur atom, for example, pyrrolyl, pyridyl, thienyl, thiopyranyl, indolyl, benzothienyl, 2,3-dihydrobenzothienyl, thiochromanyl, dibenzothienyl, etc. The heterocyclic group may optionally have one or two substituents selected from a halogen atom, nitro and phenylthio. Suitable examples of the heterocyclic group are, for example, 2-pyrrolyl, 3-pyrrolyl, 2-pyridyl, 3-pyridyl, 4-pyridyl, 2-thienyl, 3-thienyl, 2-thiopyranyl, 3-thiopyranyl, 4-thiopyranyl, 5-chloro-2-thienyl, 5-bromo-2-thienyl, 4-bromo-2-thienyl, 2-bromo-3-thienyl, 2,5-dichloro-3-thienyl, 2,5-dibromo-3-thienyl, 4,5-dibromo-2-thienyl, 4,5-dibromo-3-thienyl, 2-chloro-5-pyridyl, 2,3-dibromo-5-pyridyl, 5-nitro-2-thienyl, 4-nitro-2-thienyl, 3-nitro-2-thienyl, 2-nitro-3-thienyl, 2-nitro-4-pyridyl, 6-nitro-2-pyridyl, 3-phenylthio-2-thienyl, 5-phenylthio-2-thienyl, 5-phenylthio-3-thienyl, 4-phenylthio-2-pyridyl, 5-phenylthio-2-pyridyl, 1-indolyl, 2-indolyl, 3-indolyl, 4-indolyl, 5-indolyl, 6-indolyl, 7-indolyl, 1-benzothiophen-2-yl, 1-benzothiophen-3-yl, 1-benzothiophen-4-yl, 1-benzothiophen-5-yl, 1-benzothiophen-6-yl, 1-benzodihydro-1-benzothiophen-5-yl, 2,3-dihydro-1-benzothiophen-6-yl, 2,3-dihydro-1-benzothiophen-7-yl, thiochroman-5-yl, thiochroman-6-yl, thiochroman-7-yl, thiochroman-8-yl, dibenzothiophen-1-yl, dibenzothiophen-2-yl, dibenzothiophen-3-yl, dibenzothiophen-4-yl, etc.

The "naphthyl" includes, for example, 1-naphthyl, 2-naphthyl, etc.

The "lower alkoxycarbonyl" includes alkoxycarbonyl groups having 1 to 6 carbon atoms in the alkoxy moiety, for example, methoxycarbonyl, ethoxycarbonyl, propoxycarbonyl, isopropoxycarbonyl, butoxycarbonyl, t-butoxycarbonyl, pentyloxycarbonyl, hexyloxycarbonyl, etc.

The "phenyl-lower alkoxy" includes phenylalkoxy groups having 1 to 6 carbon atoms in the alkoxy moiety, for example, benzyloxy, 1-phenylethoxy, 2-phenylethoxy, 3-phenylpropoxy, 2-phenyl-1-methylethoxy, 4-phenylbutoxy, 2-phenyl-1,1-dimethylethoxy, 5-phenylpentyloxy, 6-phenylhexyyloxy, etc.

The "phenylthio-lower alkyl" includes phenylthioalkyl groups having 1 to 6 carbon atoms in the alkyl moiety, for example, phenylthiomethyl, 1-phenylthioethyl, 2-phenylthioethyl, 3-phenylthiopropyl, 2-phenylthio-1-methylethyl, 4-phenylthiobutyl, 2-phenylthio-1,1-dimethylethyl, 5-phenylthiopentyl, 6-phenylthiohexyl, etc.

The "halogen-substituted lower alkyl" includes halogen-substituted alkyl groups having 1 to 6 carbon atoms in the alkyl moiety, for example, chloromethyl, bromomethyl, 1-chloroethyl, 2-chloroethyl, 2-bromoethyl, 3-chloropropyl, 2-chloro-1-methylethyl, 2-bromobutyl, 4-bromobutyl, 2-chloro-1,1-dimethylethyl, 5-chloropentyl, 6-bromohexyl, etc.

The "phenyl which may optionally have one to three substituents selected from a halogen atom, a lower alkyl and a lower alkoxy" includes phenyl groups which may optionally have one to three substituents selected from a halogen atom, an alkyl having 1 to 6 carbon atoms and an alkoxy having 1 to 6 carbon atoms, for example, phenyl, 2-chlorophenyl, 3-chlorophenyl, 4-chlorophenyl, 2-bromophenyl, 3-bromophenyl, 4-bromophenyl, 4-fluorophenyl, 4-iodophenyl, 2,4-dibromophenyl, 2,6-dibromophenyl, 2,4,6-tribromophenyl, 2-methylphenyl, 3-methylphenyl, 4-methylphenyl, 2-ethylphenyl, 4-ethylphenyl, 3-propylphenyl, 4-(t-butyl)phenyl, 4-pentylphenyl, 4-hexylphenyl, 2,4-dimethylphenyl, 2,6-dimethylphenyl, 2-methyl-4-ethylphenyl, 2,4,6-trimethylphenyl, 2-methoxyphenyl, 3-methoxyphenyl, 4-methoxyphenyl, 2-ethoxyphenyl, 4-ethoxyphenyl, 3-propoxyphenyl, 4-(t-butoxy)phenyl, 4-pentyloxyphenyl, 4-hexyloxyphenyl, 2,6-dimethoxyphenyl, 2-methoxy-4-ethoxyphenyl, 2,4,6-trimethoxyphenyl, 2-chloro-4-methylphenyl, 2,6-dibromo-4-methylphenyl, 2-chloro-4-methoxyphenyl, 2,6-dichloro-4-methoxyphenyl, 2-bromo-4-methoxyphenyl, 2,6-dibromo-4-methoxyphenyl, 2,6-dibromo-4-ethoxyphenyl, etc.

The "phenyl-lower alkyl" includes phenylalkyl groups having 1 to 6 carbon atoms in the alkyl moiety, for example, benzyl, 1-phenylethyl, 2-phenylethyl, 3-phenylpropyl, 2-phenyl-1-methylethyl, 4-phenylbutyl, 2-phenyl-1,1-dimethylethyl, 5-phenylpentyl, 6-phenylhexyl, etc.

The "benzoyl which may optionally have one to three substituents selected from a halogen atom, a phenyl-lower alkoxy and hydroxy on the phenyl ring" includes benzoyl groups which may optionally have one to three substituents selected from a halogen atom, a phenylalkoxy having 1 to 6 carbon atoms in the alkoxy moiety and hydroxy, for example, benzoyl, 3-bromobenzoyl, 4-benzyloxybenzoyl, 4-hydroxybenzoyl, 3,5-dibromobenzoyl, 3-bromo-4-benzyloxybenzoyl, 3-chloro-4-hydroxybenzoyl, 3,5-dibromo-4-benzyloxybenzoyl, 3,5-dibromo-4-(1-phenethyloxy)benzoyl, 3,5-dibromo-4-(2-phenethyloxy)benzoyl, 3,5-dibromo-4-(3-phenylpropoxy)benzoyl, 3,5-dibromo-4-(4-phenylbutoxy)benzoyl, 3,5-dibromo-4-(5-phenylpentyloxy)benzoyl, 3,5-dibromo-4-(6-phenylhexyloxy)benzoyl, 3,5-dichloro-4-benzyloxybenzoyl, 3,5-dichloro-4-hydroxybenzoyl, 3,4-dichloro-5-hydroxybenzoyl, etc.

The "cycloalkyl" includes cycloalkyl groups having 3 to 8 carbon atoms, for example, cyclopropyl, cyclobutyl, cyclopentyl, cyclohexyl, cycloheptyl, cyclooctyl, etc.

The "furyl" includes, for example, 2-furyl, 3-furyl, etc.

The "thienyl" includes, for example, 2-thienyl, 3-thienyl, etc.

The "tetrahydrofuranyl" includes, for example, 2-tetrahydrofuranyl, 3-tetrahydrofuranyl, etc.

The "hydroxy-substituted lower alkyl" includes hydroxy-substituted alkyl groups having 1 to 6 carbon atoms in the alkyl moiety, for example, hydroxymethyl, 1-hydroxyethyl, 2-hydroxyethyl, 3-hydroxypropyl, 4-hydroxybutyl, 5-hydroxypentyl, 6-hydroxyhexyl, etc.

The "lower alkyl which may optionally have a substituent selected from hydroxy, furyl, thienyl, tetrahydrofuranyl and phenyl" includes alkyl groups having 1 to 6 carbon atoms which may optionally have a substituent selected from hydroxy, furyl, thienyl, tetrahydrofuranyl and phenyl, for example, 2-furfuryl, 3-furylmethyl, 1-(2-furyl)ethyl, 2-(3-furyl)ethyl, 3-(2-furyl)propyl, 4-(3-furyl)butyl, 3-(2-furyl)pentyl, 6-(2-furyl)hexyl, 2-thienylmethyl, 3-thienylmethyl, 1-(2-thienyl)ethyl, 2-(3-thienyl)ethyl, 3-(2-thienyl)propyl, 4-(3-thienyl)butyl, 5-(2-thienyl)pentyl, 6-(2-thienyl)hexyl, 2-tetrahydrofuranylmethyl, 3-tetrahydrofuranylmethyl, 1-(2-tetrahydrofuranyl)ethyl, 2-(3-tetrahydrofuranyl)ethyl, 3-(2-tetrahydrofuranyl)propyl, 4-(3-tetrahydrofuranyl)butyl, 5-(2-tetrahydrofuranyl)pentyl, 6-(2-tetrahydrofuranyl)hexyl, etc.

The "phenyl which may optionally have one to three substituents selected from a lower alkyl, a hydroxy-substituted lower alkyl, a lower alkanoyl, cyano, carboxy, a lower alkoxycarbonyl, hydroxy, a lower alkoxy, and a halogen atom" includes phenyl groups which may optionally have one to three substituents selected from an alkyl having 1 to 6 carbon atoms, a hydroxyalkyl having 1 to 6 carbon atoms, an alkanoyl having 1 to 6 carbon atoms, cyano, carboxy, an alkoxycarbonyl having 1 to 6 carbon atoms in the alkoxy moiety, hydroxy, an alkoxy having 1 to 6 carbon atoms, and a halogen, for example, phenyl, 2-methylphenyl, 3-methylphenyl, 4-methylphenyl, 2-ethylphenyl, 3-ethylphenyl, 4-ethylphenyl, 2-isopropylphenyl, 3-isopropylphenyl, 4-isopropylphenyl, 3-propylphenyl, 4-butylphenyl, 2-(t-butyl)phenyl, 3-(t-butyl)phenyl, 4-(t-butyl)phenyl, 4-pentylphenyl, 4-hexylphenyl, 4-hydroxymethylphenyl, 2-(1-hydroxyethyl)phenyl, 3-(1-hydroxyethyl)phenyl, 4-(1-hydroxyethyl)phenyl, 2-(2-hydroxyethyl)phenyl, 4-(2-hydroxyethyl)phenyl, 3-(3-hydroxypropyl)phenyl, 4-(4-hydroxybutyl)phenyl, 4-(5-hydroxypentyl)phenyl, 4-(6-hydroxyhexyl)phenyl, 2-acetylphenyl, 3-acetylphenyl, 4-acetylphenyl, 3-propionylphenyl, 4-butyrylphenyl, 3-valerylphenyl, 4-hexanoylphenyl, 2-cyanophenyl, 3-cyanophenyl, 4-cyanophenyl, 2-carboxyphenyl, 3-carboxyphenyl, 4-carboxyphenyl, 2-methoxycarbonylphenyl, 3-methoxycarbonylphenyl, 4-methoxycarbonylphenyl, 2-ethoxycarbonylphenyl, 4-propoxycarbonylphenyl, 4-(t-butoxycarbonyl)phenyl, 4-pentyloxycarbonylphenyl, 4-hexyloxycarbonylphenyl, 2-hydroxyphenyl, 3-hydroxyphenyl, 4-hydroxyphenyl, 2-methoxyphenyl, 3-methoxyphenyl, 4-methoxyphenyl, 2,4-dimethoxyphenyl, 2,4,6-trimethoxyphenyl, 3,4,5-trimethoxyphenyl, 4-ethoxyphenyl, 4-t-butoxyphenyl, 4-hexyloxyphenyl, 2-chlorophenyl, 3-chlorophenyl, 4-chlorophenyl, 2,4-dichlorophenyl, 3,5-dichlorophenyl, 2,4,6-trichlorophenyl, 3,4,5-trichlorophenyl, 4-bromophenyl, 4-fluorophenyl, 4-iodophenyl, 2-hydroxy-4-carboxyphenyl, 3-hydroxy-4-carboxyphenyl, 4-hydroxy-3-carboxyphenyl, 2-hydroxy-4-methoxycarbonylphenyl, 3-hydroxy-4-methoxycarbonylphenyl, 4-hydroxy-3-methoxycarbonylphenyl, 2-methoxy-4-methoxycarbonylphenyl, 3-methoxy-4-methoxycarbonylphenyl, 4-methoxy-3-methoxycarbonylphenyl, etc.

The "heterocyclic group selected from pyridyl, pyrimidinyl, thiazolyl, isoxazolyl, and pyrazolyl, said heterocyclic group being optionally substituted by a lower alkyl, amino, or a lower alkanoylamino" includes heterocyclic groups selected from pyridyl, pyrimidinyl, thiazolyl, isoxazolyl, and pyrazolyl which may optionally substituted by an alkyl having 1 to 6 carbon atoms, amino, or an alkanoylamino having 1 to 6 carbon atoms in the alkanoyl moiety, for example, 2-pyridyl, 3-pyridyl, 4-pyridyl, 2-pyrimidinyl, 4-pyrimidinyl, 5-pyrimidinyl, 2-thiazolyl, 4-isoxazolyl, 1-pyrazolyl, 3-pyrazolyl, 4-pyrazolyl, 2-methyl-4-pyridyl, 4-methyl-3-pyridyl, 3-amino-5-pyridyl, 4-amino-2-pyridyl, 2-acetylamino-4-pyridyl, 3-propanoylamino-5-pyridyl, 2-methyl-4-pyrimidinyl, 4-methyl-6-pyrimidinyl, 5-ethyl-2-pyrimidinyl, 2-amino-5-pyrimidinyl, 2-amino-4-pyrimidinyl, 4-acetylamino-2-pyrimidinyl, 4-acetylamino-6-pyrimidinyl, 4-propanoylamino-2-pyrimidinyl, 2-methyl-4-thiazolyl, 2-ethyl-5-thiazolyl, 4-methyl-2-thiazolyl, 2-amino-4-thiazolyl, 4-amino-5-thiazolyl, 2-acetylamino-4-thiazolyl, 5-acetylamino-2-thaizolyl, 5-methyl-3-isoxazolyl, 4-methyl-3-isoxazolyl, 4-methyl-5-isoxazolyl, 5-ethyl-3-isoxazolyl, 5-propyl-4-isoxazolyl, 4-isopropyl-3-isoxazolyl, 5-butyl-3-isoxazolyl, 5-pentyl-4-isoxazolyl, 5-hexyl-3-isoxazolyl, 3-amino-4-isoxazolyl, 4-amino-5-isoxazolyl, 3-acetylamino-4-isoxazolyl, 5-acetylamino-3-isoxazolyl, 1-methyl-3-pyrazolyl, 3-methyl-5-pyrazolyl, 4-ethyl-1-pyrazolyl, 5-amino-1-pyrazolyl, 4-amino-1-pyrazolyl, 3-amino-1-pyrazolyl, 5-amino-3-pyrazolyl, 5-acetylamino-1-pyrazolyl, 4-acetylamino-1-pyrazolyl, 3-acetylamino-1-pyrazolyl, 5-acetylamino-3-pyrazolyl, 5-propanoylamino-1-pyrazolyl, 4-butyrylamino-1-pyrazolyl, 5-isobutyrylamino-1-pyrazolyl, 5-valerylamino-1-pyrazolyl, 5-hexanoylamino-1-pyrazolyl, etc.

The "saturated 5- or 6-membered heterocyclic group which may optionally be intervened with oxygen atom formed by joining of $R^4$ and $R^5$ together with the adjacent nitrogen atom" includes, for example, pyrrolidinyl, piperidinyl, tetrahydro-1,2-oxazinyl, tetrahydro-1,3-oxazinyl, morpholino, etc.

The "lower alkylene" includes alkylene groups having 1 to 6 carbon atoms, for example methylene, ethylene, trimethylne, dimethylmethylene, tetramethylene, pentamethylene, hexamethylene, etc.

The "group of the formula:

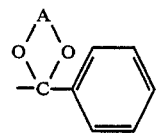

(wherein A is as defined above)" includes, for example, phenylmethylenedioxymethyl, phenylethylenedioxymethyl, phenylpropylenedioxymethyl, etc.

The compounds of this invention can be prepared by various processes, for example, by the following reaction schemes.

Reaction Scheme-1

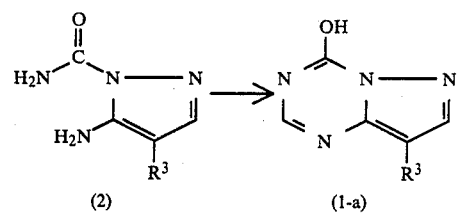

wherein $R^3$ is as defined above.

The compounds (1-a) of this invention can be prepared by reacting a compound (2) with an alkyl orthoformate (e.g. methyl orthoformate, ethyl orthoformate, etc.). The reaction can be carried out in a solvent which does not affect on the reaction, but since the alkyl orthoformate can also act as a solvent, use of a specific solvent is not necessarily essential. The reaction is usually carried out by using about 15 moles of the alkyl orthoformate per 1 mole of the compound (2) at a temperature of 80° to 120° C. for about 2 to 15 hours.

Reaction Scheme-2

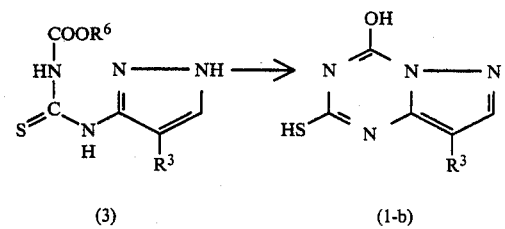

wherein $R^3$ is as defined above and $R^6$ is a lower alkyl.

The compounds (1-b) of this invention can be prepared by subjecting the compound (3) to a cyclization reaction with a basic compound such as an alkali metal hydroxide (e.g. sodium hydroxide, potassium hydroxide etc.) or an alkaline earth metal hydroxide (e.g. calcium hydroxide, etc.). The reaction can be carried out in a solvent which does not affect on the reaction, for example, a lower alcohol (e.g. methanol, ethanol, etc.). The reaction is usually carried out by using about 4 moles of the basic compound per 1 mole of the compound (3) at a temperature of −10° to 5° C. for about 5 to 40 hours.

Reaction Scheme-3

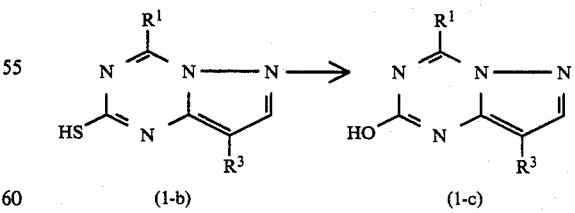

wherein $R^1$ and $R^3$ are as defined above.

The above process comprises converting the 2-mercapto group of the pyrazolotriazine compound (1-b) into hydroxy group to obtain the compound (1-c). The reaction can be carried out by reacting the compound (1-b) with hydrogen peroxide and an alkali metal hydroxide (e.g. sodium hydroxide, potassium hydroxide, etc.) in a solvent (e.g. water). The reaction is usually carried out by using about 20 moles of hydrogen peroxide per 1 mole of the compound (1-b) and about 2 moles of the alkali metal hydroxide per 1 mole of the compound (1-b) under ice-cooling for about 1 to 3 hours.

Reaction Scheme-4

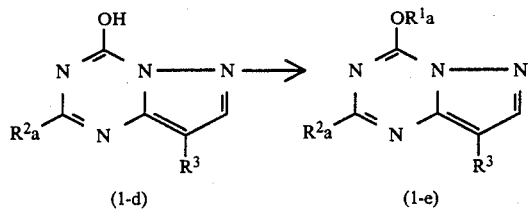

(1-d)  (1-e)

wherein $R^3$ is as defined above, $R^{1a}$ is a lower alkanoyl, and $R^{2a}$ is hydrogen atom, hydroxy, or mercapto.

The above process comprises acylating the 4-hydroxy group of the compound (1-d) to obtain the compound (1-e). The reaction can be carried out by a conventional acylating reaction, for example, an acid halide method, an acid anhydride method, a mixed acid anhydride method, an N,N'-dicyclohexylcarbodiimide method (DCC method), and the like, particularly preferably by an acid anhydride method or an acid halide method.

The acid anhyride method can be carried out by reacting the compound (1-d) with an acid anhydride in a suitable solvent. The acid anhydride includes an anhydride of an acid corresponding to the acyl group to be introduced into the 4-hydroxy group of the compound (1-d). Suitable examples of the acid anhydride are acetic anhydride, propionic anhydride, butyric anhydride, etc. These acid anhydrides are used in an amount of at least 1 mole, preferably about 1 to 3 moles, per 1 mole of the compound (1-d). The solvent includes various inert solvents, such as pyridine, halogenated hydrocarbons (e.g. chloroform, dichloromethane, etc.), ethers (dioxane, tetrahydrofuran (THF), etc.), aromatic hydrocarbons (e.g. benzene, toluene, etc.), N,N-dimethylformamide (DMF), dimethylsulfoxide (DMSO), acetonitrile, and the like. The reaction is usually carried out at a temperature from about $-30°$ C. to $100°$ C., preferably from room temperature to $80°$ C., for about 20 minutes to 20 hours. Besides, the reaction proceeds preferably in the presence of a basic compound. The basic compound includes, for example, organic basic compounds such as tertiary amines (e.g. pyridine, triethylamine, N,N-dimethylaniline, etc.), and inorganic basic compounds such as sodium hydrogen carbonate, potassium carbonate, sodium acetate, and the like.

The acid halide method is carried out by reacting the compound (1-d) with an acid halide corresponding to the acyl group to be introduced (e.g acid chloride, acid bromide, etc.) in the presence of a basic compound in a suitable solvent. The solvent and basic compound include the same solvents and basic compounds as mentioned as to the above acid anhydride method. The reaction is usually carried out at a temperature from $-30°$ C. to $80°$ C., preferably from $0°$ C. to room temperature, for about 5 minutes to 10 hours.

The compounds of this invention can be prepared by the above-mentioned processes of Reaction Schemes-1 to -4, and further, the compounds having a substituent(s) on the phenyl ring or the unsaturated heterocyclic ring having nitrogen or sulfur atom at 8-position of the compounds can also be prepared by introduction of the substituent(s) or exchange of the substituent(s) as mentioned below. In the following explanation, only the substituent(s) to be introduced or exchanged is mentioned, but the compounds may have any various substituents on the phenyl ring or the unsaturated heterocyclic ring as defined in the claims.

Exchange Reaction-1

In case of the compound having a lower alkyl group on the phenyl ring, the lower alkyl group can be converted into a carboxy group by oxidizing it with an oxidizing agent such as potassium permanganate, chromic acid, and the like. The exchange reaction can be carried out in a solvent (e.g. water) under ice cooling for about 5 to 24 hours. The oxidizing agent is preferably used in an amount of 1 to 2 moles to 1 mole of the compound having a lower alkyl group.

Exchange Reaction-2

In case of the compound having a carboxy group on the phenyl ring, the carboxy group can be converted into a corresponding ester group by a conventional esterification reaction. The exchange reaction can be carried out by reacting the compound having a carboxy group with a lower alcohol (e.g. methanol, ethanol, etc.) in the presence of a catalyst (e.g. sulfuric acid, hydrogen chloride, etc.) at a boiling point of the solvent for about 24 hours. The lower alcohol is preferably used in an amount of about 100 to 500 moles to 1 mole of the compound having a carboxy group.

Exchange Reaction-3

In case of the compound having a phenyl group substituted by a lower alkyl group containing methylene group, the methylene group can be converted into a carbonyl group by a conventional oxidization reaction. The exchange reaction can advantageously be carried out by using an oxidizing agent such as selenium dioxide, chromic acid, and the like in a solvent (e.g. acetic acid, a mixture of acetic acid and water, etc.) at a room temperature for about 10 to 18 hours. The oxidizing agent is used in an amount of about 5 moles to 1 mole of the compound containing methylene group.

Exchange Reaction-4

In case of the compound having a lower alkylenedioxy group (i.e. the carbonyl group being protected with a lower alkylene) on the phenyl ring, the lower alkylenedioxy group can be converted into a carboxy group by subjecting it to a conventional removal of a protecting group. The exchange reaction can advantageously be carried out by reacting one mole of the compound having a lower alkylenedioxy group with about 10 moles of a mineral acid (e.g. hydrochloric acid, sulfuric acid, etc.) in a solvent at a temperature of $40°$ to $60°$ C. for about 1 to 3 hours. The solvent used in the above exchange reaction includes a mixture of a lower alcohol (e.g. methanol, ethanol, etc.) and water.

Exchange Reaction-5

In case of the compound having a phenyl ring or an unsaturated heterocyclic group having nitrogen or sulfur atom as the hetero atom (hereinafter, referred to merely as unsaturated heterocyclic group) of this invention, nitro group can be introduced onto the phenyl ring or the unsaturated heterocyclic group by a conventional nitration reaction. The reaction can advantageously be carried out under the conditions as used in a conventional nitration reaction, for example, by treating with conc. nitric acid, fuming sulfuric acid, or a mixture of conc. nitric acid-conc. sulfuric acid in a solvent (e.g. acetic acid) at a temperature from room temperature to about 60° C. for about one hour. In case of introduction of nitro group onto the above unsaturated heterocyclic group, the reaction is preferably carried out at room temperature.

Exchange Reaction-6

In case of the compound having a nitro group on the phenyl ring, the nitro group can be converted into an amino group by a conventional catalytic reduction. The exchange reaction can advantageously be carried out, for example, by subjecting the compound to a hydrogenation with palladium-carbon in a mixed solvent of methanol-water at room temperature for about 14 hours.

Exchange Reaction-7

In case of the compound having an alkoxy group having optionally a phenyl substituted on the phenyl ring, the alkoxy group can be converted into a hydroxy group by reacting it with an aluminum halide. The exchange reaction can be carried out by using an aluminum halide (e.g. aluminum chloride, aluminum bromide, etc.) of about 6 moles to 1 mole of the compound having an alkoxy group in a solvent such a an aromatic compound (e.g. nitrobenzene, chlorobenzene, etc.). The reaction is advantageously carried out at a temperature of from room temperature to about 60° C. for about 1 to 5 hours. When the alkoxy group is benzyloxy group, the reaction is preferably carried out at room temperature for about one hour.

Exchange Reaction-8

In case of the compound having hydroxy group on the phenyl ring, the hydroxy group can be converted into an acyloxy group by reacting it with a lower fatty acid anhydride or lower fatty acid halide in such a manner as the acylation reaction in the above Reaction Scheme-4. The exchange reaction can be carried out by reacting one mole of the compound having hydroxy group on the phenyl ring with at least one mole, preferably 1.1 to 1.5 mole, of the lower fatty acid anhydride or lower fatty acid halide. The reaction is advantageously carried out at room temperature for about 45 minutes.

Exchange Reaction-9

In case of the compound having a lower alkylthio group on the phenyl ring, the lower alkylthio group can be converted into a lower alkylsulfinyl group by oxidizing it with an oxidizing agent such as periodate, hydrogen peroxide, and the like. The exchange reaction can be carried out by using a periodate (e.g. sodium periodate, potassium periodate, etc.) of about 2 moles to 1 mole of the compound having a lower alkylthio group in a solvent such as a mixture of a lower alcohol (e.g. methanol, ethanol, etc.) with water (40:1). The reaction is advantageously carried out at room temperature for about 40 hours. Besides, the reaction can also be carried out under the same conditions as in the above Exchange Reaction-3 except that the abovementioned solvent is used.

Moreover, in case of the compound having a phenylthio group on the phenyl ring, the phenylthio group can be converted into a phenylsulfinyl group in the same manner as described above.

Exchange Reaction-10

In case of the compound having a lower alkylthio group or lower alkylsulfinyl group on the phenyl ring, the lower alkylthio or alkylsulfinyl group can be converted into a lower alkylsulfonyl group by oxidizing it with hydrogen peroxide. The exchange reaction can be carried out by reacting one mole of the compound having a lower alkylthio or lower alkylsulfinyl group on the phenyl ring with about 30 moles of hydrogen peroxide in a solvent (e.g. acetic acid). The reaction is advantageously carried out at a temperature of about 70° to 80° C. for about one hour.

Exchange Reaction-11

Introduction of phenylthio group onto an unsaturated heterocyclic group can be done by reacting a compound having an unsaturated heterocyclic group with a halogenothiobenzene. The reaction can be carried out by reacting one mole of the compound having an unsaturated heterocyclic group with about 1.2 mole of a halogenothiobenzene which is prepared by reacting mercaptobenzene and an N-halogenated succinimide (e.g. N-chlorosuccinimide, N-bromosuccinimide, etc.), in an aprotic solvent (e.g. N,N-dimethylformamide, N,N-dimethylacetamide, etc.). The reaction is advantageously carried out at a temperature from 0° C. to room temperature for about 2 hours.

Exchange Reaction-12

Introduction of the group:

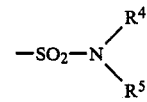

(wherein $R^4$ and $R^5$ are as defined above) onto the phenyl ring can be done by introducing sulfonic group onto the phenyl ring by reacting a compound having a phenyl group with a halogenosulfonic acid and subjecting the resultant to a conventional amido bond forming reaction. The halogenosulfonic acid used in the above reaction includes chlorosulfonic acid, bromosulfonic acid, and the like. The above reaction can advantageously be carried out by reacting one mole of a compound having a phenyl group with about 20 to 25 moles of a halogenosulfonic acid at about 80° C. for about 1 to 3 hours, by which chlorosulfonyl group is introduced onto the phenyl ring, and then reacting the resultant with an amine of the formula:

(wherein $R^4$ and $R^5$ are as defined above) without using a solvent or in the presence of an organic basic compound (e.g. pyridine, triethylamine, etc.) at a temperature of 50° to 100° C. for about 2 to 15 hours.

Exchange Reaction-13

Introduction of a halogen atom onto the phenyl ring can be done by a conventional halogenation reaction.

The halogenation reaction can be done by reacting one mole of a compound having a phenyl group with about 5 moles of a halogen molecule in a solvent such as an aromatic compound (e.g. nitrobenzene, chlorobenzene, bromobenzene, etc.). The reaction is advantageously carried out in the presence or absence of a catalyst (e.g. aluminum chloride, etc.) at a temperature of 50° to 60° C. for about 4 hours.

Besides, when a compound having a phenylthio group on the phenyl ring is subjected to the above-mentioned halogenation reaction at room temperature for about 12 hours, the compound having a phenylthio group on the phenyl ring can be converted into a compound having a halogen-substituted phenylthio group on the phenyl ring.

Moreover, when a compound having an unsaturated heterocyclic group is subjected to the above-mentioned halogenation reaction at room temperature for about one hour, a halogen atom can be introduced onto the unsaturated heterocyclic group of the compound having an unsaturated heterocyclic group.

The starting compounds of the formulae (2) and (3) in the Reaction Schemes-1 and -2 hereinabove can be prepared by processes of the following reaction schemes.

Reaction Scheme-5

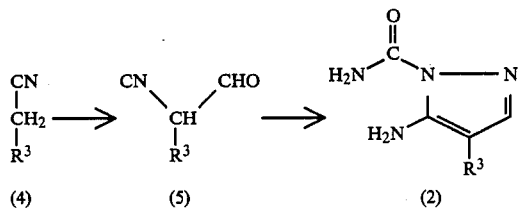

wherein $R^3$ is as defined above.

The above process comprises reacting an acetonitrile compound (4) with a formate to obtain a compound (5) and then reacting the compound (5) with a semicarbazide mineral acid salt (e.g. semicarbazide hydrochloride, semicarbazide sulfate, etc.) to obtain the compound (2).

The reaction of the compound (4) and a formate can be carried out in a solvent which does not affect on the reaction, such as aromatic hydrocarbons (e.g. benzene, toluene, xylene, etc.), N,N-dimethylformamide, dimethylsulfoxide, and the like. The formate includes methyl formate, ethyl formate, etc. and is used in an amount of at least 1 mole, preferably 1.05 to 1.25 mole, per 1 mole of the compound (4). The reaction is preferably carried out by reacting firstly under ice cooling for about 5 to 20 minutes and then at room temperature for about 4 to 12 hours. Besides, the reaction is preferably done in the presence of a sodium alkoxide (e.g. sodium methoxide, etc.) in at least equimolar amount to that of the formate. After the reaction, water is added to the reaction mixture, and the aqueous layer is separated and regulated to pH 3 to 4 with a mineral acid (e.g. hydrochloric acid, etc.) to precipitate the compound (5).

To the compound (5) thus obtained is added dropwise at least equimolar amount, preferably 1 to 1.2 mole, of a semicarbazide mineral acid salt under ice cooling, and the mixture is reacted at room temperature for about 4 to 15 hours to give the compound (2). The reaction is carried out in a solvent which does not affect on the reaction, for example, a lower alcohol (e.g. methanol, ethanol, etc.), or a mixture of the lower alcohol with water in a mixed ratio of about 1:1 to 10:1.

Reaction Scheme-6

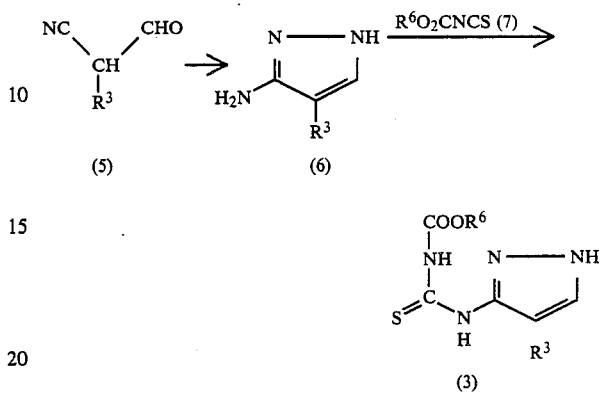

wherein $R^3$ and $R^6$ are as defined above.

The above process comprises reacting the compound (5) with a hydrazine compound (e.g. anhydrous hydrazine, hydrazine monohydrate, hydrazine hydrochloride, etc.) to obtain the compound (6), and then reacting the compound (6) with a lower alkoxycarbonyl isothiocyanate (7) to obtain the compound (3).

The reaction of the compound (5) with a hydrazine compound is carried out in a solvent which does not affect on the reaction, for example, aromatic hydrocarbons (e.g. benzene, toluene, xylene, etc.) to which about 10% (v/v) of acetic acid is added. The reaction is usually carried out by using about 1.1 to 1.5 mole of the hydrazine compound per 1 mole of the compound (5) at a boiling temperature of the solvent for about 1 to 4 hours.

The reaction of the resulting compound (6) and the compound (7) is carried out in a solvent such as an aromatic hydrocarbon (e.g. benzene, toluene, xylene, etc.), a halogenated hydrocarbon (e.g. methylene chloride, chloroform, etc.), an acetate (e.g. ethyl acetate, etc.), preferably a mixture of the above acetate with the aromatic hydrocarbon or halogenated hydrocarbon in a mixed ratio of about 1:1 to 2:1. The compound (7) is used in an amount of at least 1 mole, preferably 1 to 1.2 mole, per 1 mole of the compound (6). The compound (7) is preferably ethoxycarbonyl isothiocyanate. The reaction is usually carried out at room temperature for about 10 to 20 hours.

Reaction Scheme-7

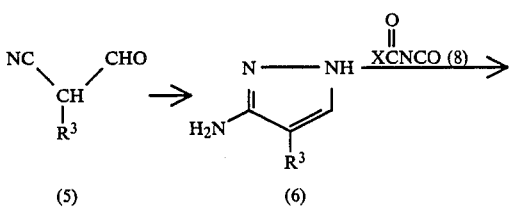

-continued
Reaction Scheme-7

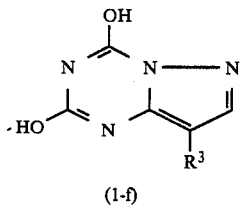
(1-f)

wherein R³ is as defined above, and X is a halogen atom.

The above process comprises reacting the compound (5) with a hydrazine compound (e.g. anhydrous hydrazine, hydrazine monohydrate, hydrazine hydrochloride, etc.) to obtain the compound (6), and then reacting the compound (6) with an N-(halogenated carbonyl) isocyanate (8) (e.g. N-(chlorocarbonyl) isocyanate, N-(bromocarbonyl) isocyanate, etc.) to obtain the compound (1-f).

The reaction of the compound (5) with a hydrazine compound is carried out in a solvent which does not affect on the reaction, for example, aromatic hydrocarbons (e.g benzene, toluene, xylene, etc.) to which about 10% (v/v) of acetic acid is added. The reaction is usually carried out by using about 1.1 to 1.5 mole of the hydrazine compound per 1 mole of the compound (5) at a boiling temperature of the solvent for about 1 to 4 hours.

The reaction of the resulting compound (6) and the compound (8) is carried out in a solvent such as an aromatic hydrocarbon (e.g. benzene, toluene, xylene, etc.), a halogenated hydrocarbon (e.g. methylene chloride, chloroform, etc.), an acetate (e.g. ethyl acetate, etc.), a tertiary amine (e.g. pyridine, triethylamine, etc.), preferably pyridine or triethylamine. There is preferably used a basic compound such as tertiary amines (e.g. pyridine, triethylamine, etc.) The compound (8) is used in an amount of at least 1 mole, preferably 1 to 1.2 mole, per 1 mole of the compound (6). The basic compound is preferably used in an amount of 10 to 100 moles, preferably 20 to 30 moles, per 1 mole of the compound (6). The reaction is usually carried out at room temperature for about 1 to 10 hours.

The starting compound (4) in the above Reaction Scheme-5 can be prepared by processes as shown in the following Reaction Schemes-8 to -13.

Reaction Scheme-8

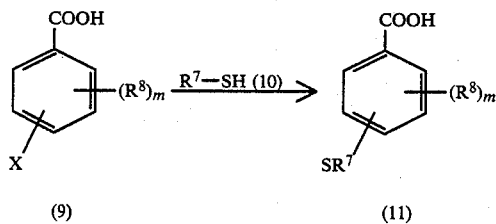

wherein X is as defined above, R⁷ is a lower alkyl, a halogen-substituted lower alkyl, or a phenyl which may optionally have one to three substituents selected from a halogen atom, a lower alkyl and a lower alkoxy, R⁸ is a substituent selected from the group consisting of (i) a lower alkyl, (ii) phenyl, (iii) a lower alkoxycarbonyl, (iv) cyano, (v) nitro, (vi) a lower alkoxy, (vii) a phenyl-lower alkoxy, (viii) a phenylthio-lower alkyl, (ix) phenoxy, (x) a group of the formula:

(wherein R and l are as defined above), (xi) a halogen atom, (xii) a phenyl-lower alkyl, (xiii) carboxy, (xiv) a lower alkanoyl, (xv) a benzoyl which may optionally have one to three substituents selected from a halogen atom, a phenyl-lower alkoxy and hydroxy on the phenyl ring, (xvi) amino, (xvii) hydroxy, (xviii) a lower alkanoyloxy, (xix) a group of the formula:

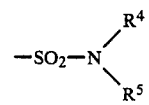

(wherein R⁴ and R⁵ are as defined above), (xx) a group of the formula:

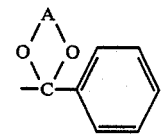

(wherein A is as defined above), or (xxi) hydrogen atom, and m is an integer of 1 or 2.

The compound (11) can be obtained by reacting the compound (9) with the compound (10) in the presence of a basic compound in an inert solvent. The inert solvent includes any solvent which does not affect on the reaction, for example, water, lower alcohols (e.g. methanol, ethanol, propanol, etc.) aprotic polar solvents such as N,N-dimethylformamide, N,N-dimethylacetamide, hexamethylphosphoric triamide, and a mixture of these solvents. The basic compound includes, for example, alkali metal hydroxides (e.g. sodium hydroxide, potassium hydroxide, etc.), alkali metal carbonates (e.g. sodium carbonate, potassium carbonate, etc.), alkali metal hydrogen carbonates (e.g. sodium hydrogen carbonate, potassium hydrogen carbonate, etc.), alkali metal alkoxides (e.g. sodium methoxide, sodium ethoxide, etc.), which may be used alone or in combination of two or more thereof.

The compound (10) is usually used in at least equimolar amount, preferably in an excess amount, to that of the compound (9). The basic compound is used in an amount of at least two moles, preferably in an excess amount, to 1 mole of the compound (9) in order to form a salt of the compound (9) and the compound (10). The reaction is usually carried out at a temperature from room temperature to 180° C. for about 30 minutes to 24 hours, by which the desired compound can be obtained in approximately quantitative yield.

The compound (11) wherein R⁸ is nitro can be converted into a compound (11) wherein R⁸ is amino by subjecting it to a conventional reducing reaction for converting nitro group into amino group. The compound having amino group thus obtained can also be converted into a compound wherein R⁸ is hydroxy group by subjecting it to Sandmeyer type reaction.

Reaction Scheme-9

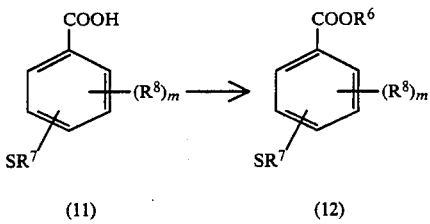

wherein $R^6$, $R^7$, $R^8$ and m are as defined above.

The ester compound (12) can be prepared by subjecting the compound (11) to a conventional esterification reaction.

The esterification reaction is carried out, for example, by reacting the compound (11) with an alcohol of the formula: $R^6$—OH (wherein $R^6$ is as defined above) in the presence of a catalyst which is usually used in an esterification reaction. Suitable examples of the catalyst are inorganic acids (e.g. hydrochloric acid, conc. sulfuric acid, phosphoric acid, polyphosphoric acid, trifluoroboron, perchlorinate, etc.), organic acids (e.g. trifluoroacetic acid, trichloromethanesulfonic acid, naphthalenesulfonic acid, p-toluenesulfonic acid, benzenesulfonic acid, ethanesulfonic acid, etc.), acid anhydrides (e.g. trichloromethanesulfonic anhydride, trifluoromethanesulfonic anhydride, etc.), thionyl chloride, and the like. Cationic exchange resins (acid type) can also be used. The above esterification reaction can be carried out in a solvent or without using any solvent. The solvent includes any solvent which is usually used in the esterification reaction, for example, aromatic hydrocarbons (e.g. benzene, toluene, xylene, etc.), halogenated hydrocarbons (e.g. dichloromethane, dichloroethane, chloroform, etc.), ethers (e.g. diethyl ether, tetrahydrofuran, dioxane, etc.), and the like. The acid is usually used in an amount of 1 to 100 moles, preferably 10 to 30 moles, per 1 mole of the compound (11). The reaction is usually carried out at a temperature of $-20°$ C. to 200° C., preferably 0° to 150° C.

The compound (12) can also be obtained by reacting an alkali metal salt (e.g. sodium salt, potassium salt, etc.) of the compound (11) with a halide compound of the formula: $R^6$—X (wherein $R^6$ and X are as defined above); by reacting the compound (11) with a diazoalkane (e.g. diazomethane, diazoethane, diazopropane, etc.); by converting the compound (11) into a reactive derivative at the carboxy group thereof and then reacting it with an alcohol of the formula: $R^6$—OH (wherein $R^6$ is as defined above). These reactions can be carried out in usual manner.

Reaction Scheme-10

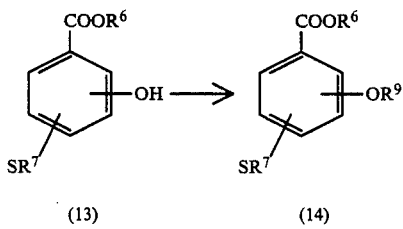

wherein $R^6$ and $R^7$ are as defined above, and $R^9$ is a lower alkyl.

The compound (14) can be prepared by alkylating the compound (13). The reaction can be carried out by a conventional alkylation reaction which is usually used in the alkylation of a phenolic hydroxy group, for example, by reacting the compound (13) with a di(lower)alkyl sulfate (e.g. dimethyl sulfate, diethyl sulfate, etc.), a lower alkyl halide (e.g. methyl iodide, methyl bromide, ethyl iodide, ethyl bromide, propyl iodide, etc.), a diazo(lower)alkane (e.g. diazomethane, diazoethane, etc.), and the like.

In case of the above reaction using a di-(lower)alkyl sulfate, the reaction is usually carried out by reacting the compound (13) with an equimolar amount of the di(lower)alkyl sulfate in an inert solvent (e.g. a lower alcohol such as methanol, ethanol, acetone, etc.) at a temperature from 50° C. to a boiling point of the solvent for about 3 to 10 hours, preferably for about 6 hours. The reaction is preferably carried out in the presence of a basic compound in order to promote the reaction rate by forming a salt of the compound (13) and further to neutralize the mono(lower)alkyl sulfate produced by the reaction. The basic compound includes the basic compounds mentioned in the above Reaction Scheme-8 and is used in an equimolar amount, preferably in excess amount, to that of the compound (13).

Reaction Scheme-11

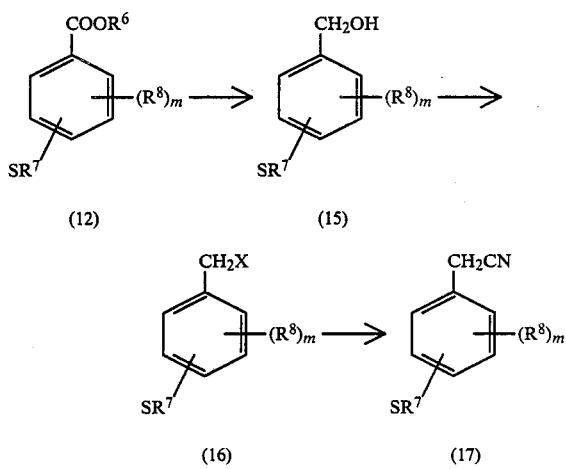

wherein $R^6$, $R^7$, $R^8$, X and m are as defined above.

The compound (12) can be converted into the compound (15) by subjecting it to a conventional reducing reaction with a metal halide reducing agent (e.g. lithium aluminum hydride, aluminum hydride, diisopropylaluminum hydride, lithium borohydride, sodium borohydride-aluminum chloride, diborane, etc.). The reducing reaction can be carried out in a solvent such as ethers (e.g. diethyl ether, tetrahydrofuran, dioxane, diglyme, etc.), aliphatic hydrocarbons (e.g. hexane, heptane, etc.), aromatic hydrocarbons (e.g. benzene, toluene, etc.), and the like. The hydrogenation reducing agent is used in an amount of at least 0.5 mole, preferably 0.6 to 1.2 mole, per 1 mole of the compound (12). The reaction is usually carried out at a temperature from ice cooling to 100° C., preferably about 0° to 50° C., for about 30 minutes to 10 hours.

The compound (16) can be obtained by reacting the compound (15) with a halogenating agent in a suitable solvent or without using any solvent. The solvent includes ethers (e.g. diethyl ether, tetrahydrofuran, dioxane, etc.), halogenated hydrocarbons (e.g. methylene chloride, chloroform, dichloroethane, etc.), aromatic hydrocarbons (e.g. benzene, toluene, etc.), and the like. The halogenating agent includes thionyl halides (e.g. thionyl chloride, thionyl bromide, etc.), hydrogen halides (e.g. hydrogen chloride, hydrogen bromide, hydrogen iodide, etc.), phosphorus halides (e.g. phosphorus trichloride, phosphorus tribromide, etc.), and the like, which is used in an amount of at least 1 mole, preferably 1–1.3 mole, per 1 mole of the compound (15). The reaction is usually carried out at a temperature from ice cooling to 100° C., preferably about 0° to 50° C., for about 30 minutes to 5 hours.

The compound (17) can be obtained by reacting the compound (16) with a cyanide compound in a suitable solvent. The solvent includes lower alcohols (e.g. methanol, ethanol, propanol, etc.), aprotic polar solvents (e.g. N,N-dimethylformamide, dimethylsulfoxide, hexamethylphosphoric triamide, etc.), or a mixture of these solvents with water. The cyanide compound includes, for example, potassium cyanide, sodium cyanide, silver cyanide, copper cyanide, calcium cyanide, and the like, which is used in an amount of at least 1 mole, preferably 1 to 1.3 mole, per 1 mole of the compound (16). The above reaction is usually carried out at a temperature from room temperature to 150° C., preferably from room temperature to 100° C., for about 1 to 20 hours.

Reaction Scheme-12

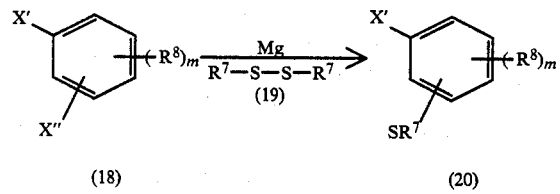

wherein $R^7$, $R^8$ and m are as defined above, $X'$ is hydrogen atom or a halogen atom, and $X''$ is a halogen atom.

The above process comprises replacing the halogen atom ($X''$) in the compound (18) with a group: $-SR^7$ to obtain the compound (20). The reaction is carried out by preparing a Grignard reagent by adding an excess amount of magnesium to the compound (18) in an ether (e.g. diethyl ether, tetrahydrofuran, etc.) and reacting the produced Grignard reagent with a disulfide compound (19). The reaction for forming Grignard reagent is preferably carried out in the presence of a catalytic amount of an iodine compound (e.g. iodine, methyl iodide, etc.). The reaction of the Grignard reagent with the compound (19) is usually carried out at a temperature from room temperature to a boiling point of the solvent for about 1 to 10 hours, wherein the compound (19) is used in an amount of at least 1 mole, preferably 1 to 1.2 mole, per 1 mole of the compound (18).

Reaction Scheme-13

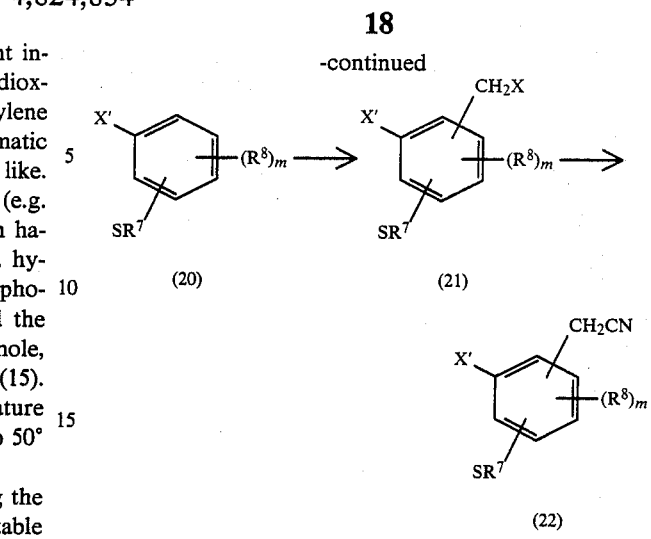

wherein $R^7$, $R^8$, X, $X'$ and m are as defined above.

The above conversion of the compound (20) to the compound (21) can be carried out by subjecting the compound (20) to a halogenomethylation by a conventional halogenomethylation reaction. The reaction is carried out by reacting the compound (20) with a halogenomethylating agent in an inert solvent in the presence of a catalyst. The inert solvent includes halogenated hydrocarbons (e.g. methylene chloride, chloroform, dichloroethane, carbon tetrachloride, etc.), carbon disulfide, and the like. The catalyst includes, for example, Lewis acids (e.g. aluminum chloride, iron chloride, zinc chloride, antimony pentachloride, tin tetrachloride, boron trifluoride, etc.), protonic acids (e.g. hydrogen fluoride, conc. sulfuric acid, etc.). The halogenomethylating agent includes, for example, chloromethyl methyl ether, bromomethyl methyl ether, dichloromethyl ether, dibromomethyl ether, and the like. The catalyst is used in an amount of 1 to 3 moles, preferably about 2 moles, per 1 mole of the compound (20). The halogenomethylating agent is used in an amount of 1 to 3 moles, preferably about 2 moles, per 1 mole of the compound (20). The above reaction is usually carried out at room temperature or an elevated temperature for about 1 to 5 hours.

In the above reaction, the position of substitution of the halogenomethyl group varies depending on the kinds and numbers of the substituents of the compound (21), the electronic density and the steric hindrance of the replaceable carbon atom(s) on the benzene ring, and when the products are obtained in a mixture of two or more different compounds, they can be isolated and purified by a conventional purification method, such as distillation, column chromatography, and the like.

The reaction of converting the compound (21) into the compound (22) is carried out in the same manner as in the conversion of the compound (16) into the compound (17) in the above Reaction Scheme-11.

In case of the compound (4) wherein $R^3$ is a phenyl having one to three groups of $-S-R'$ (wherein $R'$ is a lower alkyl, a halogen-substituted lower alkyl, or a phenyl which may have one to three substituents selected from a halogen atom, a lower alkyl and a lower alkoxy on the phenyl ring), the compound can be converted into a compound (4) wherein $R^3$ is a phenyl having one to three groups of $-SO-R'$ (wherein $R'$ is as defined above) by oxidizing it in the same manner as in the above Conversion Reaction-9. In the reaction, when hydrogen peroxide is used as the oxidizing agent, it is used in an amount of about 1 to 3 moles, preferably about 1.5 to 2.5 moles, per 1 mole of the compound (4), and the reaction is carried out at room temperature for about 4 to 24 hours, preferably about 10 hours.

The compound (4) wherein $R^3$ is a phenyl having one to three groups of —SO—R' (wherein R' is as defined above) obtained above can be converted into a compound (5) wherein $R^3$ is a phenyl having one to three groups of —SO—R' (wherein R' is as defined above) by the same method as used in the convertion of the compound (4) into the compound (5) in the above Reaction Scheme-5. Moreover, the compound can be converted into the corresponding compound (2), compound (3) and compound (1-f) by the same methods as in Reaction Schemes-5, -6 and -7, respectively.

Besides, other inventors have reported that a diphenyl thioether compound useful as an intermediate for the preparation of the pyrazolotriazine compounds of the invention can also be prepared by the process as shown in the following Reaction Scheme-14:

Reaction Scheme-14

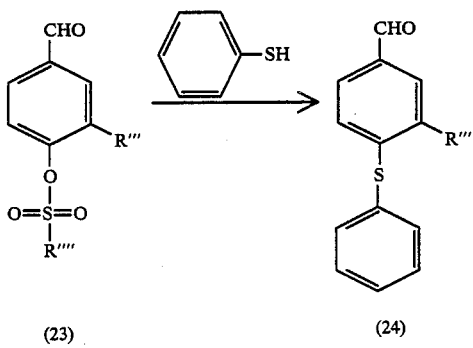

(23)　　　　　　　　　　(24)

wherein R''' is a lower alkyl or a lower alkoxy, and R'''' is a lower alkyl or a phenyl which may optionally substituted by a lower alkyl.

The above reaction can be carried out by reacting 1 mole of the benzaldehyde compound (23) with at least 1 mole, preferably 1 to 3 moles, of thiophenol in an inert solvent at a temperature of 100° to 200° C., preferably 130° to 160° C., for about 1 to 100 hours, preferbly for 2 to 70 hours. The inert solvent includes any solvent which does not affect on the reaction, for example, N,N-dimethyl-formamide, dimethylsulfoxide, acetonitrile, N,N-dimethylacetamide, hexamethylphosphoric triamide, etc., preferably N,N-dimethylformamide and hexamethylphosphoric triamide, which may be used alone or in combination of two or more thereof. The reaction is preferably carried out in the presence of a basic compound, for example, inorganic basic compounds such as alkali metal hydroxides (e.g. sodium hydroxide, potassium hydroxide, etc.), alkali metal or alkaline earth metal carbonates (e.g. sodium carbonate, potassium carbonate, calcium carbonate, etc.), or organic basic compounds such as pyridine, triethylamine, preferably pyridine and calcium carbonate, which may be used alone or in combination of two or more thereof, and further preferably carried out in an inert gas such as nitrogen gas, argon gas, etc.

The compounds (1) which contain a basic group can easily be converted into a salt thereof by treating them with a pharmaceutically acceptable acid, and the compounds (1) which contain an acidic group con easily be converted into a salt thereof by treating them with a pharmaceutically acceptable base. The acid includes inorganic acids (e.g. hydrochloric acid, sulfuric acid, phosphoric acid, hydrobromic acid, etc.) and organic acids (e.g. oxalic acid, maleic acid, fumaric acid, malic acid, tartaric acid, citric acid, lactic acid, benzoic acid, acetic acid, p-toluenesulfonic acid, methanesulfonic acid, ethanesulfonic acid, propionic acid, etc.). The base includes alkali metal or alkaline earth metal hydroxides (e.g. sodium hydroxide, potassium hydroxide, calcium hydroxide, etc.), alkali metal carbonates or hydrogen carbonates (e.g. sodium carbonate, sodium hydrogen carbonate, potassium hydrogen carbonate, etc.), and the like.

The salts of the compounds include also the intramolecular salts.

The compounds thus obtained can easily be isolated by conventional methods, such as extraction with solvents, dilution method, recrystallization, column chromatography, preparative thin layer chromatography, and the like.

The compounds (1) of this invention include also the optical isomers, which can easily be separated by a conventional optical resolution method, for example, by using an optical resoluting agent.

The compounds of the present invention are usually used in the form of a usual pharmaceutical preparation. The pharmaceutical preparation can be prepared in admixture with conventional pharmaceutically acceptable diluents or carriers, such as fillers, bulking agents, binding agents, wetting agents, disintegrators, surfactants, lubricating agents, and the like. The pharmaceutical preparation includes various preparations suitable for treatment of the diseases, for example, tablets, pills, powders, solutions, suspensions, emulsions, granules, capsules, suppositories, injections (solutions, suspensions, etc.), and the like. In the preparation of tablets, there may be used any conventional carriers, for example, excepients (e.g. lactose, white sugar, sodium chloride, glucose, urea, starches, calcium carbonate, kaolin, crystalline cellulose, silicate, etc.), binding agents (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium alginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium salts, sodium laurylsulfate, etc.), wetting agents (e.g. glycerin, starches, etc.), adsorbents (e.g. starches, lactose, kaolin, bentonite, colloidal silicates, etc.), rublicants (e.g. purified talc, stearates, boric acid powder, polyethylene glycol, etc.), and the like. The tablets may also be coated with conventional coating agents, for example, may be in the form of a sugar coated tablet, a gelatin-coated tablets, an enteric coating tablet, a film coating tablet, or a double or multiple layers tablet. In the preparation of pills, there may be used conventional carries, such as excipients (e.g. glucose, lactose, starches, cacao butter, hydrogenated vegetable oils, kaolin, talc, etc.), binding agents (e.g. gum arabic powder, tragacanth powder, gelatin, ethanol, etc.), disintegrators (e.g. laminaran, agar, etc.), and the like. In the preparation of suppositories, there may be used conventional carriers, such as polyethylene glycol, cacao butter, higher alcohols, higher alcohol esters, gelatin, semi-synthetized glycerides, and the like. In the preparation of injections, the solutions, emulsions or suspensions of the compounds are sterilized and are preferably made isotonic with the body liquid. These solutions, emulsions and suspensions are prepared by admixing the active compound with a conventional diluent, such as water, aqueous lactic acid solution, ethyl alcohol, propylene glycol, ethoxylated isostearyl alcohol, polyoxylated isostearyl alcohol, polyoxyethylene sorbitan fatty acid esters, and the like. The preparations may also be incorporated with sodium chloride, glucose or glycerin in an amount sufficient to make them isotonic with the body liquid. The preparations may also be incorporated with conventional solubilizers, buffering agents, anesthetizing agents, and further, with coloring agents, preservatives, perfumes, flavors, sweeting agents, and other medicaments. The preparations in the form of a paste, cream or gel may be prepared by using as a diluent white vaseline, paraffin, glycerin, cellulose derivatives, polyethylene glycol, silicone, bentonite, or the like.

The active compounds (1) or salts thereof may be contained in any amount in the preparations, and are usually contained in an amount of 1 to 70% by weight based on the whole weight of the preparations.

The pharmaceutical preparations of the present invention can be administered in any methods. Suitable method for administration may be selected in accordance with the preparation form, age and sex of the patients, degree of severity of the diseases, and the like. For instance, tablets, pills, solutions, suspensions, emulsions, granules and capsules are administered in oral route. In case of injection, it is administered intravenously alone or together with an auxiliary liquid (e.g. glucose, amino acid solution, etc.). The injections may also be administered in intramuscular, intracutaneous, subcutaneous, or intraperitoneal route. Suppositories are administered in intrarectal route.

The dosage of the pharmaceutical preparations of the present invention may vary according to administration methods, age and sex of the patients, severity of the diseases, and the like, but is usually in the range of about 1 to 100 mg, preferably 5 to 20 mg, of the active compound (1) or a salt thereof per 1 kg of body weight of the patient per day. The preparation is usually administered by dividing into 2 to 4 times per day.

The present invention is illustrated by the following Reference Examples, Examples, Preparations, and Experiments.

REFERENCE EXAMPLE 1

(1) A mixture of 4-chloro-3-nitrobenzoic acid (241.88 g), sodium hydrogen carbonate (100.80 g) and 50% aqueous methanol (90 ml) is stirred under nitrogen at room temperature, and thereto is added in order thiophenol (128.35 ml) and a solution of sodium hydroxide (49.6 g) in 50% aqueous methanol (200 ml). After the addition is completed, the mixture is refluxed under nitrogen atmosphere for one hour. After the reaction is completed, the reaction mixture is cooled with ice water and then adjusted to pH 2-3 with conc. hydrochloric acid. The resulting yellow precipitate is separated by filtration and washed with water to give 3-nitro-4-phenylthiobenzoic acid. This product is used in the subsequent reaction without further purification.

(2) To a mixture of the 3-nitro-4-phenylthiobenzoic acid obtained above, iron powder (201.0 g) and 50% aqueous ethanol (800 ml) is added gradually with stirring a solution of conc. hydrochloric acid (20 ml) in ethanol (40 ml) under reflux. The mixture is refluxed with stirring for 15 hours, and the reaction mixture is cooled. The precipitate is separated by filtration and washed with water. To the precipitate are added sodium hydroxide (50 g) and water (1.95 liter), and the mixture is heated to dissolve them. Insoluble materials are removed by filtration, and the filtrate is adjusted to pH 2-3 with diluted sulfuric acid under ice cooling. The precipitate is separated by filtration, washed with water and dried to give 3-amino-4-phenylthiobenzoic acid (218.28 g).

(3) 3-Amino-4-phenylthiobenzoic acid (110.27 g) is added to a heated solution of conc. sulfuric acid (81 ml) in water (400 ml), and the mixture is heated with stirring for 2 hours and then cooled to $-5°$ C. with an ice-sodium chloride bath. To the mixture is added a solution of sodium nitrite (36.25 g) in water (80 ml) which is previously ice-cooled over a period of about one hour. The mixture is further stirred at $0°-5°$ C. for 30 minutes. To the mixture is added urea (2 g), and the mixture is stirred for 30 minutes to decompose the unreacted nitrous acid. The resulting mixture is gradually added with stirring to a mixture of conc. sulfuric acid (121 ml), anhydrous sodium sulfate (168 g) and water (112 ml) at $100°-110°$ C. over a period of one hour and 15 minutes. After the addition, the mixture is stirred at the same temperature for one hour. The reaction mixture is cooled, and the resulting brown granular precipitate is separated by filtration, washed with water, and dried at $50°$ C. overnight. The product is added to a mixture of methanol (1.4 liter) and conc. sulfuric acid (70 ml), and the mixture is refluxed with stirring for 2 hours. After the reaction is completed, the reaction mixture is concentrated under reduced pressure, and to the residue is added water (1.5 liter), and the mixture is extracted with ethyl acetate (500 ml×3). The combined extracts are dried over anhydrous sodium sulfate and concentrated under reduced pressure. The residue is extracted with heated hexane (4.2 liter), and the extract is cooled. The resulting yellow precipitate is separated by filtration to give methyl 3-hyroxy-4-phenylthiobenzoate (49.37 g).

NMR (CDCl$_3$) δ: 7.13–7.71 (m, 8H), 6.47 (bs, 1H), 3.92 (s, 3H)

REFERENCE EXAMPLE 2

To a mixture of methyl 3-hyroxy-4-phenylthiobenzoate (49.11 g), potassium carbonate (27.33 g) and acetone (627 ml) is added dimethyl sulfate (17.85 ml), and the mixture is refluxed with stirring for 6 hours. The reaction mixture is cooled, and the precipitate is separated by filtration and washed with acetone. The filtrate and washings are combined and concentrated under reduced pressure to give methyl 3-methoxy-4-phenylthiobenzoate.

NMR (CDCl$_3$) δ: 7.35 ∝ 7.51 (m, 7H), 6.79 (d, J=8.57 Hz, 1H), 3.96 (s, 3H), 3.88 (s, 3H)

REFERENCE EXAMPLE 3

(1) To a solution of methyl 3-methoxy-4-phenylthiobenzoate (30.67 g) in dry diethyl ether (744 ml) is added gradually with stirring lithium aluminum hydride (4.32 g) under cooling. The mixture is stirred for one hour, and to the reaction mixture are added in order ethyl acetate, methanol and water, and the unreacted lithium aluminum hydride is decomposed. The organic layer is separated, and the aqueous layer is extracted with ethyl acetate (300 ml×2). The filtrates are combined with above organic layer and washed with saturated aqueous sodium chloride solution (300 ml×2), dried over anhydrous sodium sulfate and then concentrated under reduced pressure to give 1-hydroxymethyl-3-methoxy-4-phenylthiobenzene.

NMR (CDCl$_3$) δ: 7.20–7.37 (m, 5H), 7.04 (d, J=7.69 Hz, 1H), 6.95 (bs, 1H), 6.84 (bd, J=7.91 Hz, 1H), 4.68 (s, 2H), 3.87 (s, 3H)

(2) The 1-hydroxymethyl-3-methoxy-4-phenylthiobenzene obtained above is dissolved in methylene chloride (372 ml), and thereto is added with strring thionyl chloride (9.12 ml) under ice cooling. The mixture is stirred for one hour, and the reaction mixture is washed with ice water (500 ml×2), and thereto is added ethyl acetate (500 ml). The mixture is washed in order with 5% aqueous sodium hydrogen carbonate solution (20 ml), water (200 ml) and saturated aqueous sodium chloride solution (200 ml×2), dried over anhydrous sodium sulfate, and concentrated under reduced pressure to give 1-chloromethyl-3-methoxy-4-phenylthiobenzene.

NMR (CDCl$_3$) δ: 7.25–7.32 (m, 5H), 6.89–6.94 (m, 3H), 4.55 (s, 2H), 3.89 (s, 3H)

(3) The 1-chloromethyl-3-methoxy-4-phenylthiobenzene obtained above is dissolved in N,N-dimethylformamide (200 ml), and thereto is added finely divided sodium cyanide (7.34 g), and the mixture is stirred at 30° C. for 14 hours. To the reaction mixture are added saturated aqueous sodium chloride solution (300 ml) and ice water (300 ml), and the mixture is extracted with ethyl acetate (300 ml×3). The combined extracts are washed with saturated aqueous sodium chloride solution (200 ml×3) and dried over anhydrous sodium sulfate to give 1-cyanomethyl-3-methoxy-4-phenylthiobenzene. benzene.

NMR (CDCl$_3$) δ: 7.25–7.41 (m, 5H), 7.01 (d, J=7.70 Hz, 1H), 6.83 (s, 1H), 6.79 (d, J=7.47 Hz, 1H), 3.89 (s, 3H), 3.72 (s, 2H)

REFERENCE EXAMPLE 4

A solution of potassium hydroxide (20.86 g) in N,N-dimethylacetamide (70 ml) is heated to 150° C., and thereto are added with stirring thiophenol (19.52 ml) and 4-bromobenzoic acid (25.47 g) under nitrogen atmosphere at the same temperature. The mixture is refluxed under nitrogen atmosphere for 20 hours. The reaction mixture is poured into ice water (400 ml), and the mixture is washed with benzene (400 ml), and the aqueous layer is separated. The benzene layer is further extracted with 2.5N sodium hydroxide solution (100 ml×4). The extracts are combined with the above aqueous layer and adjusted to pH 1–2 with conc hydrochloric acid. The resulting precipitate is separated by filtration, washed with water and dried to give 4-phenylthiobenzoic acid (26.29 g).

NMR (DMSO-d$_6$) δ: 7.95 (d, J=8.57 Hz, 2H), 7.34–7.48 (m, 5H), 7.20 (d, J=8.57 Hz, 2H)

REFERENCE EXAMPLE 5

A mixture of 4-phenylthiobenzoic acid (26.29 g), conc. sulfuric acid (5 ml) and methanol (400 ml) is refluxed with stirring for 10 hours. After the reaction is completed, the reaction mixture is concentrated under reduced pressure, and to the residue is added ethyl acetate (400 ml). The mixture is washed with saturated aqueous sodium chloride solution (200 ml×3), dried over anhydrous magnesium sulfate, and concentrated under reduced pressure to give methyl 4-phenylthiobenzoate (27.44 g).

NMR (CDCl$_3$) δ: 7.89 (d, J=8.58 Hz, 2H), 7.32–7.53 (m, 5H), 7.20 (d, J=8.79 Hz, 2H), 3.88 (s, 3H)

REFERENCE EXAMPLE 6

(1) To a solution of methyl 4-phenylthiobenzoate (27 g) in dry diethyl ether (500 ml) is added gradually with stirring lithium aluminum hydride (2.5 g) under ice cooling. The mixture is stirred for one hour, and to the reaction mixture are added in order ethyl acetate and water, and the unreacted lithium aluminum hydride is decomposed. The organic layer is separated, and the aqueous layer is extracted with ethyl acetate (100 ml×2). The filtrates are combined with above organic layer and washed with saturated aqueous sodium chloride solution (100 ml×2), dried over anhydrous sodium sulfate and then concentrated under reduced pressure to give 1-hydroxymethyl-4-phenylthiobenzene (25 g).

NMR (CDCl$_3$) δ: 7.19–7.40 (m, 9H), 4.67 (s, 2H)

(2) The 1-hydroxymethyl-4-phenylthiobenzene (3.0 g) is dissolved in methylene chloride (15 ml), and thereto is added with stirring thionyl chloride (1.5 ml) under ice cooling. The mixture is stirred for one hour, and the reaction mixture is washed with ice water (10 ml×3), and thereto is added methylene chloride (50 ml). The mixture is washed in order with 5% aqueous sodium hydrogen carbonate solution (5 ml×3) and saturated aqueous sodium chloride solution (30 ml×2), dried over anhydrous sodium sulfate, and concentrated under reduced pressure to give 1-chloromethyl-4-phenylthiobenzene (3.0 g).

NMR (CDCl$_3$) δ: 7.25–7.35 (m, 9H), 4.54 (s, 2H)

(3) The 1-chloromethyl-4-phenylthiobenzene (3.0 g) is dissolved in N,N-dimemthylformamide (15 ml), and thereto is added finely divided sodium cyanide (1.0 g), and the mixture is stirred at room temperature for 17 hours. To the reaction mixture are added saturated aqueous sodium chloride solution (50 ml) and ice water (50 ml), and the mixture is extracted with ethyl acetate (100 ml×3). The combined extracts are washed with saturated aqueous sodium chloride solution (50 ml×3), dried over anhydrous sodium sulfate and concentrated under reduced pressure to give 1-cyanomethyl-4-phenylthiobenzene (2.9 g).

NMR (CDCl$_3$) δ: 7.29–7.38 (m, 9H), 3.71 (s, 2H)

REFERENCE EXAMPLE 7

Potassium hydroxide (1.368 g) is dissolved in N,N-dimethylacetamide (20 ml) with heating, and thereto is added thiophenol (1.16 ml) under nitrogen atmosphere. To the mixture is added 4-chloro-3-methylbenzoic acid, and the mixture is refluxed under nitrogen atmosphere for 2 days. After the reaction is completed, the reaction mixture is cooled and poured into ice water (about 100 ml), and the mixture is washed with benzene (50 ml) and the aqueous layer is separated. The benzene layer is further extracted with 5% aqueous sodium hydroxide solution (50 ml), and the extract is combined with the above aqueous layer and adjusted to pH 2–3 with hydrochloric acid. The resulting precipitate is separated by filtration, washed with water, and dried to give 3-methyl-4-phenylthiobenzoic acid (1.55 g).

REFERENCE EXAMPLE 8

A mixture of 3-methyl-4-phenylthiobenzoic acid (85 g), conc. sulfuric acid (20 ml) and methanol (1.2 liter) is refluxed with stirring for 4 hours. After the reaction is completed, the reaction mixture is concentrated under reduced pressure. To the residue is added ethyl acetate (1.5 liter), and the mixture is washed with saturated aqueous sodium chloride solution (400 ml×3), dried over anhydrous sodium sulfate and concentrated under reduced pressure to give methyl 3-methyl-4-phenylthiobenzoate (80.33 g).

NMR (CDCl$_3$) δ: 7.85 (bs, 1H), 7.70 (bd, J=8.13 Hz, 1H), 7.37 (bs, 5H), 7.00 (d, J=8.13 Hz, 1H)

REFERENCE EXAMPLE 9

(1) To a solution of methyl 3-methyl-4-phenylthiobenzoate (80.33 g) in dry diethyl ether (900 ml) is added gradually with stirring lithium aluminum hydride (7.08 g) under ice cooling. The mixture is stirred for one hour, and to the reaction mixture are added in order ethy acetate, methanol and water, and the unreacted lithium aluminum hydride is decomposed. The organic layer is separated, and the aqueous layer is extracted with ethyl acetate (300 ml×2). The extracts are combined with above organic layer and washed with saturated aqueous sodium chloride solution (300 ml×2), dried over anhydrous sodium sulfate and then concentrated under reduced pressure to give 1-hydroxymethyl-3-methyl-4-phenylthiobenzene.

NMR (CDCl$_3$) δ: 7.04–7.36 (m, 8H), 4.62 (s, 2H), 2.37 (s, 3H)

(2) The 1-hydroxymethyl-3-methyl-4-phenylthiobenzene obtained above is dissolved in methylene chloride (100 ml), and thereto is added with stirring thionyl chloride (23.34 ml) under ice cooling. The mixture is stirred for one hour, and the reaction mixture is washed with ice water (100 ml×3), and thereto is added ethyl acetate (500 ml). The mixture is washed in order with 5% aqueous sodium hydrogen carbonate solution (50 ml×4) and saturated aqueous sodium chloride solution (100 ml×2), dried over anhydrous sodium sulfate and concentrated under reduced pressure to give 1-chloromethyl-3-methyl-4-phenylthiobenzene.

NMR (CDCl$_3$) δ: 7.16–7.25 (m, 8H), 4.53 (s, 2H), 2.37 (s, 3H)

(3) The 1-chloromethyl-3-methyl-4-phenylthiobenzene obtained above is dissolved in N,N-dimemthylformamide (56 ml), and thereto is added finely divided sodium cyanide (18.16 g), and the mixture is stirred at room temperature overnight. To the reaction mixture are added saturated aqueous sodium chloride solution (300 ml) and ice water (300 ml), and the mixture is extracted with ethyl acetate (300 ml×3). The combined extracts are washed with saturated aqueous sodium chloride solution (200 ml×3), dried over anhydrous sodium sulfate and concentrated under reduced pressure to give 1-cyanomethyl-3-methyl-4phenylthiobenzene (45.95 g).

NMR (CDCl$_3$) δ: 7.10–7.37 (m, 8H), 3.69 (s, 2H), 2.38 (s, 3H)

REFERENCE EXAMPLE 10

To a solution of 2-bromo-4-fluorotoluene (45 g) in dry diethyl ether (500 ml) is added magnesium (for Grignard reagent, 7 g), and the mixture is refluxed with stirring. To the reaction mixture is added methyl iodide (1 ml), by which the reaction initiates vigorously, and then the mixture is stirred for 30 minutes after taking off the heating bath. Thereafter, the reaction becomes mild, and then the reaction mixture is refluxed for 30 minutes. After allowing to cool, dimethyl disulfide (24 ml) is added to the reaction mixture, and the mixture is refluxed for 3 hours. After allowing to cool, water and 10% hydrochloric acid are added to the reaction mixture, and the mixture is extracted with diethyl ether. The extract is washed with water (500 ml×3), dried over anhydrous sodium sulfate and then the solvent is distilled off. The resulting residue is distilled under reduced pressure to give 4-fluoro-2-methylthiotoluene (30 g).

b.p. (15 mmHg): 95° C.

NMR (CDCl$_3$) δ: 6.60–7.14 (m, 3H), 2.45 (s, 3H), 2.27 (s, 3H)

REFERENCE EXAMPLE 11

To a suspension of aluminum chloride (29 g) in carbon disulfide (300 ml) is added chloromethyl methyl ether (17 ml), and the mixture is stirred for 30 minutes. To the mixture is added 4-fluoro-2-methylthiotoluene (17.2 g), and the mixture is stirred at room temperature for 2 hours. To the reaction mixture is added water, and the mixture is extracted with diethyl ether. The extract is washed with water, dried over anhydrous sodium sulfate, and concentrated under reduced pressure to give 5-chloromethyl-4-fluoro-2methylthiotoluene (21 g).

NMR (CDCl$_3$) δ: 7.30 (d, J=9.0 Hz, 1H), 7.13 (d, J=8.0 Hz, 1H), 6.83 (d, J=10.5 Hz, 1H), 4.57 (s, 2H), 2.45 (s, 3H), 2.26 (s, 3H)

REFERENCE EXAMPLE 12

5-Chloromethyl-4-fluoro-2-methylthiotoluene (21 g) is dissolved in N,N-dimemthylformamide (90 ml), and thereto is added finely divided sodium cyanide (6.03 g), and the mixture is stirred at room temperature for 18 hours. To the reaction mixture are added saturated aqueous sodium chloride solution (300 ml) and ice water (300 ml), and the mixture is extracted with ethyl acetate (300 ml×3). The combined extracts are washed with saturated aqueous sodium chloride solution (200 ml×3), dried over anhydrous sodium sulfate and concentrated under reduced pressure to give 5-cyanomethyl-4-fluoro-2-methylthiotoluene.

NMR (CDCl$_3$) δ: 7.30 d, J=9.0 Hz, 1H), 7.14 (d, J=8.0 Hz, 1H), 6.85 (d, J=10.5 Hz, 1H), 3.68 (s, 2H), 2.45 (s, 3H), 2.27 (s, 3H)

REFERENCE EXAMPLE 13

To a suspension of sodium methoxide (5.56 g) in benzene (200 ml) is added dropwise with stirring a mixture of ethyl formate (8.14 g) and phenylacetonitrile (11.7 g) under ice cooling. After 30 minutes, the ice bath is taken off. After reacting for 3 hours, ice water is added to the reaction mixture, and the aqueous layer is separated. The organic layer is washed with 0.5 N sodium hydroxide solution (50 ml×3), and the aqueous layer and the washings are combined and adjusted to pH 3–4 with conc. hydrochloric acid. The mixture is stirred under ice cooling for 20 minutes, and the resulting precipitate is separated by filtration and washed with water to give α-formylphenylacetonitrile. The product is used in the subsequent procedure without further purification.

The α-formylphenylacetonitrile obtained above is dissolved in methanol-water (1:1–10:1, 200 ml), and to the solution is added with stirring semicarbazide hydrochloride (9.95 g) under ice cooling. After taking off the ice bath, the mixture is reacted for 12 hours. The reaction mixture is neturalized with 5N sodium hydroxide solution. The mixture is stirred for 20 minutes, and the resulting precipitate is separated by filtration, washed with water and dried to give 3-amino-2-carbamoyl-4-phenylpyrazole (16.82 g). This product is used in the subsequent procedure without further purification.

REFERENCE EXAMPLE 14

To a suspension of sodium methoxide (10.8 g) in benzene (300 ml) is added dropwise with stirring a mixture of ethyl formate (16.28 g) and phenylacetonitrile (23.4 g) under ice cooling. After 30 minutes, the ice bath is taken off. After reacting for 3 hours, ice water is added to the reaction mixture, and the aqueous layer is separated. The organic layer is washed with 0.5 N sodium hydroxide solution (100 ml×3), and the aqueous layer and the washings are combined and adjusted to pH 3–4 with conc. hydrochloric acid. The mixture is stirred under ice cooling for 20 minutes, and the resulting precipitate is separated by filtration and washed with water to give α-formylphenylacetonitrile (21.13 g). The product is used in the subsequent procedure without further purification.

A mixture of the α-formylphenylacetonitrile (18.85 g) obtained above, hydrazine hydrate (8.46 g), acetic acid (16.9 ml) and benzene (200 ml) is refluxed while azeotropically dehydrating. After reacting for 2 hours, the reaction mixture is cooled and washed with 6 N hydrochloric acid (28.5 ml and 12.7 ml×2). The washing liquids are combined and are neturalized with 28% aqueous ammonia. The mixture is stirred for 20 minutes, and the resulting precipitate is separated by filtration, washed with water and dried to give 3-amino-4-phenylpyrazole (15.16 g). This product is used in the subsequent procedure without further purification.

To a suspension of 3-amino-4-phenylpyrazole (3.97 g) in ethyl acetate (15 ml) - benzene (75 ml) is added with stirring a solution of ethoxycarbonyl isothiocyanate (3.28 g) in benzene (25 ml) under cooling at 5° C. After the cooling bath is taken off, the mixture is further stirred for 15 hours. The reaction mixture is concentrated under reduced pressure, and the residue is recrystallized from ethyl acetate to give N-carbethoxy-N'-[3-(4-phenyl)pyrazolyl]thiourea (3.34 g).

EXAMPLE 1

4-Hydroxy-8-phenylpyrazolo[1,5-a]-1,3,5-triazine

A mixture of 3-amino-2-carbamoyl-4-phenylpyrazole (4.8 g) and ethyl orthoformate (30 ml) is stirred at 100°–110° C. for 13 hours, and thereto is added methanol acetate. The precipitate is separated by filtration, washed with methanol or ethyl acetate, and dried to give the title compound (2.08 g).

m.p. 292°–299° C. (decomp.)
NMR (DMSO-$d_6$) δ: 8.54 (s, 1H), 8.10 (s, 1H), 7.96–8.06 (m, 2H), 7.24–7.52 (m, 3H)

In the same manner as described in Example 1 by using appropriate starting materials, there are prepared the compounds in Examples 2 to 65.

EXAMPLE 2

4-Hydroxy-8-(3-methylphenyl)pyrazolo[1,5-a]-1,3,5-triazine m.p. 262.5°–265.0° C.
NMR (DMSO-$d_6$) δ: 8.55 (s, 1H), 8.12 (s, 1H), 7.85 (bs, 1H), 7.82 (d, J=8.40 Hz, 1H), 7.31 (t, J=8.40 Hz, 1H), 7.17 (d, J=9.01 Hz, 1H), 2.36 (s, 3H)

EXAMPLE 3

4-Hydroxy-8-(4-methylphenyl)pyrazolo[1,5-a]-1,3,5-triazine m.p. >300° C.
NMR (DMSO-$d_6$) δ: 8.52 (s, 1H), 8.08 (s, 1H), 7.90 (d, J=8.19 Hz, 2H), 7.22 (d, J=8.19 Hz, 2H), 2.32 (s, 3H)

EXAMPLE 4

8-(4-Ethylphenyl)-4-hydroxypyrazolo[1,5-a]-1,3,5-triazine m.p. >300° C.
NMR (DMSO-$d_6$) δ: 8.54 (s, 1H), 8.09 (s, 1H), 7.92 (d, J=8.4 Hz, 2H), 7.26 (d, J=8.4 Hz, 2H), 2.56 (q, J=3.7 Hz, 2H), 1.20 (t, J=3.7 Hz, 3H)

EXAMPLE 5

8-(4-t-Butylphenyl)-4-hydroxypyrazolo[1,5-a]-1,3,5-triazine m.p. >300° C.
NMR (DMSO-$d_6$) δ: 8.49 (s, 1H), 8.07 (s, 1H), 7.91 (d, J=8.35 Hz, 2H), 7.42 (d, J=8.35 Hz, 2H), 1.30 (s, 9H)

EXAMPLE 6

8-p-Biphenyl-4-hydroxypyrazolo[1,5-a]-1,3,5-triazine m.p. >300° C.
NMR (DMSO-$d_6$) δ: 8.62 (s, 1H), 8.13 (s, 1H), 8.13 (d, J=8.35 Hz, 2H), 7.73 (d, J=8.35 Hz, 2H), 7.6–7.9 (m, 2H), 7.2–7.6 (m, 3H)

EXAMPLE 7

4-Hydroxy-8-(3-methoxycarbonylphenyl)pyrazolo[1,5-a]-1,3,5-triazine m.p. 273°–275° C.
NMR (DMSO-$d_6$) δ: 8.65 (s, 2H), 8.24 (dt, J=7.9 and 1.5 Hz, 1H), 8.18 (s, 1H), 7.86 (dt, J=7.7 and 1.5 Hz, 1H), 7.57 (t, J=7.7 Hz, 1H), 3.89 (s, 3H)

EXAMPLE 8

8-(4-α,α-Ethylenedioxybenzylphenyl)-4-hydroxypyrazolo[1,5-a]-1,3,5-triazine m.p. 291°–291.5° C. (decomp.)
NMR (DMSO-$d_6$) δ: 8.51 (s, 1H), 8.08 (s, 1H), 7.96 (d, J=8.35 Hz, 2H), 7.26–7.51 (m, 7H), 4.00 (s, 4H)

EXAMPLE 9

8-(4-Cyanophenyl)-4-hydroxypyrazolo[1,5-a]-1,3,5-triazine m.p. >300° C.
NMR (DMSO-$d_6$) δ: 8.70 (s, 1H), 8.24 (d, J=8.8 Hz, 2H), 8.18 (s, 1H), 7.87 (d, J=8.8 Hz, 2H)

EXAMPLE 10

4-Hydroxy-8-(3-nitrophenyl)pyrazolo[1,5-a]-1,3,5-triazine m.p. 295°–299° C.
NMR(MSO-$d_6$)δ: 8.96 (t, J=1.87, 1H), 8.73 (s, 1H), 8.42 (d, J=7.91 Hz, 1H), 8.22 (s, 1H), 8.12 (dd, J=7.03 and 2.30 Hz, 1H), 7.71 (t, J=8.02 Hz, 1H)

EXAMPLE 11

4-Hydroxy-8-(2-methoxyphenyl)pyrazolo[1,5-a]-1,3,5-triazine m.p. 298°–299° C. (decomp.)

NMR (DMSO-d$_6$) δ: 8.44 (s, 1H), 8.03 (s, 1H), 8.0-8.1 (m, 1H), 6.91-7.37 (m, 3H)

EXAMPLE 12

4-Hydroxy-8-(3-methoxyphenyl)pyrazolo[1,5-a]-1,3,5-triazine m.p. 288°-290° C.

NMR (DMSO-d$_6$) δ: 8.59 (s, 1H), 8.12 (s, 1H), 7.59-7.65 (m, 2H), 7.33 (t, J=7.1 Hz, 1H), 6.84 (ddd, J=7.0, 1.5 and 1.0 Hz, 1H), 3.81 (s, 3H)

EXAMPLE 13

4-Hydroxy-8-(4-methoxyphenyl)pyrazolo[1,5-a]-1,3,5-triazine m.p. 297.5°-305° C.

NMR (DMSO-d$_6$) δ: 8.48 (s, 1H), 8.06 (s, 1H), 7.92 (d, J=9.01 Hz, 2H), 6.98 (d, J=9.01 Hz, 2H), 3.78 (s, 3H)

EXAMPLE 14

8-(4-Benzyloxyphenyl)-4-hydroxypyrazolo[1,5-a]-1,3,5-triazine m.p. >300° C.

NMR (DMSO-d$_6$) δ: 8.48 (s, 1H), 8.05 (s, 1H), 7.93 (d, J=8.79 Hz, 2H), 7.33-7.42 (m, 5H), 7.07 (d, J=8.79 Hz, 2H), 5.12 (s, 2H)

EXAMPLE 15

4-Hydroxy-8-(3-methylthiophenyl)pyrazolo[1,5-a]-1,3,5-triazine m.p. 240°-243° C.

NMR (DMSO-d$_6$) δ: 8.61 (s, 1H), 8.12 (s, 1H), 7.84 (t, J=1.5 Hz, 1H), 7.80 (dt, J=7.7 and 1.5 Hz, 1H), 7.37 (t, J=7.7 Hz, 1H), 7.15 (dt, J=7.7 and 1.4 Hz, 1H), 2.52 (s, 3H)

EXAMPLE 16

4-Hydroxy-8-(4-methylthiophenyl)pyrazolo[1,5-a]-1,3,5-triazine m.p. >300° C.

NMR (DMSO-d$_6$) δ: 8.56 (s, 1H), 8.10 (s, 1H), 7.97 (d, J=8.6 Hz, 2H), 7.32 (d, J=8.6 Hz, 2H), 2.50 (s, 3H)

EXAMPLE 17

8-(4-Ethylthiophenyl)-4-hydroxypyrazolo[1,5-a]-1,3,5-triazine m.p. 288°-289° C.

NMR (DMSO-d$_6$) δ: 8.56 (s, 1H), 8.11 (s, 1H), 7.98 (d, J=8.6 Hz, 2H), 7.37 (d, J=8.6 Hz, 2H), 3.00 (q, J=7.4 Hz, 2H), 1.25 (t, J=7.4 Hz, 3H)

EXAMPLE 18

8-(4-β-Chloroethylthiophenyl)-4-hydroxypyrazolo[1,5-a]-1,3,5-triazine m.p. 249° C. (decomp.)

NMR (DMSO-d$_6$) δ: 8.58 (s, 1H), 8.11 (s, 1H), 8.00 (d, J=8.6 Hz, 2H), 7.46 (d, J=8.6 Hz, 2H), 3.68-3.85 (m, 2H), 3.20-3.43 (m, 2H)

EXAMPLE 19

4-Hydroxy-8-(4-phenylthiophenyl)pyrazolo[1,5-a]-1,3,5-triazine m.p. 297°-298° C.

NMR (DMSO-d$_6$) δ: 8.58 (s, 1H), 8.12 (s, 1H), 8.04 (d, J=8.4 Hz, 2H), 7.41 (d, J=8.5 Hz, 2H), 7.34 (s, 5H)

EXAMPLE 20

4-Hydroxy-8-[4-(2-methylphenylthio)phenyl]-pyrazolo[1,5-a]-1,3,5-triazine m.p. >300° C.

NMR (DMSO-d$_6$) δ: 8.55 (s, 1H), 8.10 (s, 1H), 8.00 (d, J=8.35 Hz, 2H), 7.27 (d, J=8.35 Hz, 2H), 7.20-8.29 (m, 4H)

EXAMPLE 21

4-Hydroxy-8-[4-(4-methylphenylthio)phenyl]-pyrazolo[1,5-a]-1,3,5-triazine m.p. >300° C.

NMR (DMSO-d$_6$) δ: 8.56 (s, 1H), 8.11 (s, 1H), 7.99 (d, J=8.6 Hz 2H), 7.32 (d, J=8.6 Hz, 2H), 7.30 (t, J=8.8 Hz, 2H), 7.18 (d, J=8.8 Hz, 2H), 2.31 (s, 3H)

EXAMPLE 22

8-(2-Fluorophenyl)-4-hydroxypyrazolo[1,5-a]-1,3,5-triazine m.p. 293°-294° C.

NMR (DMSO-d$_6$) δ: 8.37 (d, J=3.30 Hz, 1H), 8.14 (s, 1H), 8.11-8.24 (m, 1H), 7.22-7.40 (m, 3H)

EXAMPLE 23

8-(3-Fluorophenyl)-4-hydroxypyrazolo[1,5-a]-1,3,5-triazine m.p. >300° C.

NMR (DMSO-d$_6$) δ: 8.64 (s, 1H), 8.15 (s, 1H), 7.82-7.94 (m, 2H), 7.33-7.58 (m, 1H), 6.95-7.18 (m, 1H)

EXAMPLE 24

8-(4-Fluorophenyl)-4-hydroxypyrazolo[1,5-a]-1,3,5-triazine m.p. >300° C.

NMR (DMSO-d$_6$) δ: 8.56 (s, 1H), 8.11 (s, 1H), 8.05 (dd, J=5.0 and 9.01 Hz, 2H), 7.25 (dd, J=8.61 and 9.01 Hz, 2H)

EXAMPLE 25

8-(2-Chlorophenyl)-4-hydroxypyrazolo[1,5-a]-1,3,5-triazine m.p. 293°-295° C.

NMR (DMSO-d$_6$) δ: 8.38 (s, 1H), 8.08 (s, 1H), 7.33-7.75 (m, 4H)

EXAMPLE 26

8-(3-Chlorophenyl)-4-hydroxypyrazolo[1,5-a]-1,3,5-triazine m.p. >300° C.

NMR (DMSO-d$_6$) δ: 8.62 (s, 1H), 8.15 (s, 2H), 7.96 (bd, J=7.21 Hz, 1H), 7.2-7.5 (m, 2H)

EXAMPLE 27

8-(4-Chlorophenyl)-4-hydroxypyrazolo[1,5-a]-1,3,5-triazine m.p. >300° C.

NMR (DMSO-d$_6$) δ: 8.60 (s, 1H), 8.13 (s, 1H), 8.06 (d, J=8.6 Hz, 2H), 7.49 (d, J=8.6 Hz, 2H)

EXAMPLE 28

8-(3,4-Dimethylphenyl)-4-hydroxypyrazolo[1,5-a]-1,3,5-triazine m.p. >300° C.

NMR (DMSO-d$_6$) δ: 8.52 (s, 1H), 8.09 (s, 1H), 7.78 (bs, 1H), 7.74 (dd, J=8.4 and 1.8 Hz, 1H), 7.17 (d, J=8.4 Hz, 1H), 2.27 (s, 3H), 2.24 (s, 3H)

EXAMPLE 29

4-Hydroxy-8-(4-methoxy-3-methylphenyl)-pyrazolo[1,5-a]-1,3,5-triazine m.p. 279.5°–280.5° C. (decomp.)
NMR (DMSO-d$_6$) δ: 8.45 (s, 1H), 8.06 (s, 1H), 7.75–7.82 (m, 2H), 6.95 (d, J=9.23 Hz, 1H), 3.81 (s, 3H), 2.21 (s, 3H)

EXAMPLE 30

4-Hydroxy-8-(3-methyl-4-methylthiophenyl)-pyrazolo[1,5-a]-1,3,5-triazine m.p. 273°–276° C.
NMR (DMSO-d$_6$) δ: 8.54 (s, 1H), 8.09 (s, 1H), 7.85 (d, J=9.0 Hz, 1H), 7.83 (s, 1H), 7.25 (d, J=9.0 Hz, 1H), 2.48 (s, 3H), 2.30 (s, 3H)

EXAMPLE 31

8-(4-Ethylthio-3-methylphenyl)-4-hydroxypyrazolo[1,5-a]-1,3,5-triazine m.p. 260°–263° C.

NMR (DMSO-d$_6$) δ: 8.50 (s, 1H), 8.08 (s, 1H), 7.77–7.94 (m, 2H), 7.31 (d, J=9.01 Hz, 1H), 2.96 (q, J=7.26 Hz, 2H), 2.33 (s, 3H), 1.28 (t, J=7.26 Hz, 3H)

EXAMPLE 32

8-(4-Benzylthio-3-methylphenyl)-4-hydroxypyrazolo[1,5-a]-1,3,5-triazine m.p 234°–236° C.
NMR (DMSO-d$_6$) δ: 8.55 (s, 1H), 8.10 (s, 1H), 7.86 (s, 1H), 7.82 (dd, J=8.0 and 1.7 Hz, 1H), 7.20–7.45 (m, 6H), 4.21 (s, 2H), 2.28 (s, 3H)

EXAMPLE 33

4-Hydroxy-8-(3-methyl-4-phenylthiophenyl)-pyrazolo[1,5-a]-1,3,5-triazine m.p. 274°–276° C.
NMR (DMSO-d$_6$) δ: 8.59 (s, 1H), 8.13 (s, 1H), 8.01 (bs, 1H), 7.89 (dd, J=8.1 and 1.5 Hz, 1H), 7.36 (d, J=8.0 Hz, 1H), 7.11–7.42 (m, 5H), 2.36 (s, 3H)

EXAMPLE 34

4-Hydroxy-8-[3-methyl-4-(2-methylphenylthio)phenyl]pyrazolo[1,5-a]-1,3,5-triazine m.p. 246°–251° C. (decomp.)
NMR (DMSO-d$_6$) δ: 8.56 (s, 1H), 8.11 (s, 1H), 7.98 (bs, 1H), 7.84 (bd, J=8.13 Hz, 1H), 6.9–7.4 (m, 5H), 2.36 (s, 3H), 2.33 (s, 3H)

EXAMPLE 35

4-Hydroxy-8-[3-methyl-4-(3-methylphenylthio)phenyl]pyrazolo[1,5-a]-1,3,5-triazine m.p 270°–273° C.
NMR (DMSO-d$_6$) δ: 8.59 (s, 1H), 8.13 (s, 1H), 7.99 (s, 1H), 7.87 (dd, J=7.9 and 1.7 Hz, 1H), 7.32 (d, J=8.0 Hz, 1H), 6.90–7.40 (m, 4H), 2.36 (s, 3H), 2.26 (s, 3H)

EXAMPLE 36

4-Hydroxy-8-[3-methyl-4-(4-methylphenylthio)phenyl]pyrazolo[1,5-a]-1,3,5-triazine m.p. 287°–290° C.

NMR (DMSO-d$_6$) δ: 8.56 (s, 1H), 8.12 (s, 1H), 7.97 (d, J=1.5 Hz, 1H), 7.82 (dd, J=9.3 and 2.0 Hz, 1H), 7.23 (d, J=9.3 Hz, 1H), 7.15 (s, 4H), 2.35 (s, 3H), 2.28 (s, 3H)

EXAMPLE 37

4-Hydroxy-8-[4-(3-methoxyphenylthio)-3-methyl]phenylpyrazolo[1,5-a]-1,3,5-triazine m.p. 245°–249° C.
NMR (DMSO-d$_6$) δ: 8.60 (s, 1H), 8.13 (s, 1H), 8.02 (bs, 1H), 7.91 (dd, J=7.9 and 1.6 Hz, 1H), 7.39 (d, J=8.4 Hz, 1H), 7.20 (d, J=8.1 Hz, 1H), 6.67–6.85 (m, 3H), 3.70 (s, 3H), 2.36 (s, 3H)

EXAMPLE 38

4-Hydroxy-8-(4-(4-methoxyphenylthio)-3-methyl)-phenylpyrazolo[1,5-a]-1,3,5-triazine m.p. 283°–287° C.
NMR (DMSO-d$_6$) δ: 8.53 (s, 1H), 8.10 (s, 1H), 7.92 (d, J=1.5 Hz, 1H), 7.77 (dd, J=8.1 and 1.7 Hz, 1H), 7.31 (d, J-9.0 Hz, 2H), 7.03 (d, J=8.1 Hz, 1H), 6.97 (d, J=9.0 Hz, 2H), 3.77 (s, 3H), 2.36 (s, 3H)

EXAMPLE 39

8-(3-Ethyl-4-methylthiophenyl)-4-hydroxypyrazolo[1,5-a]-1,3,5-triazine m.p. 289°–294° C. (decomp.)
NMR (DMSO-d$_6$) δ: 8.46 (s, 1H), 8.05 (s, 1H), 7.77–7.87 (m, 2H), 7.25 (d, J=9.01 Hz, 1H), 2.71 (q, J=7.25 Hz, H), 2.52 (s, 3H), 1.24 (t, J=7.25 Hz, 3H)

EXAMPLE 40

8-(3,4-Dimethoxyphenyl)-4-hydroxypyrazolo[1,5-a]1,3,5-triazine m.p. 250° C. (decomp.)
NMR (DMSO-d$_6$) δ: 8.55 (s, 1H), 8.09 (s, 1H), 7.62 (s, 1H), 7.57 (bd, J=8.13 Hz, 1H), 6.99 (d, J=8.13 Hz, 1H), 3.83 (s, 3H), 3.79 (s, 3H)

EXAMPLE 41

8-[(3,4-Bismethylthio)phenyl]-4-hydroxypyrazolo[1,5-a]-1,3,5-triazine m.p. 286°–292° C.
NMR (DMSO-d$_6$) δ: 8.63 (s, 1H), 8.12 (s, 1H), 7.91 (d, J=1.76 Hz, 1H), 7.85 (dd, J=8.13 and 1.76 Hz, 1H), 7.29 (d, J=8.13 Hz, 1H), 2.53 (s, 3H), 2.48 (s, 3H)

EXAMPLE 42

8-(3,4-Difluorophenyl)-4-hydroxypyrazolo[1,5-a]1,3,5-triazine m.p.>300° C.
NMR (DMSO-d$_6$) δ: 8.61 (s, 1H), 8.15 (s, 1H), 7.2–8.2 (m, 3H)

EXAMPLE 43

8-(3-Chloro-4-methylthiophenyl)-4-hydroxypyrazolo[1,5-a]-1,3,5-triazine m p. 282°–286° C.
NMR (DMSO-d$_6$) δ: 8.63 (s, 1H), 8.15 (d, J=2.0 Hz, 1H), 8.14 (s, 1H), 7.99 (dd, J=8.3 and 2.0 Hz, 1H), 7.36 (d, J=8.3 Hz, 1H), 2.52 (s, 3H)

EXAMPLE 44

8-(3,4-Dichlorophenyl)-4-hydroxypyrazolo[1,5-a]1,3,5-triazine m.p. 296.5°–297.5° C.
NMR (DMSO-d$_6$) δ: 8.63 (s, 1H), 8.31 (d, J=1.98 Hz, 1H), 8.15 (s, 1H), 8.01 (dd, J=8.57 and 1.98 Hz, 1H), 7.64 (d, J=8.57 Hz, 1H)

EXAMPLE 45

8-(2,4-Difluorophenyl)-4-hydroxypyrazolo[1,5-a]-1,3,5-triazine m.p.>300° C.
NMR (DMSO-d$_6$) δ: 8.61 (s, 1H), 8.15 (s, 1H), 7.7–8.2 (m, 2H), 7.2–7.6 (m, 1H)

EXAMPLE 46

8-(2,4-Dichlorophenyl)-4-hydroxypyrazolo[1,5-a]-1,3,5-triazine m.p.>300° C.
NMR (DMSO-d$_6$) δ: 8.39 (s, 1H), 8.09 (s, 1H), 7.75 (d, J=8.13 Hz, 1H), 7.70 (d, J=2.19 Hz, 1H), 7.49 (dd, J=2.19 and 8.13 Hz, 1H)

EXAMPLE 47

8-(3,5-Dimethylphenyl)-4-hydroxypyrazolo[1,5-a]-1,3,5-triazine m.p.>300° C.
NMR (DMSO-d$_6$) δ: 8.52 (s, 1H), 8.11 (s, 1H), 7.63 (s, 2H), 6.90 (s, 1H), 2.31 (s, 6H)

EXAMPLE 48

8-(3,5-Dimethoxyphenyl)-4-hydroxypyrazolo[1,5-a]-1,3,5-triazine m.p. 280° C. (decomp.)
NMR (DMSO-d$_6$) δ: 8.61 (s, 1H), 8.12 (s, 1H), 7.23 (d, J=2.4 Hz, 2H, 6.42 (t, J=2.4 Hz, 1H), 3.79 (s, 6H)

EXAMPLE 49

8-(3,5-Dichlorophenyl)-4-hydroxypyrazolo[1,5-a]-1,3,5-triazine m.p.>300° C.
NMR (DMSO-d$_6$) δ: 8.68 (s, 1H), 8.18 (s, 1H), 8.09 (d, J=1.98 Hz, 2H), 7.39 (t, J=1.98 Hz, 1H)

EXAMPLE 50

8-(2-Fluoro-4-methylthiophenyl)-4-hydroxypyrazolo[1,5-a]-1,3,5-triazine m.p. 270°–272° C.
NMR (DMSO-d$_6$) δ: 8.33 (d, J=3.5 Hz, 1H), 8.13 (s, 1H), 8.11 (t, J=8.5 Hz, 1H), 7.21 (dd, J=12.0 and 1.7 Hz, 1H), 7.19 (dd, J=8.6 and 1.6 Hz, 1H), 2.53 (s, 3H)

EXAMPLE 51

4-Hydroxy-8-(3,4,5-trimethoxyphenyl)pyrazolo[1,5a]-1,3,5-triazine m.p. 262°–265° C.
NMR (DMSO-d$_6$) δ: 8.63 (s, 1H), 8.12 (s, 1H), 7.35 (s, 2H), 3.85 (s, 6H), 3.70 (s, 3H)

EXAMPLE 52

8-(4-Benzyloxy-3,5-dichlorophenyl)-4-hydroxypyrazolo[1,5-a]-1,3,5-triazine m.p. 273°–273.5° C. (decomp.)
NMR (DMSO-d$_6$) δ: 8.66 (s, 1H), 8.17 (s, 3H), 7.2–7.7 (m, 5H), 5.03 (s, 2H)

EXAMPLE 53

4-Hydroxy-8-(3,4,5-trichlorophenyl)pyrazolo[1,5-a]-1,3,5-triazine m.p.>300° C.
NMR (DMSO-d$_6$) δ: 8.56 (s, 1H), 8.34 (s, 2H), 8.08 (s, 1H)

EXAMPLE 54

8-(2-Fluoro-5-methyl-4-methylthiophenyl)-4hydroxypyrazolo[1,5-a]-1,3,5-triazine m.p.>300° C.
NMR (DMSO-d$_6$) δ: 8.32 (d, J=3.3 Hz, 1H), 8.13 (s, 1H), 7.94 (d, J=7.9 Hz, 1H), 7.11 (d, J=12.0 Hz, 1H), 2.51 (s, 3H), 2.24 (s, 3H)

EXAMPLE 55

4-Hydroxy-8-(3-thienyl)pyrazolo[1,5-a]-1,3,5-triazine m.p. 292°–293° C. (decomp.)
NMR (DMSO-d$_6$) δ: 8.48 (s, 1H), 8.07 (s, 1H), 7.90 (dd, J=1.32 and 2.86 Hz, 1H), 7.73 (dd, J=1.32 and 5.05 Hz, 1H), 7.58 (dd, J=2.86 and 5.05 Hz, 1H)

EXAMPLE 56

4-Hydroxy-8-(2-thienyl)pyrazolo[1,5-a]-1,3,5-triazine m.p. 267°–277° C. (decomp.)
NMR (DMSO-d$_6$) δ: 8.44 (s, 1H), 8.10 (s, 1H), 7.47 (dd, J=5.05 and 1.10 Hz, 1H), 7.53 (dd, J=3.52 and 1.10 Hz, 1H), 7.10 (dd, J=3.52 and 5.05 Hz, 1H)

EXAMPLE 57

4-Hydroxy-8-(2-pyridyl)pyrazolo[1,5-a]-1,3,5-triazine m.p 265°–267° C.
NMR (DMSO-d$_6$) δ: 8.58 (bs, 2H), 8.27 (d, J=8.13 Hz, 1H), 8.17 (s, 1H), 7.83 (dt, J=7.70 and 1.76 Hz, 1H), 7.15–7.31 (m, 1H)

EXAMPLE 58

4-Hydroxy-8-(3-pyridyl)pyrazolo[1,5-a]-1,3,5-triazine m.p. 241°–243.5° C.
NMR (DMSO-d$_6$) δ: 9.19 (d, J=2.20 Hz, 1H), 8.64 (s, 1H), 8.28–8.49 (m, 2H), 8.14 (s, 1H), 7.42 (dd, J=7.91 and 4.83 Hz, 1H)

EXAMPLE 59

4-Hydroxy-8-(4-pyridyl)pyrazolo[1,5-a]-1,3,5-triazine 2 m.p.>300° C.
NMR (DMSO-d$_6$) δ: 8.68 (s, 1H), 8.57 (d, J=8.57 Hz, 2H), 8.18 (s, 1H), 8.00 (d, J=8.57 Hz, 2H)

EXAMPLE 60

8-(3-Indolyl)-4-hydroxypyrazolo[1,5-a]-1,3,5-triazine m.p.>300° C.
NMR (DMSO-d$_6$) δ: 11.31 (s, 1H), 8.55 (s, 1H), 8.05 (s, 1H), 8.00–8.10 (m, 1H), 7.84 (d, J=2.4 Hz, 1H), 7.40–7.50 (m, 1H), 7.05–7.25 (m, 2H)

EXAMPLE 61

8-(3-Benzo[b]thienyl)-4-hydroxypyrazolo[1,5-a]-1,3,5-triazine m.p. 289°–292° C.

NMR (DMSO-d$_6$) δ: 8.51 (s, 1H), 8.10 (s, 1H), 8.00-8.08 (m, 2H), 7.96 (s, 1H), 7.38-7.48 (m, 2H)

EXAMPLE 62

8-(2-Benzo[b]thienyl)-4-hydroxypyrazolo[1,5-a]-1,3,5-triazine m.p. >300° C.

NMR (DMSO-d$_6$) δ: 8.55 (s, 1H), 8.16 (s, 1H), 7.85 (s, 1H), 7.77-8.00 (m, 2H), 7.27-7.39 (m, 2H)

EXAMPLE 63

4-Hydroxy-8-(6-thiochromanyl)pyrazolo[1,5-a]-1,3,5-triazine m.p. 260° C. (decomp.)

NMR (DMSO-d$_6$) δ: 8.51 (s, 1H), 8.08 (s, 1H), 7.72 (d, J=8.8 Hz, 1H), 7.70 (s, 1H), 7.09 (d, J=8.8 Hz, 1H), 3.05 (t, J=5.6 Hz, 2H), 2.81 (t, J=5.6 Hz, 2H), 1.90-2.10 (m, 2H)

EXAMPLE 64

8-[(2,3-Dihydrobenzo[b]thiophen)-5-yl]-4hydroxypyrazolo[1,5-a]-1,3,5-triazine m.p. >300° C.

NMR (DMSO-d$_6$) δ: 8.53 (s, 1H), 8.08 (s, 1H), 7.91 (d, J=1.3 Hz, 1H), 7.79 (dd, J=8.0 and 1.5 Hz, 1H), 7.27 (d, J=7.9 Hz, 1H), 3.35 (s, 2H), 3.26 (s, 2H)

EXAMPLE 65

4-Hydroxy-8-β-naphthylpyrazolo[1,5-a]-1,3,5-triazine m.p. >300° C.

NMR (DMSO-d$_6$) δ: 8.68 (s, 1H), 8.53 (bs, 1H), 8.1-8.3 (m, 1H), 8.16 (s, 1H), 7.8-8.0 (m, 4H), 7.4-7.6 (m, 2H)

EXAMPLE 66

8-(4-Carboxyphenyl)-4-hydroxypyrazolo[1,5-a]-1 3 5-triazine

4-Hydroxy-8-(4-methylphenyl)pyrazolo[1,5-a]-1,3,5-triazine (1.13 g) is suspended in 1N sodium hydroxide solution (50 ml), and thereto is added gradually with stirring potassium permanganate (1.58 g) under cooling. After 10 minutes, the ice bath is taken off. After reacting for 5 hours, additional potassium permanganate (2.3 g) is added gradually. After reacting for 5 hours, the produced manganese dioxide is removed by filtration. The filtrate is adjusted to pH 2-3 with diluted hydrochloric acid, and the resulting precipitate is separated by filtration, washed with water and dried to give the title compound (0.56 g).

m.p. >300° C.

NMR (DMSO-d$_6$) δ: 8.65 (s, 1H), 8.16 (s, 1H), 8.16 (d, J=8.57 Hz, 2H), 7.98 (d, J=8.57 Hz, 2H)

EXAMPLE 67

8-(3-Carboxyphenyl)-4-hydroxypyrazolo[1,5-a]-1,3,5-triazine

In the same manner as described in Example 66, the title compound is prepared.

m.p. >300° C.

NMR (DMSO-d$_6$) 4: 8.67 (bs, 1H), 8.63 (s, 1H), 8.20 (dt, J=7.69 and 1.53 Hz, 1H), 8.17 (s, 1H), 7.85 (dt, J=7.69 and 1.43 Hz, 1H), 7.54 (t, J=7.69 Hz, 1H)

EXAMPLE 68

4-Hydroxy-8-(4-methoxycarbonylphenyl)pyrazolo[1,5a]-1,3,5-triazine

A mixture of 8-(4-carboxyphenyl)-4-hydroxypyrazolo[1,5-a]-1,3,5-triazine (145 mg), conc. sulfuric acid (4 ml) and methanol (4 ml) is refluxed with stirring for 24 hours. After cooling the reaction mixture, the resulting precipitate is separated by filtration, washed with methanol and dried to give the title compound (74 mg).

m.p. >300° C. (decomp.)

NMR (DMSO-d$_6$) δ: 8.63 (s, 1H), 8.17 (d, J=8.24 Hz, 2H), 8.15 (s, 1H), 7.98 (d, J=8.24 Hz, 2H)

EXAMPLE 69

8-(4-Acetylphenyl)-4-hydroxypyrazolo[1,5-a]-1,3,5-triazine

To a suspension of 8-(4-ethylphenyl)-4-hydroxypyrazolo[1,5-a]-1,3,5-triazine (240 mg) in acetic acid (5 ml) are added chromium trioxide (500 mg) and water (1 ml), and the mixture is stirred at room temperature for 14 hours. To the reaction mixture is added water, and the insoluble material is separated by filtration, washed with water and dried to give the title compound (150 mg).

m.p. >300° C.

NMR (DMSO-d$_6$) δ: 8.68 (s, 1H), 8.19 (d, J=8.6 Hz, 2H), 8.18 (s, 1H), 7.99 (d, J=8.6 Hz, 2H), 2.58 (s, 3H)

EXAMPLE 70

8-(4-Benzoylphenyl)-4-hydroxypyrazolo[1,5-a]-1,3,5-triazine

A mixture of 8-(4-α,α-ethylenedioxybenzylphenyl)-4-hydroxypyrazolo[1,5-a]-1,3,5-triazine (0.20 g), conc. hydrochloric acid (0.5 ml), water (1 ml), methanol (4 ml) and acetone (1 ml) is stirred at 45°-60° C. for 2 hours. After cooling, the resulting precipitate is separated by filtration, washed with water and dried to give the title compound (0.15 g).

m.p. >300° C.

NMR (DMSO-d$_6$) δ: 8.67 (s, 1H), 8.22 (d, J=8.35 Hz, 2H), 8.17 (s, 1H), 7.5-8.0 (m, 7H)

EXAMPLE 71

8-[4-(4-Benzyloxy-3,5-dibromobenzoyl)phenyl)-4-hydroxypyrazolo[1,5-a]-1,3,5-triazine An ethylene ketal derivative of the title compound is prepared in the same manner as described in Example 1, and it is treated in the same manner as described in Example 70 to give the title compound.

m.p. 273°-274° C.

NMR (DMSO-d$_6$) δ: 8.71 (s, 1H), 8.25 (d, J=8.6 Hz, 2H), 8.19 (s, 1H), 7.98 (s, 2H), 7.84 (d, J=8.6 Hz, 2H), 7.39-7.62 (m, 5H), 5.10 (s, 2H)

EXAMPLE 72

4-Hydroxy-8-(4-nitrophenyl)pyrazolo[1,5-a]-1,3,5-triazine

To a mixture of conc. sulfuric acid (0.5 ml), conc. nitric acid (0.5 ml) and acetic acid (2 ml) is addded 4-hydroxy-8-phenylpyrazolo[1,5-a]-1,3,5-triazine (310 mg), and the mixture is stirred at 50°-60° C. After reacting for one hour, to the reaction mixture is added water. The insoluble material is separated by filtration, washed with water and hot methanol and dried to give the title compound (210 mg).

m.p. >300° C.

NMR (DMSO-d$_6$) δ: 8.75 (s, 1H), 8.30 (s, 4H), 8.23 (s, 1H)

In the same manner as described in Example 72 by using appropriate startaing materials, there are prepared the compounds of Examples 73 to 76.

EXAMPLE 73

4-Hydroxy-8-(3-methyl-4-nitrophenyl)pyrazolo[1,5-a]-1,3,5-triazine m.p. 280° C. (sublimation)

NMR (DMSO-d$_6$) δ: 8.73 (s, 1H), 8.22 (s, 1H), 8.12 (d, J=1.5 Hz, 3H), 2.60 (s, 3H)

EXAMPLE 74

4-Hydroxy-8-(3-methoxy-4-nitrophenyl)pyrazolo[1,5-a]-1,3,5-triazine m.p. >300° C.

NMR (DMSO-d$_6$) δ: 8.79 (s, 1H), 8.22 (s, 1H), 7.99 (d, J=8.8 Hz, 1H), 7.93 (d, J=1.7 Hz, 1H), 7.83 (dd, J=8.8 and 1.5 Hz, 1H), 4.01 (s, 3H)

EXAMPLE 75

8-(3-Chloro-4-nitrophenyl)-4-hydroxypyrazolo[1,5-a]-1,3,5-triazine m.p. 265° C. (sublimation)

NMR (DMSO-d$_6$) δ: 8.79 (s, 1H), 8.44 (d, J=1.3 Hz, 1H), 8.26 (s, 1H), 8.19 (s, 2H)

EXAMPLE 76

8-(3,5-Dimethyl-4-nitrophenyl)-4-hydroxypyrazolo[1,5-a]-1,3,5-triazine m.p. 270° C. (sublimation)

NMR (DMSO-d$_6$) δ: 8.64 (s, 1H), 8.18 (s, 1H), 7.95 (s, 2H), 2.31 (s, 6H)

EXAMPLE 77

8-(4-Aminophenyl)-4-hydroxypyrazolo[1,5-a]-1,3,5-triazine

4-Hydroxy-8-(4-nitrophenyl)pyrazolo[1,5-a]-1,3,5-triazine (660 mg) and 5% palladium-carbon (500 mg) are suspended in 80% aqueous methanol (100 ml), and the mixture is stirred under hydrogen atmosphere at room temperature. After reacting for 46 hours, to the reaction mixture is added conc. hydrochloric acid (5 ml), and the insoluble material is removed off by filtration. The filtrate is concentrated to driness under reduced pressure to give the title compound (450 mg).

m.p. >300° C.

NMR (DMSO-d$_6$) δ: 8.59 (s, 1H), 8.13 (s, 1H), 8.09 2 (d, J=8.6 Hz, 2H), 7.39 (d, J=8.6 Hz, 2H)

EXAMPLE 78

4-Hydroxy-8-[2-(5-nitrothienyl)]pyrazolo[1,5-a]-1,3,5-triazine

To a mixture of conc. sulfuric acid (0.2 ml), conc. nitric acid (0.2 ml) and acetic acid (3 ml) is added 4-hyroxy-8-(thienyl)pyrazolo[1,5-a]-1,3,5-triazine (440 mg) under ice cooling, and the mixture is sitrred at room temperature. After reacting for 3 hours, to the reaction mixture is added water. The insoluble material is separated by filtration, washed with hot methanol and dried to give the title compound (190 mg).

m.p. 250° C. (sublimation)

NMR (DMSO-d$_6$) δ: 8.72 (s, 1H), 8.28 (s, 1H), 8.13 (d, J=4.4 Hz, 1H), 7.63 (d, J=4.4 Hz, 1H)

EXAMPLE 79

4-Hydroxy-8-[3-(2-nitrothienyl)]pyrazolo[1,5-a]-1,3,5-triazine

In the same manner as described in Example 78 by using an appropriate starting material, the title compound is prepared.

m.p. >300° C.

NMR (DMSO-d$_6$) δ: 8.51 (s, 1H), 8.15 (s, 1H), 8.02 (d, J=5.5 Hz, 1H), 7.55 (d, J=5.5 Hz, 1H)

EXAMPLE 80

4-Hydroxy-8-(2-hydroxyphenyl)pyrazolo[1,5-a]-1,3,5-triazine

A mixture of 4-hydroxy-8-(2-methoxyphenyl)-pyrazolo[1,5-a]-1,3,5-triazine (242 mg), aluminum chloride (799 mg) and nitrobenzene (3 ml) is stirred at 80°–90° C. for 5 hours. The reaction mixture is cooled and poured into ice water. The precipitate is separated by filtration, washed with water and dried to give the title compound (140 mg).

m.p. 293°–297° C. (decomp.)

NMR (DMSO-d$_6$) δ: 9.85 (s, 1H), 8.55 (s, 1H), 8.07 (s, 1H), 7.97–8.07 (dd, J=1.98 Hz, 1H), 6.76–7.14 (m, 3H)

In the same manner as described in Example 80 by using appropriate starting materials, there are prepared the compounds of Examples 81 to 83.

EXAMPLE 81

4-Hydroxy-8-(3-hydroxyphenyl)pyrazolo[1,5-a]-1,3,5-triazine m.p. 262°–266° C. (decomp.)

NMR (DMSO-d$_6$) δ: 8.46 (s, 1H), 8.08 (s, 1H), 7.44–7.49 (m, 1H), 7.35 (bs, 1H), 7.19 (t, J=7.58 Hz, 1H), 6.67 (dd, J=7.69 and 1.32 Hz, 1H)

EXAMPLE 82

4-Hydroxy-8-(4-hydroxyphenyl)pyrazolo[1,5-a]-1,3,5-triazine m.p. >300° C.

NMR (DMSO-d$_6$) δ: 8.43 (s, 1H), 8.03 (s, 1H), 7.80 (d, J=8.57 Hz, 2H), 6.81 (d, J=8.57 Hz, 2H)

EXAMPLE 83

8-(4-Bromo-3-hydroxyphenyl)-4-hydroxypyrazolo[1,5-a]-1.3,5-triazine m.p. 277°–279° C. (decomp.)

NMR (DMSO-d$_6$) δ: 10.23 (s, 1H), 8.45 (s, 1H), 8.10 (s, 1H), 7.69 (d, J=1.87 Hz, 1H), 7.49 (d, J=8.13 Hz, 1H), 7.33 (dd, J=8.13 and 1.75 Hz, 1H)

EXAMPLE 84

8-(3,5-Dichloro-4-hydroxyphenyl)-4-hydroxypyrazolo[1,5-a]-1,3,5-triazine

In the same manner as described in Example 80, 8-(4-benzyloxy-3,5-dichlorophenyl)-4-hydroxypyrazolo[1,5-a]-1,3,5-triazine is reacted at room temperature for one hour to give the title compound.

m.p. >300° C.

NMR (DMSO-d$_6$) δ: 8.60 (s, 1H), 8.14 (s, 1H), 8.04 (s, 2H)

EXAMPLE 85

8-(3,5-Dibromo-4-hydroxyphenyl)-4-hydroxypyrazolo[1,5-a]-1,3,5-triazine

A benzyl derivative of the title compound is prepared in the same manner as described in Example 1, and it is treated in the same manner as described in Example 80 to give the title compound.

m.p. >300° C.

NMR (DMSO-$d_6$) δ: 8.63 (s, 1H), 8.24 (s, 2H), 8.15 (s, 1H)

EXAMPLE 86

8-(3,5-Dimethoxy-4-hydrpxyphenyl)-4-hydroxypyrazolo[1,5-a]-1,3,5-triazine

In the same manner as described in Example 80 by using an appropriate starting material, there is prepared the title compound.

m.p 250°–270° C. (decomp.)

NMR (DMSO-$d_6$) δ: 8.55 (s, 1H), 8.37 (bs, 1H), 8.07 (s, 1H), 7.31 (s, 2H), 3.79 (s, 6H)

EXAMPLE 87

8-(3-Acetoxyphenyl)-4-hydroxypyrazolo[1,5-a]-1,3,5-triazine

A mixture of 4-hydroxy-8-(3-methoxyphenyl)-pyrazolo[1,5-a]-1,3,5-triazine (242 mg), aluminum chloride (799 mg) and nitrobenzene (3 ml) is stirred at 80°–90° C. for 5 hours. To the reaction mixture is added acetyl chloride (0.12 ml). After reacting for 45 minutes, the reaction mixture is cooled and poured into ice water. The resulting precipitate is separated by filtration, washed with water and dried to give the title compound (8 mg).

m.p. 244°–249° C. (decomp.)

NMR (DMSO-$d_6$) δ: 8.58 (s, 1H), 8.13 (s, 1H), 7.79–7.96 (m, 2H), 7.45 (t, J=7.91 Hz, 1H), 7.01 (bd, J=7.91 Hz, 1H)

EXAMPLE 88

8-[4-(3,5-Dibromo-4-hydroxybenzoyl)phenyl]-4-hydroxypyrazolo[1,5-a]-1,3,5-triazine A benzyl derivative of the title compound is prepared in the same manner as described in Example 71 and it is treated in the same manner as described in Example 80 to give the title compound.

m.p. >300° C.

NMR (DMSO-$d_6$) δ: 8.70 (s, 1H), 8.23 (d, J=8.0 Hz, 2H), 8.19 (s, 1H), 7.88 (s, 2H), 7.79 (d, J=8.1 Hz, 2H)

EXAMPLE 89

4-Hydroxy-8-(4-methylsulfinylphenyl)pyrazolo[1,5-a]-1,3,5-triazine

To a suspension of 4-hydroxy-8-(4-methylthiophenyl)pyrazolo[1,5-a]-1,3,5-triazine (258 mg) and sodium metaperiodate (430 mg) in methanol (20 ml) is added water (0.5 ml), and the mixture is stirred at room temperature for 40 hours. The insoluble material is separated by filtration, washed with water and dried to give the title compound (180 mg).

m.p. 285°–286° C.

NMR (DMSO-$d_6$) δ: 8.66 (s, 1H), 8.22 (d, J=8.6 Hz, 2H), 8.16 (s, 1H), 7.73 (d, J=8.6 Hz, 2H), 2.76 (s, 3H)

EXAMPLE 90

4-Hydroxy-8-(3-methyl-4-methylsulfinylphenyl)-pyrazolo[1,5-a]-1,3,5-triazine

In the same manner as described in Example 89 by using an appropriate starting material, there is prepared the title compound.

m.p. 281°–282° C.

NMR (DMSO-$d_6$) δ: 8.64 (s, 1H), 8.16 (s, 1H), 8.13 (dd, J=8.2 and 1.6 Hz, 1H), 7.95 (d, J=1.6 Hz, 1H), 7.83 (d, J=8.2 Hz, 1H), 2.70 (s, 3H), 2.39 (s, 3H)

EXAMPLE 91

4-Hydroxy-8-(4-methanesulfonylphenyl)pyrazolo[1,5-a]-1,3,5-triazine

To a suspension of 4-hydroxy-8-(4-methylthiophenyl)pyrazolo[1,5-a]-1,3,5-triazine (260 mg) in acetic acid (5 ml) is added 35% hydrogen peroxide (3 ml), and the mixture is stirred at 70°–80° C. After reacting for one hour, to the reaction mixture is added water. The insoluble material is separated by filtration, washed with water and dried to give the title compound (250 mg).

m.p. >300° C.

NMR (DMSO-$d_6$) 4: 8.71 (s, 1H), 8.30 (d, J=8.6 Hz, 2H), 8.20 (s, 1H), 7.96 (d, J=8.6 Hz, 2H), 3.27 (s, 3H)

EXAMPLE 92

4-Hydroxy-8-[2-(5-phenylthiothienyl)]pyrazolo[1,5-a]-1,3,5-triazine

To a solution of thiophenol (130 ml) in N,N-dimethylformamide (2 ml) is added N-bromosuccinimide (160 mg), and the mixture is stirred at room temperature for 5 minutes. To the mixture is added 4-hydroxy-8-(2-thienyl)pyrazolo[1,5-a]-1,3,5-triazine (218 mg), and the mixture is stirred at room temperature for 2 hours. To the reaction mixture is added diethyl ether, and the resulting precipitate is separated by filtration, washed in order with ethanol, ethyl acetate and diethyl ether, and dried to give the title compound (120 mg).

m.p. 295°–298° C.

NMR (DMSO-$d_6$) δ: 8.54 (s, 1H), 8.12 (s, 1H), 7.56 (d, J=3.7 Hz, 1H), 7.40 (d, J=3.7 Hz, 1H), 7.19–7.35 (m, 5H)

EXAMPLE 93

4-Hydroxy-8-[4-(2-phenylthiothienyl)]pyrazolo[1,5-a]-1,3,5-triazine

In the same manner as described in Example 92 by using an appropriate starting material, there is prepared the title compound.

m.p. 278°–281° C.

NMR (DMSO-$d_6$) δ: 8.45 (s, 1H), 8.12 (s, 1H), 7.91 (s, 2H), 7.04–7.36 (m, 5H)

EXAMPLE 94

4-Hydroxy-8-(4-phenylaminosulfonylphenyl)-pyrazolo[1,5-a]-1,3,5-triazine

A mixture of 4-hydroxy-8-phenylpyrazolo[1,5-a]-1,3,5-triazine (420 mg) and chlorosulfonic acid (3 ml) is stirred at 80° C. After reacting for one hour, to the reaction mixture is added water. The resulting precipitate is separated by filtration, washed with water and dried. To the above precipitate is added aniline (10 ml), and the mixture is stirred at 80° C. for 2 hours. The reaction mixture is acidified by adding thereto 2N hydrochloric acid. The resulting precipitate is separated by filtration, washed with water and dried to give the title compound (420 mg).

m.p. 274°–277° C.

NMR (DMSO-$d_6$) δ: 10.21 (s, 1H), 8.62 (s, 1H), 8.17 (d, J=8.6 Hz, 2H), 8.16 (s, 1H), 7.78 (d, J=8.6 Hz, 2H), 6.92–7.34 (m, 5H)

In the same manner as described in Example 94 by using appropriate starting materials, there are prepared the compounds of Examples 95 to 140.

EXAMPLE 95

4-Hydroxy-8-[4-(4-methylphenylaminosulfonyl)-phenyl]pyrazolo[1,5-a]-1,3,5-triazine m.p. 262°–265° C.

NMR (DMSO-$d_6$) δ: 10.05 (s, 1H), 8.63 (s, 1H), 8.17 (d, J=8.6 Hz, 2H), 8.16 (s, 1H), 7.76 (d, J=8.6 Hz, 2H), 7.01 (s, 4H), 2.18 (s, 3H)

EXAMPLE 96

8-[4-(4-Ethylphenylaminosulfonyl)phenyl]-4-hydroxypyrazolo[1,5-a]-1,3,5-triazine m.p. 285°–290° C.

NMR (DMSO-$d_6$) δ: 10.09 (s, 1H), 8.63 (s, 1H), 8.17 (s, 1H), 8.17 (d, J=8.6 Hz, 2H), 7.78 (d, J=8.6 Hz, 2H), 7.04 (s, 4H), 2.25 (q, J=7.3 Hz, 2H), 1.17 (t, J=7.3 Hz, 3H)

EXAMPLE 97

8-[4-(3-Ethylphenylaminosulfonyl)phenyl]-4-hydroxypyrazolo[1,5-a]-1,3,5-triazine m.p. 240°–248° C.

NMR (DMSO-$d_6$) δ: 10.15 (s, 1H), 8.63 (s, 1H), 8.18 (d, J=8.6 Hz, 2H), 8.16 (s, 1H), 7.79 (d, J=8.6 Hz, 2H), 6.70–7.50 (m, 4H), 2.20–2.60 (m, 2H), 1.08 (t, J=7.2 Hz, 3H)

EXAMPLE 98

8-[4-(2-Ethylphenylaminosulfonyl)phenyl]-4-hydroxypyrazolo[1,5-a]-1,3,5-triazine m.p. 250°–254° C.

NMR (DMSO-$d_6$) δ: 9.51 (s, 1H), 8.67 (s, 1H), 8.21 (d, J=8.6 Hz, 2H), 8.18 (s, 1H), 7.71 (d, J=8.6 Hz, 2H), 7.07–7.25 (m, 4H), 2.46–2.57 (m, 2H), 0.97 (t, J=7.7 Hz, 3H)

EXAMPLE 99

4-Hydroxy-8-[4-(4-isopropylphenylaminosulfonyl)-phenyl]pyrazolo[1,5-a]-1,3,5-triazine m.p. 290°–295° C.

NMR (DMSO-$d_6$) δ: 10.10 (s, 1H), 8.63 (s, 1H), 8.18 (d, J=8.6 Hz, 2H), 8.16 (s, 1H), 7.78 (d, J=8.6 Hz, 2H), 7.00–7.20 (m, 4H), 2.46–2.52 (m, 1H), 1.11 (d, J=6.8 Hz, 6H)

EXAMPLE 100

8-[4-(4-t-Butylphenylaminosulfonyl)phenyl]-4hydroxypyrazolo[1,5-a]-1,3,5-triazine m.p. 275°–279° C.

NMR (DMSO-$d_6$) δ: 10.13 (s, 1H), 8.63 (s, 1H), 8.18 (d, J=8.6 Hz, 2H), 8.17 (s, 1H), 7.80 (d, J=8.6 Hz, 2H), 7.25 (d, J=8.8 Hz, 2H), 7.02 (d, J=8.8 Hz, 2H), 1.19 (s, 9H)

EXAMPLE 101

4-Hydroxy-8-[4-(4-α-hydroxyethylphenylaminosulfonyl)phenyl]pyrazolo[1,5-a]-1,3,5-triazine m.p 236°–239° C.

NMR (DMSO-$d_6$) δ: 8.54 (s, 1H), 8.18 (d, J=8.6 Hz, 2H), 8.12 (s, 1H), 7.78 (d, J=8.6 Hz, 2H), 7.21 (d, J=8.6 Hz, 2H), 7.06 (d, J=8.6 Hz, 2H), 4.61 (q, J=6.6 Hz, 1H), 1.24 (d, J=6.4 Hz, 3H)

EXAMPLE 102

8-[4-(4-Acetylphenylaminosulfonyl)phenyl]-4hydroxypyrazolo[1,5-a]-1,3,5-triazine m.p. 260°–262° C.

NMR (DMSO-$d_6$) δ: 10.82 (s, 1H), 8.63 (s, 1H), 8.21 (d, J=8.8 Hz, 2H), 8.16 (s, 1H), 7.88 (d, J=8.8 Hz, 2H), 7.84 (d, J=8.8 Hz, 2H), 7.24 (d, J=8.8 Hz, 2H), 3.42 (s, 3H)

EXAMPLE 103

8-[4-(4-Cyanophenylaminosulfonyl)phenyl]-4-hydroxypyrazolo[1,5-a]-1,3,5-triazine m.p. 272°–274° C.

NMR (DMSO-$d_6$) 4: 11.01 (s, 1H), 8.64 (s, 1H), 8.22 (d, J=8.6 Hz, 2H), 8.18 (s, 1H), 7.88 (d, J=8.6 Hz, 2H), 7.70 (d, J=9.0 Hz, 2H), 7.28 (d, J=9.0 Hz, 2H)

EXAMPLE 104

[4-(4-Carboxyphenylaminosulfonyl)phenyl]-4hydroxypyrazolo[1,5-a]-1,3,5-triazine m.p. 200°–202° C.

NMR (DMSO-$d_6$) δ: 10.75 (s, 1H), 8.62 (s, 1H), 8.20 (d, J=8.6 Hz, 2H), 8.15 (s, 1H), 7.86 (d, J=8.6 Hz, 2H), 7.80 (d, J=8.6 Hz, 2H), 7.22 (d, J=8.8 Hz, 2H)

EXAMPLE 105

4-Hydroxy-8-[4-(4-methoxycarbonylphenylaminosulfonyl)phenyl]pyrazolo[1,5-a]-1,3,5-triazine m.p. 241°–243° C.

NMR (DMSO-$d_6$) 4: 10.81 (s, 1H), 8.63 (s, 1H), 8.21 (d, J=8.8 Hz, 2H), 8.17 (s, 1H), 7.86 (d, J=8.8 Hz, 2H), 7.83 (d, J=8.8 Hz, 2H), 7.25 (d, J=8.8 Hz, 2H), 3.78 (s, 3H)

EXAMPLE 106

4-Hydroxy-8-[4-(4-hydroxyphenylaminosulfonyl)-phenyl]pyrazolo[1,5-a]-1,3,5-triazine m.p. 175°–177° C.

NMR (DMSO-$d_6$) δ: 9.69 (s, 1H), 8.63 (s, 1H), 8.17 (s, 1H), 8.16 (d, J=8.6 Hz, 2H), 7.70 (d, J=8.6 Hz, 2H), 6.89 (d, J=9.0 Hz, 2H), 6.61 (d, J=9.0 Hz, 2H)

EXAMPLE 107

4-Hydroxy-8-[4-(3-hydroxyphenylaminosulfonyl)-phenyl]pyrazolo[1,5-a]-1,3,5-triazine m.p. 166°–169° C.

NMR (DMSO-$d_6$) : 10.10 (s, 1H), 8.64 (s, 1H), 8.18 (d, J=8.6 Hz, 2H), 8.16 (s, 1H), 7.79 (d, J=8.6 Hz, 2H), 6.90 (t, J=8.4 Hz, 1H), 6.37–6.61 (m, 3H)

EXAMPLE 108

4-Hydroxy-8-[4-(3,4,5-trimethoxyphenylaminosulfonyl)phenyl]pyrazolo[1,5-a]-1,3,5-triazine m.p. 280°–282° C.

NMR (DMSO-d$_6$) 4: 10.06 (s, 1H), 8.64 (s, 1H), 8.20 (d, J=8.6 Hz, 2H), 8.16 (s, 1H), 7.82 (d, J=8.6 Hz, 2H), 6.42 (s, 2H), 3.65 (s, 6H), 3.56 (s, 3H)

EXAMPLE 109

8-[4-(4-Chlorophenylaminosulfonyl)phenyl]-4hydroxypyrazolo[1,5-a]-1,3,5-triazine m.p. 189°–193° C.

NMR (DMSO-d$_6$) δ: 10.38 (s, 1H), 8.64 (s, 1H), 8.20 (d, J=8.6 Hz, 2H), 8.17 (s, 1H), 7.79 (d, J=8.6 Hz, 2H), 7.31 (d, J=9.0 Hz, 2H), 7.12 (d, J=9.0 Hz, 2H)

EXAMPLE 110

4-Hydroxy-8-[4-(3,4,5-trichlorophenylaminosulfonyl)-phenyl]pyrazolo[1,5-a]-1,3,5-triazine m.p. 280°–283° C.

NMR (DMSO-d$_6$) δ: 10.91 (bs, 1H), 8.66 (s, 1H), 8.25 (d, J=8.8 Hz, 2H), 8.19 (s, 1H), 7.87 (d, J=8.8 Hz, 2H), 7.32 (s, 2H)

EXAMPLE 111

8-[4-(4-Carboxy-3-hydroxyphenylaminosulfonyl)-phenyl]-4-hydroxypyrazolo[1,5-a]-1,3,5-triazine m.p. 213°–216° C.

NMR (DMSO-d$_6$) δ: 10.81 (s, 1H), 8.65 (s, 1H), 8.23 (d, J=8.6 Hz, 2H), 8.18 (s, 1H), 7.89 (d, J=8.6 Hz, 2H), 7.65 (d, J=9.2 Hz, 1H), 6.67–6.77 (m, 2H)

EXAMPLE 112

4-Hydroxy-8-4-(3-hydroxy-4-methoxycarbonyl-phenylaminosulfonyl)phenyl]pyrazolo[1,5-a]-1,3,5-triazine m.p. 269°–273° C.

NMR (DMSO-d$_6$) δ: 10.84 (bs, 1H), 10.55 (bs, 1H), 8.64 (s, 1H), 8.22 (d, J=8.6 Hz, 2H), 8.18 (s, 1H), 7.88 (d, J=8.6 Hz, 2H), 7.64 (d, J=9.0 Hz, 1H), 6.69–6.79 (m, 2H), 3.81 (s, 3H)

EXAMPLE 113

4-Hydroxy-8-[4-(3-methoxy-4-methoxycarbonyl-phenylaminosulfonyl)phenyl]pyrazolo[1,5-a]-1,3,5-triazine m.p. 160°–163° C.

NMR (DMSO-d$_6$) δ: 10.73 (s, 1H), 8.64 (s, 1H), 8.22 (d, J=8.8 Hz, 2H), 8.17 (s, 1H), 7.89 (d, J=8.8 Hz, 2H), 7.58 (d, J=8.4 Hz, 1H), 6.90 (d, J=1.8 Hz, 1H), 6.79 (dd, J=8.4 and 1.8 Hz, 1H), 3.74 (s, 3H), 3.71 (s, 3H)

EXAMPLE 114

4-Hydroxy-8-[4-(3-pyridylaminosulfonyl)phenyl]-pyrazolo[1,5-a]-1,3,5-triazine m.p.>300° C.

NMR (DMSO-d$_6$) δ: 8.64 (s, 1H), 8.20 (d, J=8.6 Hz, 2H), 8.17 (s, 1H), 8.14–8.33 (m, 2H), 7.30–7.50 (m, 4H)

EXAMPLE 115

4-Hydroxy-8-[4-(pyrimidin-2-ylaminosulfonyl)phenyl]-pyrazolo[1,5-a]-1,3,5-triazine m.p. 267°–269° C.

NMR (DMSO-d$_6$) δ: 8.66 (s, 1H), 8.52 (d, J=4.8 Hz, 8.23 (d, J=8.8 Hz, 2H), 8.19 (s, 1H), 8.03 (d, J=8.8 Hz, 2H), 7.05 (t, J=4.8 Hz, 1H)

EXAMPLE 116

4-Hydroxy-8-[4-(thiazol-2-ylaminosulfonyl)phenyl]-pyrazolo[1,5-a]-1,3,5-triazine m.p 242°–245° C.

NMR (DMSO-d$_6$) δ: 8.64 (s, 1H), 8.18 (d, J=8.6 Hz, 2H), 8.17 (s, 1H), 7.84 (d, J=8.6 Hz, 2H), 7.24 (d, J=4.6 Hz, 1H), 6.82 (d, J=4.6 Hz, 1H)

EXAMPLE 117

4-Hydroxy-8-[4-(5-methylisoxazol-3-ylaminosulfonyl)-phenyl]pyrazolo[1,5-a]-1,3,5-triazine m.p. 273° C. (decomp.)

NMR (DMSO-d$_6$) δ: 11.40 (bs, 1H), 8.67 (s, 1H), 8.24 (d, J=8.8 Hz, 2H), 8.19 (s, 1H), 7.89 (d, J=8.8 Hz, 2H), 6.16 (d, J=0.9 Hz, 1H), 2.30 (d, J=0.9 Hz, 3H)

EXAMPLE 118

4-Hydroxy-8-[4-(pyrazol-3-ylaminosulfonyl)phenyl]-pyrazolo[1,5-a]-1,3,5-triazine m.p.>300° C.

NMR (DMSO-d$_6$) δ: 8.63 (s, 1H), 8.18 (d, J=8.6 Hz, H), 8.16 (s, 1H), 7.80 (d, J=8.6 Hz, 2H), 7.52 (d, J=2.4 Hz, 1H), 5.97 (d, J=2.2 Hz, 1H)

EXAMPLE 119

8-[4-(3-aminopyrazol-2-ylsulfonyl)phenyl]-4-hydroxypyrazolo[1,5-a]-1,3,5-triazine m.p. 190°–194° C.

NMR (DMSO-d$_6$) δ: 8.67 (s, 1H), 8.24 (d, J=8.4 Hz, 2H), 8.20 (s, 1H), 8.00 (d, J=2.8 Hz, 1H), 7.86 (d, J=8.8 Hz, 2H), 5.88 (d, J=2.8 Hz, 1H)

EXAMPLE 120

8-[4-(3-Acetylaminopyrazol-2-ylsulfonyl)phenyl]-4hydroxypyrazolo[1,5-a]-1,3,5-triazine m.p. 239°–242° C.

NMR (DMSO-d$_6$) δ: 10.89 (s, 1H), 8.69 (s, 1H), 8.53 2(d, J=2.9 Hz, 1H), 8.29 (d, J=8.6 Hz, 2H), 8.21 (s, 1H), 7.9 (d, J=8.6 Hz, 2H), 6.86 (d, J=2.9 Hz, 1H), 1.98 (s, 3H)

EXAMPLE 121

4-Hydroxy-8-(4-N-methyl-phenylaminosulfonyl-phenyl)pyrazolo[1,5-a]-1,3,5-triazine m.p. 252°–255° C.

NMR (DMSO-d$_6$) δ: 8.68 (s, 1H), 8.22 (d, J=8.6 Hz, 2H), 8.19 (s, 1H), 7.54 (d, J=8.6 Hz, 2H), 7.10–7.40 (m, 5H), 3.17 (s, 3H)

EXAMPLE 122

8-(4-Dimethylaminosulfonylphenyl)-4-hydroxypyrazolo[1,5-a]-1,3,5-triazine m.p. 283°–284° C.

NMR (DMSO-d$_6$) δ: 8.70 (s, 1H), 8.29 (d, J=8.6 Hz, 2H), 8.20 (s, 1H), 7.79 (d, J=8.6 Hz, 2H), 2.64 (s, 6H)

EXAMPLE 123

8-(4-Di-n-butylaminosulfonylphenyl)-4-hydroxypyrazolo[1,5-a]-1,3,5-triazine m.p. 136°–140° C.

NMR (DMSO-d$_6$) δ: 8.51 (s, 1H), 8.26 (d, J=8.6 Hz, 2H), 8.08 (s, 1H), 7.77 (d, J=8.6 Hz, 2H), 2.80–3.10 (m, 4H), 0.95–1.61 (m, 8H), 0.78–0.95 (m, 6H)

EXAMPLE 124

4-Hydroxy-8-(4-piperidinosulfonylphenyl)-pyrazolo[1,5-a]-1,3,5-triazine m.p. >300° C.

NMR (DMSO-d$_6$) δ: 8.61 (s, 1H), 8.28 (d, J=8.6 Hz, 2H), 8.14 (s, 1H), 7.74 (d, J=8.6 Hz, 2H), 2.50–3.10 (m, 4H), 1.00–1.80 (m, 6H)

EXAMPLE 125

4-Hydroxy-8-(4-pyrrolidinosulfonylphenyl)-pyrazolo[1,5-a]-1,3,5-triazine m.p. >300° C.

NMR (DMSO-d$_6$) δ: 8.69 (s, 1H), 8.27 (d, J=8.6 Hz, 2H), 8.19 (s, 1H), 7.84 (d, J=8.6 Hz, 2H), 3.10–3.24 (m, 4H), 1.59–1.73 (m, 4H)

EXAMPLE 126

4-Hydroxy-8-(4-morpholinosulfonylphenyl)-pyrazolo[1,5-a]-1,3,5-triazine m.p. >300° C.

NMR (DMSO-d$_6$) δ: 8.71 (s, 1H), 8.31 (d, J=8.6 Hz, 2H), 8.20 (s, 1H), 7.78 (d, J=8.6 Hz, 2H), 3.59–3.64 (m, 4H), 2.90–3.00 (m, 4H)

EXAMPLE 127

4-Hydroxy-8-(4-methylaminosulfonylphenyl)-pyrazolo[1,5-a]-1,3,5-triazine m.p 296°–298° C.

NMR (DMSO-d$_6$) δ: 8.68 (s, 1H), 8.24 (d, J=8.4 Hz, 2H), 8.19 (s, 1H), 7.82 (d, J=8.4 Hz, 2H), 7.39 (q, J=5.1 Hz, 1H), 2.44 (d, J=4.8 Hz, 3H)

EXAMPLE 128

8-(4-Aminosulfonylphenyl)-4-hydroxypyrazolo[1,5-a]-1,3,5-triazine m.p. 297°–300° C.

NMR (DMSO-d$_6$) δ: 8.67 (s, 1H), 8.22 (d, J=8.6 Hz, 2H), 8.17 (s, 1H), 7.86 (d, J=8.6 Hz, 2H), 7.31 (s, 2H)

EXAMPLE 129

8-(4-Cyclohexylaminosulfonylphenyl)-4-hydroxypyrazolo[1,5-a]-1,3,5-triazine m.p. >300° C.

NMR (DMSO-d$_6$) δ: 8.68 (s, 1H), 8.23 (d, J=8.6 Hz, 2H), 8.18 (s, 1H), 7.86 (d, J=8.6 Hz, 2H), 7.59 (d, J=7.0 Hz, 1H), 2.70–3.00 (m, 1H), 1.00–1.62 (m, 10H)

EXAMPLE 130

4-Hydroxy-8-(4-tetrahydrofurfurylaminosulfonylphenyl)pyrazolo[1,5-a]-1,3,5-triazine m.p. 258°–262° C.

NMR (DMSO-d$_6$) δ: 8.68 (s, 1H), 8.24 (d, J=8.6 Hz, 2H), 8.19 (s, 1H), 7.84 (d, J=8.6 Hz, 2H), 7.80–8.06 (m, 1H), 3.60–3.80 (m, 3H), 2.51 (t, J=2.0 Hz, 2H), 1.68–1.82 (m, 4H)

EXAMPLE 131

4-Hydroxy-8-(4-β-hydroxyethylaminosulfonylphenyl)-pyrazolo[1,5-a]-1,3,5-triazine m.p. 268°–270° C.

NMR (DMSO-d$_6$) δ: 8.68 (s, 1H), 8.24 (d, J=8.6 Hz, 2H), 8.19 (s, 1H), 7.84 (d, J=8.6 Hz, 2H), 7.54 (t, J=6.1 Hz, 1H), 3.38 (t, J=6.8 Hz, 2H), 2.70–3.00 (m, 2H)

EXAMPLE 132

8-(4-Benzylaminosulfonylphenyl)-4-hydroxypyrazolo[1,5-a]-1,3,5-triazine m.p. 283°–286° C.

NMR (DMSO-d$_6$) δ: 8.68 (s, 1H), 8.23 (d, J=8.6 Hz, 2H), 8.19 (s, 1H), 8.10 (t, J=6.4 Hz, 1H), 7.85 (d, J=8.6 Hz, 2H), 7.26 (s, 5H), 4.02 (d, J=6.4 Hz, 2H)

EXAMPLE 133

8-(4-Furfurylaminosulfonylphenyl)-4-hydroxypyrazolo[1,5-a]-1,3,5-triazine m.p. 214° C. (decomp.)

NMR (DMSO-d$_6$) δ: 8.68 (s, 1H), 8.22 (d, J=8.6 Hz, 2H), 8.19 (s, 1H), 8.12 (t, J=5.9 Hz, 1H), 7.82 (d, J=8.6 Hz, 2H), 7.48 (dd, J=2.0 and 0.9 Hz, 1H), 6.31 (dd, J=3.3 and 2.0 Hz, 1H), 6.19 (dd, J=3.1 and 0.7 Hz, 1H), 4.04 (d, J=5.9 Hz, 2H)

EXAMPLE 134

4-Hydroxy-8-[4-(2-thienylmethylaminosulfonyl)-phenyl]pyrazolo[1,5-a]-1,3,5-triazine m.p. 240°–245° C.

NMR (DMSO-d$_6$) δ: 8.69 (s, 1H), 8.24 (d, J=8.6 Hz, 2H), 8.23 (t, J=5.9 Hz, 1H), 8.19 (s, 1H), 7.84 (d, J=8.6 Hz, 2H), 7.38 (dd, J=4.0 and 2.4 Hz, 1H), 6.92 (d, J=4.2 Hz, 1H), 6.90 (t, J=2.4 Hz, 1H), 4.21 (d, J=5.9 Hz, 2H)

EXAMPLE 135

8-(2-Dimethylaminosulfonyl-5-methoxyphenyl)-4-hydroxypyrazolo[1,5-a]-1,3,5-triazine m p. 246°–248° C.

NMR (DMSO-d$_6$) δ: 8.15 (s, 1H), 8.02 (s, 1H), 7.89 (d, J=8.8 Hz, 1H), 7.14 (dd, J=8.8 and 2.6 Hz, 1H), 7.04 (d, J=2.6 Hz, 1H), 3.85 (s, 3H), 2.40 (s, 6H)

EXAMPLE 136

8-(3-Chloro-4-dimethylaminosulfonylphenyl)-4-hydroxypyrazolo[1,5-a]-1,3,5-triazine m.p. 291°–294° C.

NMR (DMSO-d$_6$) δ: 8.76 (s, 1H), 8.38 (d, J=1.5 Hz, 1H), 8.24 (s, 1H), 8.19 (dd, J=8.4 and 1.5 Hz, 1H), 7.97 (d, J=8.4 Hz, 1H), 2.82 (s, 6H)

EXAMPLE 137

8-(4-Aminosulfonyl-3-chlorophenyl)-4-hydroxypyrazolo[1,5-a]-1,3,5-triazine m.p. >300° C.

NMR (DMSO-d$_6$) 4 8.74 (s, 1H), 8.34 (d, J=1.3 Hz, 1H), 8.23 (s, 1H), 8.06 (dd, J=8.4 and 1.3 Hz, 1H), 7.99 (d, J=8.4 Hz, 1H), 7.55 (s, 2H)

EXAMPLE 138

8-(4-Dimethylaminosulfonyl-3-methylphenyl)-4hydroxypyrazolo[1,5-a]-1,3,5-triazine m.p. 256°–258° C.

NMR (DMSO-d$_6$) δ: 8.68 (s, 1H), 8.19 (s, 1H), 8.05–8.13 (m, 2H), 7.80 (d, J=8.8 Hz, 1H), 2.74 (s, 6H), 2.50 (s, 3H)

EXAMPLE 139

4-Hydroxy-8-[4-(4-t-butylphenylaminosulfonyl)-3-methylphenyl]pyrazolo[1,5-a]-1,3,5-triazine m.p. 258°–260° C.

NMR (DMSO-d$_6$) δ: 10.24 (s, 1H), 8.63 (s, 1H), 8.17 (s, 1H), 7.99 (bs, 3H), 7.23 (d, J=8.8 Hz, 2H), 7.00 (d, J=8.8 Hz, 2H), 2.50 (s, 3H), 1.18 (s, 9H)

EXAMPLE 140

8-(4-Chloro-3-dimethylaminosulfonylphenyl)-4-hydroxypyrazolo[1,5-a]-1,3,5-triazine m.p. 294°–299° C.

NMR (DMSO-d$_6$) δ: 8.70 (s, 2H), 8.23 (s, 1H), 8.20 (dd, J=8.6 and 2.2 Hz, 1H), 7.75 (d, J=8.6 Hz, 1H), 2.87 (s, 6H)

EXAMPLE 141

8-(4-Bromophenyl)-4-hydroxypyrazolo[1,5-a]-1,3,5-triazine

To a suspension of 4-hydroxy-8-phenylpyrazolo[1,5a]-1,3,5-triazine (420 mg) and aluminum chloride (1.6 g) in nitrobenzene (2 ml) is added bromine (0.5 ml), and the mixture is stirred at 60° C. After reacting for 15 hours, to the reaction mixture is added water. The resulting precipitate is separated by filtration, washed with hot methanol to give the title compound (340 mg). m.p.>300° C.

NMR (DMSO-d$_6$) δ: 8.60 (s, 1H), 8.13 (s, 1H), 8.00 (d, J=8.6 Hz, 2H), 7.61 (d, J=8.6 Hz, 2H)

In the same manner as described in Example 141 by using appropriate starting materials, there are prepared the compounds of Examples 142 to 147.

EXAMPLE 142

8-(4-Bromo-3-methylphenyl)-4-hydroxypyrazolo[1,5-a]-1,3,5-triazine m.p. >300° C.

NMR (DMSO-d$_6$) δ: 8.59 (s, 1H), 8.14 (s, 1H), 8.00 (d, J=1.5 Hz, 1H), 7.77 (dd, J=8.3 and 1.5 Hz, 1H), 7.61 (d, J=8.3 Hz, 1H), 2.39 (s, 3H)

EXAMPLE 143

8-(4-Bromo-3-chlorophenyl)-4-hydroxypyrazolo[1,5-a]-1,3,5-triazine m.p.>300° C.

NMR (DMSO-d$_6$) δ: 8.68 (s, 1H), 8.32 (d, J=1.8 Hz, 1H), 8.18 (s, 1H), 7.95 (dd, J=8.6 and 2.0 Hz, 1H), 7.79 (d, J=8.6 Hz, 1H)

EXAMPLE 144

8-(4-Bromo-3,5-dimethylphenyl)-4-hydroxypyrazolo[1,5-a]-1,3,5-triazine m.p.>300° C.

NMR (DMSO-d$_6$) δ: 8.57 (s, 1H), 8.14 (s, 1H), 7.84 (s, 2H), 2.41 (s, 6H)

EXAMPLE 145

8-(4-Bromo-3-methoxyphenyl)-4-hydroxypyrazolo[1,5-a]-1,3,5-triazine m.p. 288°–291° C. (decomp.)

NMR (DMSO-d$_6$) δ: 8.65 (s, 1H), 8.13 (s, 1H), 7.70 (s, 1H), 7.59 (s, 2H), 3.92 (s, 3H)

EXAMPLE 146

8-(3-Bromo-4-methylthiophenyl)-4-hydroxypyrazolo[1,5-a]-1,3,5-triazine m.p. 292°–293° C.

NMR (DMSO-d$_6$) δ: 8.63 (s, 1H), 8.31 (d, J=1.8 Hz, 1H), 8.15 (s, 1H), 8.02 (dd, J=8.4 and 2.0 Hz, 1H), 7.31 (d, J=8.4 Hz, 1H), 2.51 (s, 3H)

EXAMPLE 147

8-[4-(4-Bromophenylthio)-3-methylphenyl]-4hydroxypyrazolo[1,5-a]-1,3,5-triazine m.p.>300° C.

NMR (DMSO-d$_6$) δ: 8.61 (s, 1H), 8.14 (s, 1H), 8.03 (d, J=2.0 Hz, 1H), 7.93 (dd, J=8.1 and 2.0 Hz, 1H), 7.50 (d, J=8.8 Hz, 2H), 7.43 (d, J=8.1 Hz, 1H), 7.10 (d, J=8.6 Hz, H), 2.36 (s, 3H)

EXAMPLE 148

8-[2-(5-Bromothienyl)]-4-hydroxypyrazolo[1,5-a]-1,3,5-triazine

To a suspension of 4-hydroxy-8-(2-thienyl)-pyrazolo[1,5-a]-1,3,5-triazine (440 mg) in nitrobenzene (4 ml) is added bromine (0.11 ml) under ice cooling, and the mixture is stirred at room temperature for 30 minutes. To the reaction mixture is added diethyl ether, and the resulting precipitate is separated by filtration and recrystallized from N,N-dimethylformamide-methanol to give the title compound (280 mg).

m.p. 286° C. (decomp.)

NMR (DMSO-d$_6$) δ: 8.50 (s, 1H), 8.14 (s, 1H), 7.36 (d, J=3.8 Hz, 1H), 7.21 (d, J=3.8 Hz, 1H)

In the same manner as described in Example 148 by using appropriate starting materials, there are prepared he compounds of Examples 149 to 151.

EXAMPLE 149

8-[2-(4,5-Dibromothienyl)]-4-hydroxypyrazolo[1,5-a]-1,3,5-triazine m.p.>300° C.

NMR (DMSO-d$_6$) δ: 8.66 (s, 1H), 8.18 (s, 1H), 7.35 (s, 1H)

EXAMPLE 150

8-[3-(2-Bromothienyl)]-4-hydroxypyrazolo[1,5-a]-1,3,5-triazine m.p.>300° C.

NMR (DMSO-d$_6$) δ: 8.57 (s, 1H), 8.11 (s, 1H), 7.69 (d, J=5.7 Hz, 1H), 7.54 (d, J=5.7 Hz, 1H)

EXAMPLE 151

8-[3-(2,5-Dibromothienyl)]-4-hydroxypyrazolo[1,5-a]-1,3,5-triazine m.p.>300° C.

NMR (DMSO-d$_6$) δ: 8.57 (s, 1H), 8.14 (s, 1H), 7.68 (s, 1H)

EXAMPLE 152

4-Hydroxy-2-mercapto-8-phenylpyrazolo[1,5-a]-1,3,5-triazine

To a solution of N-carbethoxy-N'-[3-(4-phenyl)-pyrazolyl]thiourea (2.90 g) in methanol (90 ml) is added with stirring a solution of sodium hydroxide (1.80 g) in methanol (60 ml) under ice cooling. After reacting for 20 minutes, the reaction mixture is adjusted to pH 1–2 with conc. hydrochloric acid, and thereto is added water (100 ml), and the mixture is stirred for 30 minutes. The resulting precipitate is separated by filtration, washed with water and recrystallized from methanol to give the title compound (1.60 g).

m.p. 251° C.

NMR (DMSO-$d_6$) δ: 12.73 (bs, 1H), 8.13 (s, 1H), 7.33–7.52 (m, 5H)

In the same manner as described in Example 152 by using appropriate starting materials, there are prepared the compounds of Examples 153 to 155.

EXAMPLE 153

8-(3-Chlorophenyl)-4-hydroxy-2-mercaptopyrazolo[1,5-a]-1,3,5-triazine m.p. 221°–222° C.

NMR (DMSO-$d_6$) δ: 12.76 (bs, 1H), 8.14 (s, 1H), 7.31–7.57 (m, 4H)

EXAMPLE 154

8-(2,4-Difluorophenyl)-4-hydroxy-2-mercaptopyrazolo[1,5-a]-1,3,5-triazine m.p. 239° C.

NMR (DMSO-$d_6$) δ: 12.79 (bs, 1H), 8.03 (s, 1H), 7.00–7.67 (m, 3H)

EXAMPLE 155

4-Hydroxy-2-mercapto-8-(3-methyl-4-methylthiophenyl)pyrazolo[1,5-a]-1,3,5-triazine m.p. 226.5°–229° C. (decomp.)

NMR (DMSO-$d_6$) δ: 12.74 (bs, 1H), 8.08 (s, 1H), 7.15–7.39 (m, 3H), 2.48 (s, 3H), 2.30 (s, 3H)

EXAMPLE 156

2,4-Dihydroxy-8-phenylpyrazolo[1,5-a]-1,3,5-triazine

To a mixture of 4-hydroxy-2-mercapto-8-phenylpyrazolo[1,5-a]-1,3,5-triazine (130 mg), 0.25N sodium hydroxide solution (4 ml) and methanol (3 ml) is with stirring added 30% hydrogen peroxide (1 ml) under ice cooling. The mixture is reacted for one hour, and the reaction mixture is adjusted to pH 1–2 with conc. hydrochloric acid. The resulting precipitate is separated by filtration, washed with water and methanol and dried to give the title compound (25.8 mg).

NMR (DMSO-$d_6$) δ: 8.08 (s, 1H), 7.2–7.6 (m, 5H)

In the same manner as described in Example 156 by using appropriate starting materials, there are prepared the compounds of Examples 157 to 159.

EXAMPLE 157

8-(3-Chlorophenyl)-2,4-dihydroxypyrazolo[1,5-a]-1,3,5-triazine m.p. 246°–249° C.

NMR (DMSO-$d_6$) δ: 12.07 (bs, 1H), 11.75 (bs, 1H), 8.14 (s, 1H), 7.20–7.58 (m, 4H)

EXAMPLE 158

8-(2,4-Difluorophenyl)-2,4-dihydroxypyrazolo[1,5-a]-1,3,5-triazine m.p. 271°–272° C.

NMR (DMSO-$d_6$) 4: 11.77 (bs, 1H), 7.96 (s, H), 7.05–7.65 (m, 3H)

EXAMPLE 159

4-Hydroxy-2-mercapto-8-(3-methyl-4-methylsulfinylphenyl)pyrazolo[1,5-a]-1,3,5-triazine m.p. 275°–277.5° C.

NMR (DMSO-$d_6$) δ: 11.8 (bs, 1H), 8.19 (s, 1H), 7.90 (d, J=8.79 Hz, 1H), 7.56–7.63 (m, 2H), 3.18 (s, 3H), 2.68 (s, 3H)

EXAMPLE 160

4-Acetoxy-8-(3-methyl-4-methylthiophenyl)pyrazolo[1,5-a]-1,3,5-triazine

To a mixture of 4-hydroxy-8-(3-methyl-4-methylthiophenyl)pyrazolo[1,5-a]-1,3,5-triazine (0.100 g), triethylamine (0.1 ml) and methylene chloride (10 ml) is added dropwise acetyl chloride (0.1 ml) at room temperature. After reacting for 10 minutes, to the reaction mixture is added methylene chloride (90 ml). The mixture is washed with water (20 ml×3), dried over anhydrous sodium sulfate, and concentrated under reduced pressure to give the title compound (0.110 g).

m.p. 213° C.

NMR (CDCl$_3$) δ: 8.63 (s, 1H), 8.30 (s, 1H), 7.70 (bd, J=8.36 Hz, 1H), 7.65 (bs, 1H), 7.21 (d, J=8.79 Hz, 1H), 2.92 (s, 3H), 2.49 (s, 3H), 2.39 (s, 3H)

In the same manner as described in Example 1 by using appropriate starting materials, there are prepared the compounds of Examples 162 to 168.

EXAMPLE 162

4-Hydroxy-8-(4-phenylthiomethylphenyl)pyrazolo[1,5-a]-1,3,5-triazine m.p. >300° C.

NMR (DMSO-$d_6$) δ: 8.54 (s, 1H), 8.10 (s, 1H), 7.68 (d, J=8.3 Hz, 2H), 7.39 (d, J=8.3 Hz, 2H), 7.14–7.34 (m, 5H), 4.24 (s, 2H)

EXAMPLE 163

4-Hydroxy-8-(3-phenoxyphenyl)pyrazolo[1,5-a]-1,3,5-triazine m.p. 292°–293° C.

NMR (DMSO-$d_6$) δ: 8.59 (s, 1H), 8.10 (s, 1H), 7.7–7.8 (m, 2H), 7.3–7.5 (m, 3H), 6.8–7.2 (m, 4H)

EXAMPLE 164

4-Hydroxy-8-[3-methyl-4-(pyridin-2-ylthio)phenyl]pyrazolo[1,5-a]-1,3,5-triazine m.p. >300° C.

NMR (DMSO-$d_6$) δ: 8.64 (s, 1H), 8.38 (ddd, J=4.8, 2.0 and 1.0 Hz, 1H), 8.16 (s, 1H), 8.08 (d, J=1.7 Hz, 1H), 7.97 (dd, J=8.0 and 1.7 Hz, 1H), 7.61 (d, J=8.0 Hz, 1H), 7.61 (ddd, J=8.5, 8.1 and 2.0 Hz, 1H), 7.11 (ddd, J=8.5, 4.8 and 1.0 Hz, 1H), 6.84 (dt, J=8.1 and 1.0 Hz, 1H), 2.37 (s, 3H)

EXAMPLE 165

4-Hydroxy-8-(3-methoxy-4-methylthiophenyl)pyrazolo[1,5-a]-1,3,5-triazine m.p. 284°–285° C.

NMR (DMSO-$d_6$) δ: 8.61 (s, 1H), 8.11 (s, 1H), 7.66 (dd, J=8.13 and 1.54 Hz, 1H), 7.61 (bs, 1H), 7.18 (d, J=8.13 Hz, 1H), 3.89 (s, 3H), 2.40 (s, 3H)

EXAMPLE 166

4-Hydroxy-8-(3-methoxy-4-phenylthiophenyl)-pyrazolo[1,5-a]-1,3,5-triazine m.p. 247°–248° C.

NMR (DMSO-d$_6$) δ: 8.64 (s, 1H), 8.13 (s, 1H), 7.74 (d, J=1.75 Hz, 1H), 7.63 (dd, J=7.91 and 1.75 Hz, 1H), 7.22–7.35 (m, 5H), 7.15 (d, J=7.91 Hz, 1H)

EXAMPLE 167

8-(3-Chloro-4-phenylthiophenyl)-4-hydroxypyrazolo[1,5-a]-1,3,5-triazine m.p. 290°–293° C.

NMR (DMSO-d$_6$) δ: 8.62 (s, 1H), 8.27 (d, J=2.0 Hz, 1H), 8.15 (s, 1H), 7.92 (dd, J=8.4 and 2.0 Hz, 1H), 7.41 (s, 5H), 7.16 (d, J=8.4 Hz, 1H)

EXAMPLE 168

8-(2-Fluoro-3-methyl-4-methylthiophenyl)-4-hydroxypyrazolo[1,5-a]-1,3,5-triazine m.p.>300° C.

NMR (DMSO-d$_6$) δ: 8.33 (d, J=3.5 Hz, 1H), 8.12 (s, 1H), 7.99 (t, J=8.3 Hz, 1H), 7.14 (d, J=8.1 Hz, 1H), 2.51 (s, 3H), 2.23 (s, 3H)

In the same manner as described in Example 89 by using appropriate starting materials, there are prepared the compounds of Examples 169 to 173.

EXAMPLE 169

8-(2-Fluoro-5-methyl-4-methylsulfinylphenyl)-4-hydroxypyrazolo[1,5-a]-1,3,5-triazine m.p.>300° C.

NMR (DMSO-d$_6$) δ: 8.41 (d, J=3.5 Hz, 1H), 8.19 (s, 1H), 8.08 (d, J=7.5 Hz, 1H), 7.62 (d, J=10.5 Hz, 1H), 2.74 (s, 3H), 2.35 (s, 3H)

EXAMPLE 170

4-Hydroxy-8-(4-phenylsulfinylphenyl)pyrazolo[1,5-a]-1,3,5-triazine m.p. 290°–291° C. (decomp.)

NMR (DMSO-d$_6$) δ: 8.60 (s, 1H), 8.17 (d, J=8.57 Hz, 2H), 8.13 (s, 1H), 7.75 (d, J=8.57 Hz, 2H), 7.64–7.74 (m, 2H), 7.47–7.60 (m, 3H)

EXAMPLE 171

4-Hydroxy-8-(3-methyl-4-phenylsulfinylphenyl)-pyrazolo[1,5-a]-1,3,5-triazine m.p. 243°–245.5° C.

NMR (DMSO-d$_6$) δ: 8.60 (s, 1H), 8.14 (s, 1H), 8.11 (bd, J=8.35 Hz, 1H), 7.93 (bs, 1H), 7.84 (d, J=8.35 Hz, 1H), 7.47–7.67 (m, 5H)

EXAMPLE 172

4-Hydroxy-8-(3-methoxy-4-methylsulfinylphenyl)-pyrazolo[1,5-a]-1,3,5-triazine m.p. 259°–260° C.

NMR (DMSO-d$_6$) δ: 8.70 (s, 1H), 8.16 (s, 1H), 7.92 (bd, J=7.91 Hz, 1H), 7.75 (bs, 1H), 7.66 (d, J=8.13 Hz, 1H), 3.95 (s, 3H), 2.73 (s, 3H)

EXAMPLE 173

4-Hydroxy-8-(3-methoxy-4-phenylsulfinylphenyl)-pyrazolo[1,5-a]-1,3,5-triazine monohydrate m.p. 173°–175° C.

NMR (DMSO-d$_6$) δ: 8.66 (s, 1H), 8.15 (s, 1H), 7.45–7.95 (m, 8H), 3.88 (s, 3H)

The above monohydrate compound is dried at 80° C. for 12 hours to give the corresponding anhydrous compound, m.p. 258°–266° C. (decomp.)

In the same manner as described in Example 91 by using an appropriate starting material, there is prepared the compound of Example 174.

EXAMPLE 174

8-(2-Fluoro-5-methyl-4-methylsulfonylphenyl)-4-hydroxypyrazolo[1,5-a]-1,3,5-triazine m.p.>300° C.

NMR (DMSO-d$_6$) δ: 8.44 (d, J=3.7 Hz, 1H), 8.27 (d, J=7.0 Hz, 1H), 8.24 (s, 1H), 7.75 (d, J=10.0 Hz, 1H), 3.28 (s, 3H), 2.54 (s, 3H)

In the same manner as described in Example 141 by using appropriate starting materials, there are prepared the compounds of Examples 175 to 176.

EXAMPLE 175

8-[4-(3-Bromo-4-methoxyphenylthio)-3-methylphenyl]-4-hydroxypyrazolo[1,5-a]-1,3,5-triazine m.p. 280°–285° C.

NMR (DMSO-d$_6$) δ: 8.56 (s, 1H), 8.12 (s, 1H), 7.87 (d, J=1.6 Hz, 1H), 7.83 (dd, J=7.9 and 1.6 Hz, 1H), 7.48 (d, J=2.0 Hz, 1H), 7.32 (dd, J=8.4 and 2.2 Hz, 1H), 7.19 (d, J=8.1 Hz, 1H), 7.13 (d, J=8.5 Hz, 1H), 3.85 (s, 3H), 2.37 (s, 3H)

EXAMPLE 176

8-[4-(2,4-Dibromo-5-methoxyphenylthio)-3-methylphenyl]-4-hydroxypyrazolo[1,5-a]-1,3,5-triazine m.p.>300° C.

NMR (DMSO-d$_6$) δ: 8.64 (s, 1H), 8.15 (s, 1H), 8.12 (d, J=1.5 Hz, 1H), 8.00 (dd, J=8.1 and 1.5 Hz, 1H), 7.87 (s, 1H), 7.46 (d, J=7.9 Hz, 1H), 6.47 (s, 1H), 3.53 (s, 3H), 2.38 (s, 3H)

EXAMPLE 177

2,4-Dihydroxy-8-(2-fluoro-5-methyl-4-methylthiophenyl)pyrazolo[1,5-a]-1,3,5-triazine 3-Amino-4-(2-fluoro-5-methyl-4-methylthiophenyl)-pyrazole (2.74 g) is dissolved in pyridine (20 ml) and the mixture is cooled to 0° C. To the mixture is added N-(chlorocarbonyl)isocyanate (1.03 ml), and the mixture is stirred at room temperature for 4 hours. The reaction mixture is acidified by adding thereto 10% hydrochloric acid under ice cooling. The resulting precipitate is separated by filtration, washed with water and dried to give the title compound (3.4 g).

m.p. 250°–253° C.

NMR (DMSO-d$_6$) δ: 7.94 (d, J=1.3 Hz, 1H), 7.26 (d, J=7.9 Hz, 1H), 7.08 (d, J=11.5 Hz, 1H), 2.50 (s, 3H), 2.23 (s, 3H)

EXAMPLE 178

4-Hydroxy-8-3-methoxy-4-phenylsulfinylphenyl)pyrazolo[1,5-a]-1,3,5-triazine monohydrate To a suspension of 4-hydroxy-8-(3-methoxy-4-phenylthiophenyl)pyrazolo[1,5-a]-1,3,5-triazine (11.21 g) in acetic acid (384 ml) is added 30% hydrogen peroxide (10.24 ml) over a period of about 3.5 hours. The mixture is stirred at room temperature for 28 hours, and to the reaction mixture is added water (400 ml). The resulting precipitate is separated by filtration, washed with water and dried to give the title compound (11.31 g).

NMR (DMSO-d$_6$) δ: 8.66 (s, 1H), 8.15 (s, 1H), 7.45-7.95 (m, 8H), 3.88 (s, 3H)

The above monohydrate compound is dried at 80° C. under reduced pressure for 12 hours to give the corresponding anhydrous compound, m.p. 258°-266° C. (decomp.)

In the same manner as described in Example 1 by using an appropriate starting material, there is prepared the compound of Example 179.

EXAMPLE 179

8-(Dibenzothiophn-2-yl)-4-hydroxypyrazolo[1,5-a]-1,3,5-triazine m.p.>300° C.

NMR (DMSO-d$_6$) δ: 8.94 (d, J=1.1 Hz, 1H), 8.80 (s, 1H), 7.98-8.45 (m, 4H), 8.18 (s, 1H), 7.49-7.59 (m, 2H)

In the same manner as described in Example 178 by using an appropriate starting material, there is prepared the compound of Example 180.

EXAMPLE 180

4-Hydroxy-8-[3-methyl-4-(pyridin-2-ylsulfinyl)phenyl]-pyrazolo[1,5-a]-1,3,5-triazine m.p. 172°-174° C.

NMR (DMSO-d$_6$) δ: 8.58 (s, 1H), 8.55 (dt, J=4.83 and 1.10 Hz, 1H), 8.13 (s, 1H), 7.93-8.10 (m, 4H), 7.71 (d, J=8.13 Hz, 1H), 7.47 (ddd, J=6.59, 4.56 and 2.20 Hz, 1H), 2.61 (s, 3H)

In the same manner as described in Example 91 by using appropriate starting materials, there are prepared the compounds of Examples 181 to 184.

EXAMPLE 181

4-Hydroxy-8-(4-phenylsulfonylphenyl)pyrazolo[1,5-a]-1,3,5-triazine m.p.>300° C.

NMR (DMSO-d$_6$) δ: 8.66 (s, 1H), 8.26 (d, J=8.79 Hz, 2H), 8.18 (s, 1H), 7.99 (d, 2H), 7.92-8.01 (m, 2H), 7.59-7.71 (m, 3H)

EXAMPLE 182

4-Hydroxy-8-(3-methyl-4-phenylsulfonylphenyl)-pyrazolo[1,5-a]-1,3,5-triazine m.p. 297°-298° C. (decomp.)

NMR (DMSO-d$_6$) δ: 8.66 (s, 1H), 8.18 (s, 1H), 8.17 (s, 1H), 8.16 (s, 1H), 8.02 (bs, 1H), 7.82-7.93 (m, 2H), 7.60-7.73 (m, 3H)

EXAMPLE 183

4-Hydroxy-8-(3-methoxy-4-phenylsulfonylphenyl)-pyrazolo[1,5-a]-1,3,5-triazine m.p 286°-287° C.

NMR (DMSO-d$_6$) δ: 8.71 (s, 1H), 8.18 (s, 1H), 8.04 (d, J=8.35 Hz, 1H), 7.56-7.96 (m, 7H)

EXAMPLE 184

4-Hydroxy-8-[3-methyl-4-(3-methylphenylsulfonyl)-phenyl]pyrazolo[1,5-a]-1,3,5-triazine m.p. 278°-280° C. (decomp.)

NMR (DMSO-d$_6$) δ: 8.65 (s, 1H), 8.18 (s, 1H), 8.15 (s, 2H), 8.02 (bs, 1H), 7.46-7.66 (m, 4H), 2.42 (s, 3H), 2.39 (s, 3H)

EXAMPLE 185

4-Hydroxy-8-(3-methoxy-4-phenylsulfinylphenyl)-pyrazolo[1,5-a]-1,3,5-triazine dihydrate 4-Hydroxy-8-(3-methoxy-4-phenylsulfinylphenyl)-pyrazolo[1,5-a]-1,3,5-triazine monohydrate (80 g) is dissolved in N,N-dimethylformamide (600 ml), and the insoluble material is filtered off. To the filtrate is added water (3 liters), and the resulting precipitate is separated by filtration and refluxed in acetone (1.6 liter) for 2 hours. After cooling, the precipitate is separated by m.p. 297°-298° C. (decomp.) filtration and refluxed in chloroform-methanol (1:1, 800 ml) for 2 hours. After cooling, the precipitate is again separated by filtration and refluxed in 50% ethanol (1.5 liter) for 3 hours. After cooling, the precipitate is separated by filtration and dried under reduced pressure at 80° C. for 10 hours to give the title compound (60.5 g).

m.p. 226°-235° C.

NMR (DMSO-d$_6$) (90 MHz) δ: 8.66 (s, 1H), 8.15 (s, 1H), 7.46-7.94 (m, 8H), 3.88 (s, 3H)

Elementary analysis:
Calcd. (%): C,53.72; H,4.51; N,13.92.
Found (%): C,54.10; H,4.70; N,13.96.

EXAMPLE 186

4-Hydroxy-8-(3-methoxy-4-phenylsulfinylphenyl)-pyrazolo[1,5-a]-1,3,5-triazine semihydrate 4-Hydroxy-8-(3-methoxy-4-phenylsulfinylphenyl)-pyrazolo[1,5-a]-1,3,5-triazine dihydrate (3 g) is suspended in ethanol (70 ml), and the mixture is refluxed for 3 hours. After cooling, the precipitate is separated by filtration and is again suspended in ethanol (70 ml), and the mixture is refluxed for 3 hours. After cooling, the precipitate is separated by filtration and dried under reduced pressure at 110° C. for 20 hours to give the title compound (2.8 g).

m.p. 245°-246° C. (decomp.)

NMR (DMSO-d$_6$) (270 MHz) δ: 8.69 (s, 1H), 8.18 (s, 1H), 7.90 (d, J=8.1 Hz, 1H), 7.76 (d, J=8.2 Hz, 1H), 7.50-7.71 (m, 6H), 3.89 (s, 3H)

Elementary analysis:
Calcd. (%): C,57.59; H,4.03; N,14.93.
Found (%): C,57.46; H,4.06; N,14.81.

EXAMPLE 187

4-Hydroxy-8-(3-methoxy-4-phenylsulfinylphenyl)-pyrazolo[1,5-a]-1,3,5-triazine

4-Hydroxy-8-(3-methoxy-4-phenylsulfinylphenyl)-pyrazolo[1,5-a]-1,3,5-triazine dihydrate (15 g) is suspended in ethyl acetate (450 ml), and the mixture refluxed for 3 hours. After cooling, the precipitate is separated by filtration and is again suspended in ethyl acetate (400 ml), and the mixture is refluxed for 3 hours. After cooling, the precipitate is separated by filtration and dried under reduced pressure at 120° C. for 50 hours to give the title compound (13.7 g).

NMR (DMSO-d$_6$) (270 MHz) δ: 8.69 (s, 1H), 8.18 (s, 1H), 7.90 (d, J=8.1 Hz, 1H), 7.77 (d, J=8.2 Hz, 1H), 7.50-7.70 (m, 6H), 3.89 (s, 3H)

Elementary analysis:
Calcd. (%): C,59.01; H,3.85; N,15.29.
Found (%): C,59.07; H,3.85; N,15.09.

Preparations of this invention are illustrated below.

PREPARATION

Film coated tablets are prepared from the following components.

| Components | Amount |
|---|---|
| 4-Hydroxy-8-[4-(4-methylphenylthio)-phenyl]pyrazolo[1,5-a]-1,3,5-triazine | 100 g |
| Avicel (tradename of microcrystalline cellulose, manufactured by Asahi Chemical, Japan) | 40 g |
| Corn starch | 30 g |
| Magnesium stearate | 2 g |
| TC-5 (tradename of hydroxypropyl methylcellulose manufactured by Shinetsh Kagaku Kogyo, Japan) | 10 g |
| Polyethylene glycol 6000 | 3 g |
| Castor oil | 40 g |
| Ethanol | 40 g |

4-Hydroxy-8-[4-(4-methylphenylthio)phenyl]-pyrazolo[1,5-a]-1,3,5-triazine, Avicel, corn starch and magnesium stearate are mixed and kneaded and the mixture is tabletted using a conventional pounder (R 10 mm) for sugar coating. The tablets thus obtained are coated with film coating agent consisting of TC-5, polyethylene glycol 6000, castor oil and ethanol to give film coated tablets.

The pharmacological properties of the compounds were tested as shown in the following Experiments.

Experiment 1 (In vitro)

(1) Preparation of Xanthine Oxidase Solution

ICR strain mice were decapitated and the small intestine of each mouse was rapidly perfused with cooled physiological saline solution and removed. The small intestine was homogenized in 4-fold volume of cooled phosphate buffered saline solution (PBS) and then centrifuged at 105,000 g for 60 minutes. The supernatant fluid was dialyzed overnight against PBS. The dialyzed solution thus prepared was stored at $-20°$ C. until used.

(2) Preparation of the Solution Containing the Present Compound

The compound of this invention was dissolved in DMSO (200 μl) and 2N NaOH (100 μl), and then PBS was added to prepare a solution (25 ml) containing $10^{-3}$M of the compound of this invention. This solution was diluted with PBS to prepare solutions containing the compound in the concentration of $10^{-4}$, $10^{-5}$, $10^{-6}$, $10^{-7}$, $10^{-8}$, $10^{-9}$, $10^{-10}$, and $10^{-11}$M, respectively.

(3) Method for the Measurement

The assay mixture, consisted of the composition mentioned below, was incubated at 37° C. for 5 minutes. The reaction was stopped by heating in boiling water for one minute. Twenty microliters of the supernatant was analyzed by high performance liquid chromatography (HPLC) under the conditions mentioned below.

Composition of Solution

Xanthine oxidase solution (diluted in 4-folds with PBS): 200 μl
Xanthine (1 mM): 100 μl
Solution containing the present compound: 200 μl
PBS: 500 μl Conditions of HPLC Column: osmosil packed column ($\phi$ 4. mm×150 mm, 5C$_{18}$×300)
Eluting solution: 10 mM phosphate buffer (pH 6.0)
Flow rate: 1.0 ml/minute
Detector: UV 292 nm
Sample volume: 20 μl
Retention time: 2.4 minutes (uric acid)

(4) Percent Inhibition of the Compound Against Xanthine Oxidase

The percent inhibition was calculated by the following equation.

$$\text{Percent inhibition (\%)} = \frac{[\text{Amount of uric acid in control solution}] - [\text{Amount of uric acid in the solution treated with the present compound}]}{\text{Amount of uric acid in control solution}^*} \times 100$$

*Control solution means a mixture of DMSO and 2N NaOH used for the preparation of the solution containing the present compound.

As to each of the solutions containing the present compound as prepared in the above (2), the percent inhibition was calculted, and IC$_{50}$ values were obtained from a plot of the percent inhibition against the log of the concentration of the compound of this invention.

As a positive control, a commercially available xanthine oxidase inhibitor, allopurinol (=4-hydroxypyrazolo[3,4-d]pyrimidine) was used.

The experimental results are shown in the table hereinafter.

Experiment 2 (In Vivo: Oral Administration)

(1) Animals, Method of Administration and Sampling of Serum

Normal male ICR mice (weighting about 30 g), were provided normal diet and tap water ad libitum. A test compound suspended in 0.5% CMC-Na was administered orally to the mice (each group: 6 mice) in a dose of 5 mg/kg. Four hours after the administration of the test compound, blood (about 0.6 ml) was collected from the vena cave inferior of mice under ether anesthesia, and the serum was separated from the blood in a usual manner.

(2) Measurement of Amount of Uric Acid in Serum

To the serum (200 μl) was added 10% perchloric acid (100 μl), and the mixture was centrifuged. To the supernatant fluid (100 μl) was added 0.2M Na$_2$HPO$_4$ (200 μl), and the mixture (20 μl) was analyzed by HPLC to measure the amount of uric acid. The HPLC was carried out under the following conditions.

Column: Cosmosil packed column ($\phi$ 4.6 mm×150 mm, 5C$_{18}$-300)
Eluting solution: 10 mM phosphate buffer (pH 6.0)
Flow rate: 1.0 ml/minute
Detector: UV 292 nm
Sample volume: 20 μl
Retention time: 2.4 minutes (uric acid)

(3) Lowering Effect of Test Compound on the Level of Uric Acid in Serum

The lowering rate of uric acid in serum was calculated by the following equation.

Lowering rate of uric acid in serum (%) =

$$\frac{[\text{Amount of uric acid in control animal}] - [\text{Amount of uric acid in the animal treated with the present compound}]}{\text{Amount of uric acid in control animal}} \times 100$$

As a positive control, a commercially available xanthine oxidase inhibitor, allopurinol was used.

The experimental results are shown in the table hereinafter.

| Example No. of Test compound | in vitro Xanthine oxidase inhibition (IC$_{50}$) | in vivo Lowering rate (%) of uric acid in serum (in 4 hours) |
|---|---|---|
| 17 | $3.0 \times 10^{-8}$ | Not tested |
| 19 | $1.6 \times 10^{-7}$ | Not tested |
| 21 | $3.1 \times 10^{-7}$ | Not tested |
| 30 | $7.1 \times 10^{-8}$ | 47% |
| 31 | $1.0 \times 10^{-8}$ | 63.5% |
| 33 | $1.8 \times 10^{-8}$ | 62% |
| 39 | $4.5 \times 10^{-8}$ | Not tested |
| 41 | $2.4 \times 10^{-8}$ | 60.1% |
| 43 | $1.0 \times 10^{-8}$ | 60.6% |
| 52 | $5.3 \times 10^{-8}$ | Not tested |
| 53 | $1.5 \times 10^{-8}$ | Not tested |
| 54 | $5.5 \times 10^{-7}$ | 65.2% |
| 70 | $5.2 \times 10^{-9}$ | Not tested |
| 73 | $4.0 \times 10^{-8}$ | Not tested |
| 74 | $5.0 \times 10^{-8}$ | Not tested |
| 95 | $3.6 \times 10^{-9}$ | Not tested |
| 96 | $1.0 \times 10^{-10}$ | Not tested |
| 97 | $4.5 \times 10^{-10}$ | Not tested |
| 99 | $1.4 \times 10^{-10}$ | Not tested |
| 100 | $7.5 \times 10^{-10}$ | Not tested |
| 101 | $5.4 \times 10^{-8}$ | Not tested |
| 105 | $2.2 \times 10^{-9}$ | Not tested |
| 107 | $6.4 \times 10^{-8}$ | Not tested |
| 109 | $3.6 \times 10^{-9}$ | Not tested |
| 112 | $6.5 \times 10^{-9}$ | Not tested |
| 113 | $3.4 \times 10^{-8}$ | Not tested |
| 134 | $7.6 \times 10^{-8}$ | Not tested |
| 136 | $3.2 \times 10^{-8}$ | Not tested |
| 138 | $3.9 \times 10^{-8}$ | Not tested |
| 142 | $5.2 \times 10^{-8}$ | Not tested |
| 143 | $3.6 \times 10^{-8}$ | Not tested |
| 146 | $2.7 \times 10^{-9}$ | 47.0% |
| 167 | $5.0 \times 10^{-9}$ | Not tested |
| 170 | $8.0 \times 10^{-9}$ | 57.2% |
| 171 | $2.4 \times 10^{-9}$ | 73.6% |
| 187 | $2.5 \times 10^{-8}$ | 63.9% |
| Reference Allopurinol | $2.0 \times 10^{-6}$ | 34% |

What is claimed is:

1. A pyrazolotriazine compound of the formula:

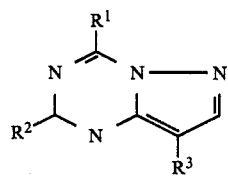

wherein
$R^1$ is a hydroxy or a $C_{1-6}$ alkanoyloxy,
$R^2$ is hydrogen atom, hydroxy, or mercapto,
$R^3$ is (1) an unsaturated heterocyclic group selected from the group consisting of pyrrolyl, pyridyl, thienyl, thiopyranyl, indolyl, benzothienyl, 2,3-dihydrobenzothienyl, thiochromanyl, and dibenzothienyl which may optionally have one or two substituents selected from a halogen atom, nitro, and phenylthio, (2) naphthyl, and (3) a phenyl which may optionally have one to three substituents selected from the group consisting of (i) a $C_{1-6}$ alkyl, (ii) phenyl, (iii) a $C_{1-6}$ alkoxycarbonyl, (iv) cyano, (v) nitro, (vi) a $C_{1-6}$ alkoxy, (vii) a phenyl-$C_{1-6}$ alkoxy, (viii) a phenylthio-$C_{1-6}$ alkyl, (ix) phenoxy, (x) a group of the formula:

wherein R is a $C_{1-6}$ alkyl, a halogen-substituted $C_{1-6}$ alkyl, a phenyl which may optionally have one to three substituents selected from a halogen atom, a $C_{1-6}$ alkyl and a $C_{1-6}$ alkoxy, or pyridyl, and l is an integer of 0, 1 or 2, (xi) a halogen atom, (xii) a phenyl-$C_{1-6}$ alkyl, (xiii) carboxy, (xiv) a $C_{1-6}$ alkanoyl, (xv) a benzoyl which may optionally have one to three substituents selected from a halogen atom, a phenyl $C_{1-6}$ alkoxy and hydroxy on the phenyl ring, (xvi) amino, (svii) hydroxy, (xviii) a $C_{1-6}$ alkanoyloxy, (xix) a group of the formula:

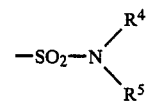

wherein $R^4$ and $R^5$ are the same or different and are each hydrogen atom, a cycloalkyl, a $C_{1-6}$ alkyl which may optionally have a substituent selected from hydroxy, furyl, thienyl, tetrahydrofuranyl and phenyl, a phenyl which may optionally have one to three substituents selected from a $C_{1-6}$ alkyl, a hydroxy-substituted $C_{1-6}$ alkyl, a $C_{1-6}$ alkanonyl, cyano, carboxy, a $C_{1-6}$ alkoxycarbonyl, hydroxy, a $C_{1-6}$ alkoxy, and a halogen atom, or a heterocyclic group selected from pyridyl, pyrimidinyl, thiazolyl, isoxazolyl, and purazolyl, said heterocyclic group being optionaslly substituted by a $C_{1-6}$ alkyl, amino, or a $C_{1-6}$ alkyl, amino, or a $C_{1-6}$ alkanoylamino, or $R^4$ and $R^5$ may join together with the adjacent nitrogen atom to form a saturated 5- or 6-membered heterocyclic group, which may optionally be intervened with oxygen atom, selected from the group consisting of pyrrolidinyl, piperidinyl, tetrahydro-1,2-oxazinyl, tetrahydro-1,3-oxazinyl, and morpholine, or (xx) a group of the formula:

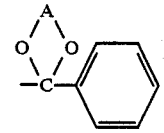

wherein A is a $C_{1-6}$ alkylene.

2. The compound according to claim 1, wherein $R^1$ is hydroxy and $R^2$ is hydroxy or mercapto.

3. The compound according to claim 2, wherein $R^3$ is a phenyl which is substituted by a group of the formula:

wherein R is a $C_{1-6}$ alkyl, a halogen-substituted $C_{1-6}$ alkyl, a phenyl which may optionally have one to three substituents selected from a halogen atom, a $C_{1-6}$ alkyl and a $C_{1-6}$ alkoxy, or pyridyl, and l is an integer of 0, 1 or 2 and may optionally have other one or two substituents selected from the group consisting of a $C_{1-6}$ alkyl, a $C_{1-6}$ alkoxy, a halogen atom, and a $C_{1-6}$ alkylthio.

4. The compound according to claim 2, wherein $R^3$ is a phenyl having one to three substituents selected from the group consisting of a $C_{1-6}$ alkyl, a $C_{1-6}$ alkoxy, nitro, a halogen atom, a phenyl($C_{1-6}$)alkoxy, and a benzoyl having optionally one to three substituents selected from a halogen atom, a phenyl($C_{1-6}$)alkoxy and hydroxy.

5. The compound according to claim 2, wherein $R^3$ is a phenyl which is substituted by a group of the formula:

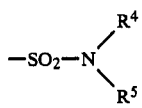

(wherein $R^4$ is hydrogen atom and $R^5$ is a thienyl($C_{-6}$)alkyl, or a phenyl which may optionally have one to three substituents selected from a $C_{1-6}$ alkyl, a hydroxy-substituted $C_{1-6}$ alkyl, a $C_{1-6}$ alkoxycarbonyl, hydroxy, a $C_{1-6}$ alkoxy, and a halogen atom; or $R^4$ and $R^5$ are the same and are each a $C_{1-6}$ alkyl) and has optionally further a substituent selected from a $C_{1-6}$ alkyl or a halogen atom.

6. The compound according to claim 3, wherein $R^3$ is a phenyl which is substituted by a group of the formula:

(wherein R is a $C_{1-6}$ alkyl or phenyl, and l is an integer of 0, 1 or 2.

7. The compound according to claim 1, wherein $R^2$ is hydrogen atom, and Rhu 3 is (1) an unsaturated heterocyclic group selected from pyrrolyl, pyridyl, thienyl, thiopyranyl, indolyl, benzothienyl, 2,3-dihydrobenzothienyl, thiochromanyl, or dibenzothienyl, which may optionally have one or two substituents selected from a halogen atom, nitro, and phenylthio, (2) naphthyl, and (3) a phenyl which may optionally have one to three substituents selected from the group consisting of (i) a $C_{1-6}$ alkyl, (ii) phenyl, (iii) a $C_{1-6}$ alkoxycarbonyl, (iv) cyano, (v) nitro, (vi) a $C_{1-6}$ alkoxy, (vii) a phenyl($C_{1-6}$)alkoxy, (viii) a phenylthio($C_{1-6}$)alkyl, (ix) phenoxy, (x) a group of the formula:

wherein $C_{1-6}$ alkyl, a phenyl which may optionally have one to three substituents selected from a halogen atom, a $C_{1-6}$ alkyl and a $C_{1-6}$ alkoxy, or pyridyl, and l is an integer of 0, 1 or 2, (xi) a halogen atom, (xii) a phenyl($C_{1-6}$)alkyl, (xiii) carboxy, (xiv) a $C_{1-6}$ alkanoyl, (xv) a benzoyl which may optionally have one to three substituents selected from a halogen atom, a phenyl($C_{1-6}$)alkoxy and hydroxy on the phenyl ring, (xvi) amino, (xvii) hydroxy, (xviii) a $C_{1-6}$ alkanoyloxy, (xix) a group of the formula:

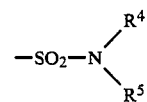

wherein $R^4$ and $R^5$ are the same or different and are each hydrogen atom, a cycloalkyl, a $C_{1-6}$ alkyl which may optionally have a substituent selected from hydroxy, furyl, thienyl, tetrahydrofuranyl and phenyl, a phenyl which may optionally have one to three substituents selected from a $C_{1-6}$ alkyl, a hydroxy-substituted $C_{1-6}$ alkyl, a $C_{1-6}$ alkanoyl, cyano, carboxy, a $C_{1-6}$ alkoxycarbonyl, hydroxy, a $C_{1-6}$ alkoxy, and a halogen atom, or a heterocyclic group selected from pyridyl, pyrimidinyl, thiazolyl, isoxazolyl, and pyrazolyl, said heterocyclic group being optionally substituted by a $C_{1-6}$ alkyl, amino, or a $C_{1-6}$ alkanoylamino, or $R^4$ and $R^5$ may join together with the adjacent nitrogen atom to form a heterocyclic group selected from the group consisting of pyrrolidinyl, piperidinyl, tetrahyro-1,2-oxazinyl, tetrahydro-1,3-oxazinyl, and morpholino, or (xx) a group of the formula:

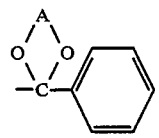

wherein A is a $C_{1-4}$ alkylene.

8. The compound according to claim 7, wherein $R^1$ is hydroxy.

9. The compound according to claim 7, wherein $R^1$ is a $C_{1-6}$ alkanoyloxy.

10. The compound according to claim 8, wherein $R^3$ is a phenyl which has at least one substituted of a group of the formula:

(wherein R is a $C_{1-6}$ alkyl, a halogen-substituted $C_{1-6}$ alkyl, a phenyl which may optionally have one to three substituents selected from a halogen atom, a $C_{1-6}$ alkyl and a $C_{1-6}$ alkoxy, or pyridyl, and l is an integer of 0, 1 or 2 and may optionally have further one or two substituents selected from the group consisting of (i) a $C_{1-6}$ alkyl, (ii) phenyl, (iii) a $C_{1-6}$ alkoxycarbonyl, (iv) cyano, (v) nitro, (vi) a $C_{1-6}$ alkoxy, (vii) a phenyl($C_{1-6}$)alkoxy, (viii) a phenylthio($C_{1-6}$)alkyl, (ix) phenoxy, (x) a halogen atom, (xi) a phenyl($C_{1-6}$)alkyl, (xii) carboxy, (xiii) a $C_{1-6}$ alkanoyl, (xiv) a benzoyl which may optionally have one to three substituents selected from a halogen atom, a phenyl($C_{1-6}$)alkoxy and hydroxy on the phenyl ring, (xv) amino, (xvi) hydroxy, (xvii) a $C_{1-6}$ alkanoyloxy, (xviii) a group of the formula:

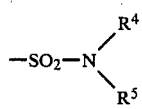

wherein $R^4$ and $R^5$ are the same or different and are each hydrogen atom, a cycloalkyl, a $C_{1-6}$ alkyl which may optionally have a substituent selected from hydroxy, furyl, thienyl, tetrahydrofuranyl and phenyl, a phenyl which may optionally have one to three substituents selected from a $C_{1-6}$ alkyl, a hydroxy-substituted $C_{1-6}$ alkyl, a $C_{1-6}$ alkanoyl, cyano, carboxy, a $C_{1-6}$ alkoxycarbonyl, hydroxy, a $C_{1-6}$ alkoxy, and a halogen atom, or a heterocyclic group selected from pyridyl, pyrimidinyl, thiazolyl, isoxazolyl, and pyrazolyl, said heterocyclic group being optionally substituted by a $C_{1-6}$ alkyl, amino, or a $C_{1-6}$ alkanoylamino, or $R^4$ and $R^5$ may join together with the adjacent nitrogen atom to form a heterocyclic group selected from the group consisting of pyrrolidinyl, piperidinyl, tetrahyro-1,2-oxazinyl, tetrahydro-1,3-oxazinyl, and morpholino, or (xx) a group of the formula:

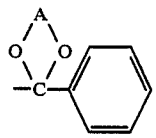

wherein A is a $C_{1-4}$ alkylene

11. The compound according to claim 8, wherein $R^3$ is a phenyl which has at least one substituent of the formula

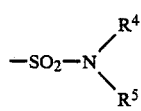

(wherein $R^4$ and $R^5$ are the same or different and are each hydrogen atom, a cycloalkyl, a $C_{1-6}$ alkyl which may optionally have a substituent selected from hydroxy, furyl, thienyl, tetrahydrofuranyl and phenyl, a phenyl which may optionally have one to three substituents selected from a $C_{1-6}$ alkyl, a hydroxy-substituted $C_{1-6}$ alkyl, a $C_{1-6}$ alkanoyl, cyano, carboxy, a $C_{1-6}$ alkoxycarbonyl, hydroxy, a $C_{1-6}$ alkoxy, and a halogen atom, or a heterocyclic group selected from pyridyl, pyrimidinyl, thiazolyl, isoxazolyl, and pyrazolyl, said heterocyclic group being optionally substituted by a $C_{1-6}$ alkyl, amino, or a $C_{1-6}$ alkanoylamino, or $R^4$ and $R^5$ may join together with the adjacent nitrogen atom to form a heterocyclic group selected from the group consisting of pyrrolidinyl, piperidinyl, tetrahyro-1,2-oxazinyl, tetrahydro-1,3-oxazinyl, and morpholino) and may optionally have further one or two substituents selected from the group consisting of (i) a $C_{1-6}$ alkyl, (ii) phenyl, (iii) a $C_{1-6}$ alkoxycarbonyl, (iv) cyano, (v) nitro, (vi) a $C_{1-6}$ alkoxy, (vii) a phenyl-($C_{1-6}$)alkoxy, (viii) a phenylthio($C_{1-6}$)alkyl, (ix) phenoxy, (x) a group of the formula:

wherein R is a $C_{1-6}$ alkyl, a halogen-substituted $C_{1-6}$ alkyl, a phenyl which may optionally have one to three substituents selected from a halogen atom, a $C_{1-6}$ alkyl and a $C_{1-6}$ alkoxy, or pyridyl, and l is an integer of 0, 1 or 2, (xi) a halogen atom, (xii) a phenyl($C_{1-6}$)alkyl, (xiii) carboxy, (xiv) a $C_{1-6}$ alkanoyl, (xv) a benzoyl which may optionally have one to three substituents selected from a halogen atom, a phenyl($C_{1-6}$)alkoxy and hydroxy on the phenyl ring, (xvi) amino, (xvii) hydroxy, (xviii) a $C_{1-6}$ alkanoyloxy, and (xix) a group of the formula:

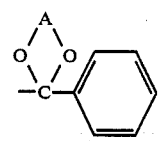

wherein A is a $C_{1-4}$ alkylene

12. The compound according to claim 8, wherein $R^3$ is a phenyl which has any one of substituents selected from the group consisting of (i) a $C_{1-6}$ alkyl, (ii) phenyl, (iii) a $C_{1-6}$ alkoxycarbonyl, (iv) cyano, (v) nitro, (vi) a $C_{1-6}$ alkoxy, (vii) a phenyl($C_{1-6}$)alkoxy, (viii) a phenylthio($C_{1-6}$)alkyl, (ix) phenoxy, (x) a halogen atom, (xi) a phenyl($C_{1-6}$)alkyl, (xii) carboxy, (xiii) a $C_{1-6}$ alkanoyl, (xiv) a benzoyl which may optionally have one to three substituents selected from a halogen atom, a phenyl($C_{1-6}$)alkoxy and hydroxy on the phenyl ring, (xv) amino, (xvi) hydroxy, (xvii) a $C_{1-6}$ alkanoyloxy, and (xviii) a group of the formula:

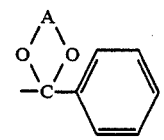

wherein A is a $C_{1-4}$ alkylene, and may optionally have further one or two substituents selected from a group the formula:

wherein R is a $C_{1-6}$ alkyl, a halogen-substituted $C_{1-6}$ alkyl, a phenyl which may optionally have one to three substituents selected from a halogen atom, a $C_{1-6}$ alkyl and a $C_{1-6}$ alkoxy, or pyridyl, and l is an integer of 0, 1 or 2, and a group of the formula:

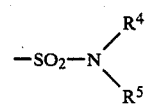

wherein $R^4$ and $R^5$ are the same or different and are each hydrogen atom, a cycloalkyl, a $C_{1-6}$ alkyl which may optionally have a substituent selected from hydroxy, furyl, thienyl, tetrahydrofuranyl and phenyl, a phenyl which may optionally have one to three substituents selected from a $C_{1-6}$ alkyl, a hydroxy-substituted $C_{1-6}$ alkyl, a $C_{1-6}$ alkanoyl, cyano, carboxy, a $C_{1-6}$ alkoxycarbonyl, hydroxy, a $C_{1-6}$ alkoxy, and a halogen atom, or a heterocyclic group selected from pyridyl, pyrimidinyl, thiazolyl, isoxazolyl, and pyrazolyl, said heterocyclic group being optionally substituted by a $C_{1-6}$ alkyl, amino, or a $C_{1-6}$ alkanoylamino, or $R^4$ and $R^5$ may join together with the adjacent nitrogen atom to form a heterocyclic group seected from the group consisting of pyrrolidinyl, piperidinyl, tetrahyro-1,2-oxazinyl, tetrahydro-1,3-oxazinyl, and morpholino.

13. The compound according to claim 10, wherein $R^3$ is a phenyl which is substituted by a group of the formula:

wherein R is a $C_{1-6}$ alkyl, a halogen-substituted $C_{1-6}$ alkyl, a phenyl which may optionally have one to three substituents selected from a halogen atom, a $C_{1-6}$ alkyl and a $C_{1-6}$ alkoxy, or pyridyl, and l is an integer of 0, 1 or 2 and may optionally have other one or two substituents selected from the group consisting of a $C_{1-6}$ alkyl, a $C_{1-6}$ alkoxy, a halogen atom, and a $C_{1-6}$ alkylthio.

14. The compound according to claim 11, wherein $R^3$ is a phenyl having one to three substituents selected from the group consisting of a $C_{1-6}$ alkyl, a $C_{1-6}$ alkoxy, nitro, a halogen atom, a phenyl($C_{1-6}$)alkoxy, and a benzoyl having optionally one to three substituents selected from a halogen atom, a phenyl($C_{1-6}$)alkoxy and hydroxy.

15. The compound according to claim 12, wherein $R^3$ is a phenyl which is substituted by a group of the formula:

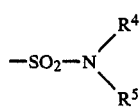

(wherein $R^4$ is hydrogen atom and $R^5$ is a thienyl($C_{1-6}$)alkyl, or a phenyl which may optionally have one to three substituents selected from a $C_{1-6}$ alkyl, a hydroxy-substituted $C_{1-6}$ alkyl, a $C_{1-6}$ alkoxycarbonyl, hydroxy, a $C_{1-6}$ alkoxy, and a halogen atom; or $R^4$ and $R^5$ are the same and are each a $C_{1-6}$ alkyl) and has optionally further a substituent selected from a $C_{1-6}$ alkyl or a halogen atom.

16. The compound according to claim 13, wherein $R^3$ is a phenyl which is substituted by a group of the formula:

wherein R is a $C_{1-6}$ alkyl or phenyl, and l is an integer of 0, 1 or 2.

17. The compound according to claim 13, wherein $R^3$ is a phenyl which is substituted by a group of the formula:

wherein R is a halogen-substituted $C_{1-6}$ alkyl, a phenyl which may optionally have one to three substituents selected from a halogen atom, a $C_{1-6}$ alkyl and a $C_{1-6}$ alkoxy, or pyridyl, and l is an integer of 0, 1 or 2.

18. The compound according to claim 13, wherein $R^3$ is a phenyl having one to three substituents selected from the group consisting of a $C_{1-6}$ alkyl, a $C_{1-6}$ alkoxy, a halogen atom, and a $C_{1-6}$ alkylthio.

19. The compound according to claim 13, which is 8-(2-fluoro-3-methyl-4-methylthiophenyl)-4-hydroxypyrazolo-[1,5-a]-1,3,5-triazine.

20. The compound according to claim 13, which is 4-hydroxy-8-(4-phenylsulfinylphenyl)pyrazolo[1,5-a]-1,3,5-triazine.

21. The compound according to claim 13, which is 4-hydroxy-8-(3-methyl-4-phenylsulfinylphenyl)-pyrazolo-[1,5-a]-1,3,5-triazine.

22. the compound according to claim 13, which is 4-hydroxy-8-(3-methoxy-4-pheenylsulfinylphenyl)-pyrazolo[1,5-a]-1,3,5-triazine monohydrate.

23. A pharmaceutical composition for the prophylaxis and treatment of gout, which comprises an active ingredient a prophylactically and therapeutically effective amount of a pyrazolotriazine compound of the formula (1) as set forth in claim 1 in admixture with a pharmaceutically acceptable carrier or diluent.

24. A method for the propylaxis and treatment of gout, which comprising administering a prophylactically and therapeutically effective amount of a pyrazolotriazine compound of the formula (1) as set forth in claim 1 to a subject suffering from gout.

* * * * *